United States Patent [19]

Watson et al.

[11] Patent Number: 4,891,315
[45] Date of Patent: * Jan. 2, 1990

[54] PRODUCTION OF HERPES SIMPLEX VIRAL PROTEINS

[75] Inventors: Roger J. Watson, Minneapolis; John H. Weis, Brookline; Lynn W. Enquist, Excelsior, all of Minn.

[73] Assignee: American Cyanamid Company, Stamford, Conn.

[ * ] Notice: The portion of the term of this patent subsequent to Apr. 4, 2006 has been disclaimed.

[21] Appl. No.: 510,551

[22] Filed: Jul. 6, 1983

Related U.S. Application Data

[63] Continuation-in-part of Ser. No. 436,368, Oct. 25, 1982, which is a continuation-in-part of Ser. No. 400,028, Jul. 20, 1982.

[51] Int. Cl.$^4$ ............... C12P 21/00; C12P 21/02; C12P 21/04; C12N 15/00; C12N 5/00; C12N 1/00; C12N 1/20; C12N 1/16; C12N 1/18; C07H 21/04
[52] U.S. Cl. .................... 435/69.3; 435/70; 435/71; 435/172.1; 435/172.3; 435/240.1; 435/240.2; 435/243; 435/252.3; 435/255; 435/256; 435/320; 435/252.33; 536/27; 935/12; 935/28; 935/29; 935/52; 935/66; 935/67; 935/70; 935/72; 935/73
[58] Field of Search ............. 435/68, 70, 71, 91, 435/172.3, 253, 243, 240, 241, 517, 255, 256, 240.1, 317.1, 320, 240.2; 536/27; 935/11, 12, 52, 66–75, 28, 29, 31, 32

[56] References Cited

U.S. PATENT DOCUMENTS

| | | |
|---|---|---|
| 4,237,224 | 12/1980 | Cohen et al. ............... 435/68 |
| 4,332,892 | 6/1982 | Ptashne et al. ............ 435/68 |
| 4,338,397 | 7/1982 | Gilbert et al. ............. 435/68 |
| 4,342,832 | 8/1982 | Goeddel et al. .......... 435/172.3 |
| 4,349,629 | 9/1982 | Carey et al. ............. 435/172.3 |
| 4,366,246 | 12/1982 | Riggs ..................... 435/172.3 |
| 4,374,127 | 2/1983 | Larson et al. ............ 424/89 |
| 4,419,446 | 12/1983 | Howley et al. ............ 435/317 |
| 4,430,437 | 2/1984 | Hamper et al. ........... 436/548 |
| 4,618,578 | 10/1986 | Burke et al. .............. 435/68 |

OTHER PUBLICATIONS

Henikoff et al.; Nature 289: 33 (1981).
Zhidkova et al., "Molecular cloning of DNA of Herpes Simplex Viruses", Chem. Abstr. 100: 80679z (1984) of (USSR) Deposited Doc. (1982).
Roberts et al., "A general method for maximizing the expression of a cloned gene", Proc. Natl. Acad. Sci. USA 76: 760 (1979).
Hitzeman et al., "Expression of a Human Gene for Interferon in Yeast", Nature 293: 717 (1981).
Itakura et al., 1977, Science 198; 1056.
Villa-Komaroff et al., 1978, Proc. Natl. Acad. Sci. U.S.A. 75: 3727.
Seeberg et al., 1978; Nature 276: 795.
Mercereau-Puijalon et al., 1978, Nature 275: 505.
Fraser et al., 1978, Proc. Natl. Acad. Sci. USA 75: 5936.
Guarente et al., 1980, Cell 20: 543.
Norrild, Current Topics in Microbiol. and Immunol. 19:67.
Ruyechan et al., 1979, J. Virol. 29:667.
Lee et al., 1982, J. Virol. 43:41.
Umene et al., 1981, Gene 13:251.
Watson et al., 1981, J. Virol. 37:431.
Marsden et al., J. Virol. 28:624 (1978).
Halliburton, J. Gen. Virol., 48:1 (1980).
Showalter et al., 1981, Infection and Immunity 34:684.

(List continued on next page.)

Primary Examiner—James Martinell
Attorney, Agent, or Firm—Robert P. Raymond

[57] ABSTRACT

Methods and compositions are provided for the cloning and expression of Herpes Simplex Virus (HSV type 1 or type 2) glycoprotein (gD) gene in single-cell host organisms. Also described are methods for culturing these novel single-cell organisms to produce HSV-gene products. The HSV gD-related polypeptides produced by the recombinant DNA techniques described herein may be formulated for use as immunogens in vaccines to protect against HSV-1 and HSV-2 infections.

59 Claims, 19 Drawing Sheets

OTHER PUBLICATIONS

Eisenberg et al., 1982, J. Virol., 41:478.
Eisenberg et al., 1982, J. Virol, 41: 1099–1104.
Pereira et al., 1982, Infec. Immun. 35:363–367.
Dix et al., 1981, Infec. Immun. 34: 192–199.
Pereira et al., 1980, Infec. Immun. 29:724–732.
Randall et al., 1980, J. Gen. Virol., 48:297–310.
Eisenberg et al., 1980, J. Virol. 35: 428–435.
Cohen et al., 1980, J. Virol. 34:521–531.
Cohen et al., 1978, J. Virol. 27:172–181.
Eisenberg et al., 1979, J. Virol., 31: 608–620.
Cohen et al., 1980, J. Virol., 36: 429–439.
Ponce de Leon et al., 1973, J. Virol., 12: 766–774.
Cohen et al., 1972, J. Virol. 10: 1021–1030.
Pizer et al., 1980, J. Virol., 34: 142–153.
Kreil: Ann. Rev. Biochem. 50: 317 (1981).
Taniguchi et al., Proc. Natl. Acad. Sci. USA 77: 5230 (1980).
Rose et al., Proc. Natl. Acad. Sci. USA 78: 6670 (1980).
Maxam et al., Proc. Natl. Acad. Sci. USA 74: 560 (1977).
Enquist et al., 1979, Science 203: 541–544.
Docherty et al., 1981, J. Virol. 40(1): 126–132.
Galloway et al., 1982, J. Virol. 42(2): 530–537.
Weis et al., 1983, Nature 302: 72–74.
Watson et al., 1982, Science 218: 381–383.
Lee et al., 1982, Proc. Natl. Acad. Sci. U.S.A. 79: 6612–6616.
Berman et al., *Trends in Biochemistry*, vol. 3, pp. 51–53 (1985).
Post, et al.–Proceedings National Academy of Science, U.S.A., vol. 77, No. 7, pp. 4201–4205, Jul. 1980.

FIG. 3

```
                GTG GCC CCG GCC CCC AAC AAA AAT CAC GGT AGC CCG GCC GTG TGA CAC TAT CGT CCA TAC     60
        CGA CCA CAC CGA CGA ACC CCT AAG GGG GAG GGG CCA TTT TAC GAG GAG GGG TAT AAC           120
                                                                         HindIII
        AAA GTC TGT CTT TAA AAA GCA GGG GTT AGG GAG TTG TTC GGT CAT AAG CTT CAG CGC GAA      180
        CGA CCA ACT ACC CCG ATC ATC AGT CCT TAA GGT CTC TTT TGT GTG GTG GTT TCC GGT         240
SIGNAL    5,82      62  60,66,73,74
        ATG GGG ACT GCC GCC AGG TTG GGG GCC GTG ATT TTG TTT GTC GTC ATA GTG GGC CTC--       300
        MET GLY THR ALA ALA ARG LEU GLY ALA VAL ILE LEU PHE VAL VAL ILE VAL GLY LEU
            NcoI    SacII                   71
        CAT GGG GTC CGC GGC AAA TAT GCC TTG GCG GAT GCC TCT CTC AAG ATG GCC GAC CCC AAT    360
  1     HIS GLY VAL ARG GLY LYS TYR ALA LEU ALA ASP ALA SER LEU LYS MET ALA ASP PRO ASN
                                            PvuII
                                                  4-2,3-25,90-N
        CGC TTT CGG GAA GAC CTT CCG GTC CAG CTG LEU ACC GAC CCT CCG GGG GTC CGG            420
 21     ARG PHE ARG GLU ASP LEU PRO VAL GLN LEU LEU THR ASP PRO PRO GLY VAL ARG CGC GTG TAC CAC ATC CAG GCG CTA CCG GAC CCG TTC CAG CCC CCC AGC CTC CCG ATC        480
 41     ARG VAL TYR HIS ILE GLN ALA GLY LEU PRO ASP PRO PHE GLN PRO PRO SER LEU PRO ILE ACG GTT TAC TAC GCC GTG TTG GAG CGC GCC AGC GTG CTC CTA AAC CAA CCG TCG            540
 61     THR VAL TYR TYR ALA VAL LEU GLU ARG ALA CYS SER VAL LEU LEU ASN ALA PRO SER GAG GCC CCC CAG ATT GTC CGC GGG GCC TCC GAA GAC GTC CGG AAA CAA CCC AAC CTG        600
 81     GLU ALA PRO GLN ILE VAL ARG GLY ALA SER GLU ASP VAL ARG LYS GLN PRO ASN LEU
            SacII
        ACC ATC GCT TGG TTT CGG ATG GGA GGC AAC TGT GCT ATC CCC ATC CCG ATG GTC TAC        660
101     THR ILE ALA TRP PHE ARG MET GLY GLY ASN CYS ALA ILE PRO ILE PRO MET VAL TYR ACC GAA TGC TCC TAC AAG TCT CTG GGC GCC TGT CCC ATC CGA ACG CAG CCC CGG TGG        720
121     THR GLU CYS SER TYR LYS SER LEU GLY ALA CYS PRO ILE ARG THR GLN PRO ARG TRP AAC TAT TAT GAC AGC TTC AGC GTC AGC GAG GAT AAC CTG GGG TTG CTG ATG CAC GCC        780
141     ASN TYR TYR ASP SER PHE SER ALA VAL SER GLU ASP ASN LEU GLY PHE LEU MET HIS ALA CCC GCG TTT GAG ACC GGC ACG GGC TAC CTG CGG GTG CTC AAG ATA AAC GAC TGG ACG GAG    840
161     PRO ALA PHE GLU THR GLY THR GLY TYR LEU ARG VAL LEU LYS ILE ASN ASP TRP THR GLU ATT ACA CAG TTT ATC CTG GAG CAC CGA GCC AAG GGC TCC TGT AAG TAC GCC CTC CCG CTG    900
201     ILE THR GLN PHE ILE LEU GLU HIS ARG ALA LYS GLY SER CYS LYS TYR ALA LEU PRO LEU
```

FIG. 3 CONT.

|     |                                                                                                                                  |      |
|-----|----------------------------------------------------------------------------------------------------------------------------------|------|
| 221 | CGC ATC CCC CCG TCA GCC CTC TCC CCC CAG GCC TAC CAG CAG GGG GTG ACG GTG GAC<br>ARG ILE PRO PRO SER ALA CYS LEU SER PRO GLN ALA TYR GLN GLN GLY VAL THR VAL ASP | 960  |
| 241 | AGC ATC GGG ATG CTG CCC CGC TTC ATC CCC GAG AAC CAG GAG ACC GTC GCC GTA TAC AGC<br>SER ILE GLY MET LEU PRO ARG PHE ILE PRO GLU ASN GLN GLU THR VAL ALA VAL TYR SER | 1020 |
| 261 | TTG AAG ATC GCC GGG TGC CAC GGG CCC AAG ACG AGC ACC CTG CTG CCC CCG<br>LEU LYS ILE ALA GLY TRP HIS GLY PRO LYS ALA PRO TYR THR SER THR LEU LEU PRO PRO<br>↓90-9 | 1080 |
| 281 | GAG CTG TCC GAG GAG ACC CCC AAC GCC ACG CAG GAA CTC GCC CCG GAA GAC GAT<br>GLU LEU SER GLU GLU THR PRO ASN ALA THR GLN GLU LEU ALA PRO GLU ASP ASP<br>↓90-6 ↓90-2 | 1140 |
| 301 | TCG GCC CTC TTG GAG CTG GAC GAC CCC GTG GGG ACG GTG GCG CCG CAA ATC CCA CCA AAC TGG CAC<br>SER ALA LEU LEU GLU LEU ASP ASP PRO VAL GLY THR VAL ALA PRO GLN ILE PRO PRO ASN TRP HIS<br>↓90-10 ↓4-2,82 | 1200 |
| 321 | ATC CCG TCG ATC CAG GAC GCC GCG ACG CCT TAC CAT CCC CCG GCC ACC CCG AAC AAC ATG<br>ILE PRO SER ILE GLN ASP ALA ALA THR PRO TYR HIS PRO PRO ALA THR PRO ASN ASN MET<br>↓90-5 | 1260 |
| 341 | Transmembrane<br>GGC CTG ATC GCC GGC GTG GGC AGT CTC CTG GCA GCC CTG GTC ATT TGC GGA ATT<br>GLY LEU ILE ALA GLY VAL GLY SER LEU LEU ALA ALA LEU VAL ILE CYS GLY ILE | 1320 |
| 361 | GTG TAC TGG ATG CAC CGC CGG ACT CGG AAA GCC CCA AAG CGC ATA CGC CTC CAC ATC<br>VAL TYR TRP MET HIS ARG ARG THR ARG LYS ALA PRO LYS ARG ILE ARG LEU PRO HIS ILE<br>↓3-25 ↓90-12 | 1380 |
| 381 | CGG GAA GAC GAC CAG CCG TCC TCG CAG CCC TTG CAC CAG TGG GAC CTT AAC TCC ATA TAA AGC GAG<br>ARG GLU ASP ASP GLN PRO SER SER GLN PRO LEU HIS GLN TRP ASP LEU ASN SER ILE ***   | 1440 |
|     | GGG TGC GGG GGG GTC AGG TCT GCG GGG TTG GAC TGG GAC CTT AAC TCC ATA TAA AGC GAG                                                  | 1500 |
|     | TCT GGA AGG GGG GAA AGG CGG ACA GTC GAT AAG TCG GTA GCG GAC GGG GAC GCG CAC CTG TTC         | 1560 |
|     | CGC CTG TCG CAC CCA CAG CTT TTT CGC GAA CCG TCC CGT TTT CGG GAT<br>                    NruI | 1608 |

FIG. 5

```
    CRO
ATG GAA CAA CGC ATA ACC
MET GLU GLN ARG ILE THR

CTG AAA GAT TAT GCA ATG
LEU LYS ASP TYR ALA MET

CGC TTT GGG CAA ACC AAG
ARG PHE GLY GLN THR LYS

ACA GCT AAA GAT CTG CCC
THR ALA LYS ASP LEU PRO gD-1
CTG ACC GAC CCT.....
LEU THR ASP PRO.....
```

FIG. 12

```
     CTT GGG GGG GGG GAA GAA ACT AAA AAC ACA TCA AGC CCA CCC ATC CCA CAA GGG                    60
     GGG TTA TGG CGG ACC CAC CGC ACC ATA CTC CGA TTC GAC CAC ATA TGC AAC CAA ATC               160
     ACC CCC AGA GGG GAG GTT CCA TTT TTA CGA GGA GGA GTA TAA TAG AGT CTT TGT GTT               180
     TAA AAC CCG GGG TCG GTG TGG TCG GTC ATA AGC TGC ATT GCG AAC CAC TAG TCG CCG               240
     TTT TTC GTG TGC ATC GCG TAT CAC GGC|ATG GGG CGT TTG ACC TCC GGG GTC GGG ACG GCG           360
                                         MET GLY ARG LEU THR SER GLY VAL GLY THR ALA
  12 GCC CTG CTA GTT GTC GCG GTG CTC CGC GTC GTC TGC GCC AAA TAC GCC TTA GCA GAC               420
     ALA LEU LEU VAL VAL ALA VAL GLY LEU ARG VAL VAL CYS ALA LYS TYR ALA LEU ALA ASP
                                 PHv5,6  ClaI
  32 CCC TCG CTT AAG ATG GCC GAT CCC AAT CGA TTT CGC GGG AAG AAC CTT CCG GTT TTG GAG          480
     PRO SER LEU LYS MET ALA ASP PRO ASN ARG PHE ARG GLY LYS ASN LEU PRO VAL LEU ASP
                                         C
  52 CAG CTG ACC GAC CCC GGG GTG CCT GTT AAG CGT GTT CAC ATT CAG CCG AGC CTG GAG GAC          540
     GLN LEU THR ASP PRO PRO GLY VAL LYS ARG VAL HIS ILE GLN PRO SER LEU GLU ASP
  72 CCG TTC CAG CCC AGC ATC ACT GTG TAC TAC GTG GTG CTG GAA CGT GTC TGC                      600
     PRO PHE GLN PRO SER ILE THR VAL TYR TYR VAL VAL LEU GLU ARG ALA CYS
  92 CGC AGC GTG CTC CTA CAT GCC CCA TCG GAG GCC CCC CAG ATC GTG CGC GGG GCT TCG GAC          660
     ARG SER VAL LEU LEU HIS ALA PRO SER GLU ALA PRO GLN ILE VAL ARG GLY ALA SER ASP
 112 GAG GCC CGA CAA ACG CAC ACG TAC AAC CTG GAA TAC ACC ATC GCC TGG TAT CGC ATG GGA GAC AAT TGC   720
     GLU ALA ARG GLN THR HIS THR TYR ASN LEU GLU TYR THR ILE ALA TRP TYR ARG MET GLY ASP ASN CYS
 132 GCT ATC CCC ATC GTT ATG GAA TAC ACC GAG TGC CCC TAC AAC AAG TCG TTG GGG GTC              780
     ALA ILE PRO ILE VAL MET GLU TYR THR GLU CYS PRO TYR ASN LYS SER LEU GLY VAL
 152 TGC CCC ATC CGA ACG CAG CCC CGC TGG AGC TAC TAT GAC TTT AGC GCC GTC AGC GAG              840
     CYS PRO ILE ARG THR GLN PRO ARG TRP SER TYR TYR ASP PHE SER ALA VAL SER GLU
                                                       C
 172 GAT AAC CTG GGA TTC CTG ATG CAC GCC CCC GCC TTC GAG ACC GCG|ACG|TAC CTG CGG              900
     ASP ASN LEU GLY PHE LEU MET HIS ALA PRO ALA PHE GLU THR ALA GLY THR TYR LEU ARG
 192 CTA GTG AAG ATA AAC GAC GAG TGG ACG GAG ATC TTT ATC CTG GAG CAC CGG GCC CGC              960
     LEU VAL LYS ILE ASN ASP GLU TRP THR GLU ILE PHE ILE LEU GLU HIS ARG ALA ARG
```

FIG. 12 CONT

```
212  GCC TCC TGC AAG TAC GCT CTC CCC CTG CGC ATC CCC CCG GCA GCG TGC CTC ACC TCG AAG   1020
     ALA SER CYS LYS TYR ALA LEU PRO LEU ARG ILE PRO PRO ALA ALA CYS LEU THR SER LYS

232  GCC TAC CAA CAG GGC GTG ACG GTC GAC AGC ATC GGG ATG TTA CCC CGC TTT ATC CCC GAA   1080
     ALA TYR GLN GLN GLY VAL THR VAL ASP SER ILE GLY MET LEU PRO ARG PHE ILE PRO GLU

252  AAC CAG CGC ACC GTC GCC CTA TAC CTA AGC TTA AAA ATC GCC GGG TGG CAC CCC AAG CCC   1140
     ASN GLN ARG THR VAL ALA LEU TYR LEU SER LEU LYS ILE ALA GLY TRP HIS PRO LYS PRO

272  CCG TAC ACC AGC CTG ACC CTG CCG GAG CTG TCC GAC CTG ACC ACC AAC GCC ACG CAA CCC   1200
     PRO TYR THR SER LEU THR LEU PRO GLU LEU SER ASP LEU THR THR ASN ALA THR GLN PRO
                                                                 BamHI
292  GAA CTC GTT CCG GAA GAC GAG CCC CTC GCC TCG CTC TTA GAG GAT CCC GCC GGG ACG GTG   1260
     GLU LEU VAL PRO GLU ASP GLU PRO LEU ALA SER LEU LEU GLU ASP PRO ALA GLY THR VAL

312  TCT TCG CAG ATC CCC CCA AAC TGG TGG CAC ATC CCG TCG ATC CAG GAC GTC GCG CAC CAC   1320
     SER SER GLN ILE PRO PRO ASN TRP TRP HIS ILE PRO SER ILE GLN ASP VAL ALA PRO HIS

332  GCC CCC GCC GCC CCC AGC AAC CCG GGC GTG CTG ATC ATC GGC GCG CTG GCC GGC AGT ACC CTG   1380
     ALA PRO ALA ALA PRO SER ASN PRO GLY LEU ILE ILE GLY ALA LEU ALA GLY SER THR LEU

352  GCG GCG CTG GTC GTC GGT ATT GCG TTT TGG GTA CGC GCC ATG ATG GCC ATG GCC CCC   1440
     ALA ALA LEU VAL VAL GLY ILE ALA PHE TRP VAL ARG ALA ARG ALA GLN MET ALA PRO

372  AAG CGC CTA CGT CTC CCC CAC ATC CGG GAT GAC ASP GCG CCC TCG CAC CAG TTG   1500
     LYS ARG LEU ARG LEU PRO HIS ILE ARG ASP ASP ALA PRO SER HIS GLN LEU

392  TTT TAC TAG AGG AGT TTC CCC GTT CCC ACT CCG CAT AAA GGG AGT CTC GAA GGA GGG TGG CCG   1560
     PHE TYR ***

GGG TAT TTG GGT GGG ACT TGG ACT CCG CAT AAA GGG AGT CTC GAA GGA GGG AAA CTA GGA   1620

CAG TTC ATA GGC CGG GAG CGT GGG GCG GCG ACC TCC CGA TCC CGA TTA GCC ACC GCG CCC   1680

ACA GCC ACC TCG ACC                                                                1740
```

FIG. 13

```
       SIGNAL
gD-1  |MGGTAARLGAVILFVVIVGLHGVRG|KYALADASLKMADPNRFRGKDLPVLDQLTDPPGVRR    61
gD-2  --RLTSGV-TAA-L--A---RV-CA------------------P------N----------K gD-1  VYHIQAGLPDPFQPPSLPITVYYAVLERACRSVLLNAPSEAPQIVRGASEDVRKQPYNLTI       122
gD-2  -----PS-E-------------------------H----------------DEA--HT-- gD-1  AWFRMGGNCAIPITVMEYTECSYNKSLGACPIRTQPRWNYYDSFSAVSEDNLGFLMHAPAF       183
gD-2  ---Y---D--------------------------------S--V----------------- gD-1  ETAGTYLRLRLVKINDWTEITQFILEHRAKGSCKYALPLRIPPSACLSPQAYQQGVTVDSIGM     244
gD-2  ---------------------------------RA----------A---TSK---------- gD-1  LPRFIPENQRTVAVYSLKIAGWHGPKAPYTSTLLPPELSETPNATQPELAPEDPEDSALLE      305
gD-2  -----------------------------------------L-------D-T-----V----

TRANSMEMBRANE
gD-1  DPVGTVAPQIPPNWHIPSIQDAATPYHPPATPNN|MGLIAGAVGGSLLAALVICGIVYWM|IR    366
gD-2  --A--SS--------------V-*-H-A--A-S-|P----I--LA--T------G--AF-V|R- gD-1  RTRKAPKRIRLPHIREDDQPSSHQPLFY                                        394
gD-2  -AQM-----L------D--A--P-----
```

PRODUCTION OF HERPES SIMPLEX VIRAL PORTEINS

The present application is a continuation-in-part of applicant's prior copending U.S. application Ser. No. 436,368 filed Oct. 25, 1982 which is a continuation-in-part of application Ser. No. 400,028 filed July 20, 1982, both of which are incorporated by reference herein.

TABLE OF CONTENTS

1. Field of the Invention
2. Background of the Invention
   2.1. Recombinant DNA Technology and Gene Expression
   2.2. Vaccines
   2.3. Herpes Viruses
3. Summary of the Invention
4. Description of the Figures
5. Description of the Invention
   5.1. Identification and Isolation of HSV Glycoprotein Genes
   5.2. Insertion of the HSV Glycoprotein Gene into a Cloning Expression Vector
   5.3. Preparation of Fusion Proteins
   5.4. Identification of the Gene Product
   5.5. Purification of the Gene Product
   5.6. Preparation of Unfused gD Protein
   5.7. Formulation of a Vaccine
6. Example: HSV-1 gD
   6.1. General Procedures Used for Preparation of the Plasmids
      6.1.1. Plasmid DNA Isolation
      6.1.2. Conditions for Restriction Enzyme Digestions
      6.1.3. Restriction Enzyme Buffers
      6.1.4. Modification of DNA
      6.1.5. DNA Polymerase Reaction
      6.1.6. Gel Purification of DNA Fragments
      6.1.7. DNA Ligation
   6.2. Localization and Isolation of the gD-1 Gene
      6.2.1. Recombinant DNA Plasmids Containing Defined Portions of the Us Region of HSV-1
      6.2.2. Localization of gD-1 Specific mRNA Coding Sequence
      6.2.3. Characterization of the gD-1 mRNA
   6.3 Cloning and Expression of the gD-1 Gene
      6.3.1. The Expression Vector pJS413
      6.3.2. Insertion of the gD-1 Gene into pJS413
      6.3.3. Identification of Transformants that Express the gD-1 Gene
   6.4. Preparation of pEH4-2 which Directs the Production of a Cro/gD-1/β-Galactosidase Fusion Protein
      6.4.1. pEH4-2 Fusion Protein Immunoreacts with Anti-HSV-1 sera
      6.4.2. Antisera Directed Against pEH4-2 Fusion Protein Immunoprecipitates HSV-1 and HSV-2 Proteins
      6.4.3. Antisera Directed Against pEH4-2 Neutralizes HSV-1 and HSV-2 Infection In Vitro
      6.4.4. Reconstruction of the gD-1 Gene in pEH4-2
   6.5. Preparation of pEH90-10am LE392 which Directs the Production of Both Cro/gD-1 and Cro/gD-1/β-galactosidase Fusion Protein
      6.5.1. Preparation of the pEH90-N Series
      6.5.2. Preparation of pEH90-10am
      6.5.3. pEH 90-10am Transformants
      6.5.4. Analysis of Proteins produced by pEH90-10am LE392 Transformants
7. EXAMPLE: HSV-2 gD
   7.1. General Procedures Used for Preparation of the Plasmids
      7.1.1. Restriction Enzyme Buffers
   7.2. Localization and Isolation of the gD-2 Gene
      7.2.1. Construction of pHV1 Containing the gD-2 Gene
      7.2.2. Localization of gD-2 Specific mRNA Coding Sequence
      7.2.3. Characterization of the gD-2 mRNA Coding Sequence
   7.3. Cloning and Expression of the gD-2 Gene
      7.3.1. Construction of pHV5
      7.3.2. Identification of Transformants That Express the gD-2 Gene
   7.4. Preparation of pHV6 which Directs the Production of a Cro/gD-2/β-Galactosidase Fusion Protein
      7.4.1. Construction of pHV6
      7.4.2. Immunoprecipitation Analysis of Antisera Directed Against pHV6 Fusion Protein
      7.4.3. Herpes Simplex Virus Neutralization In Vitro
      7.4.4. Immunofluorescense Analysis of Antisera Directed Against pHV6 Fusion Protein
8. Example: Vaccination
   8.1. Protection Against HSV-2 Infection In Vivo Using gD-1 Fusion Protein in a Vaccine Formulation
   8.2. Protection Against HSV-2 Infection In Vivo Using gD-2 Fusion Protein in a Vaccine Formulation
   8.3. Comparison of Vaccine Formulations
9. Deposit of Mircroorganisms

1. FIELD OF THE INVENTION

This invention is directed to processes for the production of proteins related to any of the Herpes Simplex Virus (HSV) glycoproteins, and to processes and compositions for making and using novel DNA sequences, plasmids and microorganisms (both eucaryotic and procaryotic) to produce such proteins.

The present invention utilizes recombinant DNA techniques to insert a DNA sequence coding for glycoprotein D (gD), or a portion thereof, into a DNA vector, such as viral DNA, plasmid DNA or bacteriophage DNA, such that the vector is capable of replicating and directing expression of the gD gene in a bacterial host or other single cell system. The resulting recombinant DNA molecule is introduced into host cells to enable production of gD, or a portion or molecular variant thereof, by the host cells. The protein produced is then isolated, purified and modified for use as an immunogen in a vaccine against infection of both HSV type 1 (HSV-1) and type 2 (HSV-2).

2. BACKGROUND OF THE INVENTION

2.1. Recombinant DNA Technology and Gene Expression

Recombinant DNA technology involves insertion of specific DNA sequences into a DNA vehicle (vector) to form a recombinant DNA molecule which is capable of replication in a host cell. Generally, the inserted DNA sequence is foreign to the recipient DNA vehicle, i.e., the inserted DNA sequence and the DNA vector are derived from organisms which do not exchange genetic information in nature, or the inserted DNA sequence may be wholly or partially synthetically made. In recent years several general methods have been developed which enable construction of recombinant DNA molecules. For example, U.S. Pat. No. 4,237,224 to Cohen and Boyer describes production of such recombinant plasmids using restriction enzymes and methods known as ligation. These recombinant plasmids are then introduced and replicated in unicellular organisms by means of transformation. Because of the general applicability of the techniques described therein, U.S. Pat. No. 4,237,224 is hereby incorporated by reference into the present specification.

Another method for introducing recombinant DNA molecules into unicellular organisms is described by Collins and Hohn in U.S. Pat. No. 4,304,863 which is also incorporated herein by reference. This method utilizes a packaging/transduction system with bacteriophage vectors.

Regardless of the method used for construction, the recombinant DNA molecule must be compatible with the host cell, i.e., capable of autonomous replication in the host cell. The recombinant DNA molecule should also have a marker function which allows the selection of host cells so transformed by the recombinant DNA molecule. In addition, if all of the proper replication, transcription and translation signals are correctly arranged on the plasmid, the foreign gene will be properly expressed in the transformed cells and their progeny.

As is characteristic of all viruses which infect eucaryotic cells, Herpes Simplex Virus requires a eucaryotic host cell system in which to replicate its genome, express its viral genes and generate its progeny. The signals and control elements for DNA replication, gene expression and virus assembly in eucaryotes differ from those of procaryotes. This is of critical importance when attempts are made to express in procaryotic host cells a gene which is naturally expressed only in eucaryotic cells.

These different genetic signals and processing events control many levels of gene expression, for instance, DNA transcription and messenger RNA translation. Transcription of DNA is dependent upon the presence of a promoter which is a DNA sequence that directs the binding of RNA polymerase and thereby promotes transcription. The DNA sequences of eucaryotic promoters differ from those of procaryotic promoters. Furthermore, eucaryotic promoters and accompanying genetic signals may not be recognized in or may not function in a procaryotic system.

Similarly, translation of messenger RNA (mRNA) in procaryotes depends upon the presence of the proper procaryotic signals which differ from those of eucaryotes. Efficient translation of mRNA in procaryotes requires a ribosome binding site called the Shine Dlgarno (SD) sequence on the mRNA. This sequence is a short nucleotide sequence of mRNA that is located before the start codon (AUG) which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, 1979, Methods in Enzymology 68: 473.

Many factors complicate the expression of eucaryotic genes in procaryotes even after the proper signals are inserted and appropriately positioned. A clear understanding of the nature of these factors and the mechanisms by which they operate is presently lacking. One such factor is the presence of an active proteolytic system in $E.$ $coli$ and other bacteria. This protein-degrading system appears to selectively destroy "abnormal" or foreign proteins such as eucaryotic proteins. A tremendous utility, therefore, would be afforded by the development of a means to protect eucaryotic proteins expressed in bacteria from proteolytic degradation. One strategy is to construct hybrid genes in which the eucaryotic sequence is ligated in phase (i.e., in the correct reading frame) with a procaryotic gene resulting in a fusion protein product (a protein that is a hybrid of procaryotic and foreign or eucaryotic amino acid sequences).

Construction of hybrid genes was the approach used in the molecular cloning of genes encoding a number of eucaryotic proteins, such as somatostatin, rat proinsulin, growth hormone, and ovalbumin-like protein. Additionally, procaryotic promoters have been ligated to such fusion gene sequences in the case of ovalbumin and $\beta$-globin (Guarente et al., 1980, Cell 20: 543). The Guarente et al. system involves inserting the lac promoter, including the SD sequence, at varying distances in front of the ATG of the fusion gene. Although the molecular cloning and expression of several eucaryotic genes has been accomplished, this has not heretofore been done for the gD gene. Nor is the state of the art such that expression of foreign or eucaryotic genes in procaryotic host cells may be routinely performed.

2.2. Vaccines

There are three basic approaches to the control and therapy of viral infections: (1) vaccines that elicit an active immune response; (2) chemotherapeutic agents that inhibit viral replication; and (3) agents that induce the synthesis of interferon. All three can be used to prevent infection, but are more effective when applied early in infection. Vaccination, or active immunization is usually ineffective after infection has begun.

Vaccines are usually prepared by rendering a virus harmless without destroying its immunological properties. Traditionally this is accomplished either by inactivating the infectivity of the virus (i.e., "killing" the virus, usually by treatment with various chemical agents such as formaldehyde) for use in inactivated vaccines, or by selecting an avirulent or attenuated (modified) virus for use in live vaccines (attenuated vaccines). Attenuation is obtained by adapting the virus to unusual conditions (to different animal hosts and cell cultures) and by frequent passages of large viral inocula to select mutants which have lost virulence and thus produce no symptoms or merely minor symptoms. A few vaccines still used in veterinary practice consist of fully virulent infectious virus injected in a site where viral multiplication is of little consequence. This procedure has been considered too dangerous for use in man.

Attenuated virus used in live vaccines are generally excellent immunogens because the attenuated virus multiplies in the host thus eliciting long-lasting immunity. Attenuated vaccines induce humoral antibodies directed against all viral antigens, both surface and internal antigens of the virion. However, a number of problems are encountered with the use of live vaccines, such as insufficient attenuation of the virus, genetic instability of the virus, contamination by advantitious viruses in cell cultures used to grow the vaccine virus, and finally instability of the vaccine (e.g., heat-labile).

While the use of inactivated vaccines (employing "killed" or inactivated virus that does not multiply) avoids the difficulties encountered with the use of live vaccines, killed viruses do not multiply in the immunized animal and usually produce antibodies directed against only surface components. The major difficulty with inactivated vaccines, however, lies in producing enough virus to provide the necessary quantity of relevant antigen. Other difficulties encountered with the use of inactivated vaccines are that the immunity achieved is brief and often requires additional immunizations, the antigenic sites may be altered by the inactivating chemical treatment and, thus, be less immunogenic or may induce antibodies that are less effective at neutralizing viral infections, and the vaccines frequently do not induce satisfactory levels of IgA.

Subunit vaccines contain only the necessary and relevant immunogenic material, such as the capsid proteins of nonenveloped icosahedral viruses or the peplomers (glycoprotein spikes) of enveloped viruses. Subunit vaccines can be made by isolating the relevant subunit from highly purified viral fractions, or by synthesizing the relevant polypeptide. A major advantage of subunit vaccines is the exclusion of genetic material of viral origin and of host- or donor-derived interfering substances. However, at present, production of subunit vaccines using these methods is too expensive for widespread commercial use. Recombinant DNA technology has much to offer in the production of subunit vaccines; the molecular cloning and host cell expression of viral genes which encode the relevant immunogenic portions of the virus or its proteins can produce sufficient quantities of the relevant immunogen for use in a subunit vaccine.

Vaccines are often administered in an emulsion with various adjuvants. The adjuvants aid in attaining a more durable and higher level of immunity using smaller amounts of antigen in fewer doses than if the immunogen were administered alone. The mechanism of adjuvant action is complex and not completely understood. However, it may involve the stimulation of phagocytosis and other activities of the reticuloendothelial system as well as a delayed release and degradation of the antigen. Examples of adjuvants include Freund's adjuvant (complete or incomplete), Adjuvant 65 (containing peanut oil, mannide monooleate and aluminum monostearate), and mineral gels such as aluminum hydroxide, aluminum phosphate, or alum. Freund's adjuvant is no longer used in vaccine formulations for humans or for food animals because it contains nonmetabolizable mineral oil and is a potential carcinogen; however, the mineral gels are widely used in commercial veterinary vaccines.

2.3. Herpes Viruses

Herpes viruses (Herpetoviridae) are large DNA viruses that are notable for establishing latent infections which may persist for the life of the host. After primary infection, which may be inapparent, the virus remains quiescent until it is reactivated by any of several suspected stimuli such as irradiation or immunosuppression.

The active state, or acute form of infection, is characterized by a productive or lytic infection, i.e., the virus is replicating, taking over the host cell machinery, producing mature infectious virions and causing cell death. In the latent state, however, the virus is established in the ganglia of the host; there is little evidence of production of infectious virus during latency.

Most primary infections occur during childhood and may be inapparent. Infection can result from viral inoculation of a mucous membrane or from the introduction of virus into the skin via a break in the epidermal surface. Thus, the infectious virus can be transmitted by close contact. Once acquired, HSV is retained in the body for life and the victim is subject to recurrent attacks which may be asymptomatic or result in a number of clinical manifestations such as mucocutaneous diseases including herpes labialis (lesions on the lip commonly called "fever blisters" or "cold sores"), gingivostomatitis (the mouth and gums become covered with vesicles that rupture and become ulcers), pharyngitis, tonsillitis, keratoconjunctivitis (keratitis or inflammation of the cornea of the eye which progresses to a dendritic ulcer which may ultimately lead to corneal scarring resulting in blindness) and gential herpes. Less commonly, HSV infection can cause encephalitis, eczema herpeticum, traumatic herpes, hepatitis and neonatal herpes.

During active outbreaks, infectious virus can be isolated from the lesions or from surrounding fluids, e.g., from saliva in the case of herpes labialis. These lesions, which tend to break out on the same part of the body of any given individual, are provoked by a number of stimuli such as menstruation, excessive exposure to sunlight or cold wind, pituitary or adrenal hormones, allergic reactions, or classically, fever. During such outbreaks the victims shed virus and can spread infectious virus to others via contact.

During the latent stage of infection, investigators have demonstrated that the virus harbors in an area other than that in which lesions subsequently form. During this quiescent stage the virus has been localized in the neurons of sensory ganglia (in the case of facial lesions, the trigeminal ganglion is commonly involved) and cannot be isolated from the usual affected area.

Although most children recover rapidly from primary infection, occasionally, disseminated neonatal herpes infection characterized by hepatitis overwhelms the affected newborn baby. Most fatal infections are acquired at birth from infectious attendants or, more commonly, from an infectious mother when a baby encounters genital herpes in the mother's birth canal. Vulvovaginitis in women and children as well as infections of the penis were previously thought to be caused by HSV-2, however, recent results indicate that either HSV-1 or HSV-2 can be the causative agent; in addition, herpetic venereal infection in women has been associated with carcinoma of the cervix.

Herpes infection has reached epidemic proportions in today's society. At present there is no cure for HSV infections and current treatments involve the use of compounds which inhibit DNA sythesis. These compounds, of course, are non-selective in that they inhibit cellular DNA synthesis of dividing cells as well as that of virus. In addition, these compounds are useful only during active infection and, so far, have no demonstrable effect during latency.

Herpes viruses are viruses of eucaryotes and contain a linear, double-stranded DNA genome which ranges in size from $80 \times 10^6$ to $150 \times 10^6$ daltons. Each virion has an icosahedral nucleocapsid and a membrane envelope which is formed by removal from the host cellular lipid bilayer during maturation and budding. The viral envelope is a lipid bilayer that contains a number of viral specific proteins which, although partially embedded in the membrane, protrude outward from the membrane envelope. During primary infection the membrane envelope is required for the efficient penetration of the viral particle into the cell. Antibodies which specifically bind to the viral proteins on the outside of the lipid bilayer are capable of neutralizing viral infectivity. Those viral proteins which are most essential to the entry of the virus into the cell are glycoproteins (protein molecules with sugar molecules associated therewith). Herpes Simplex Virus type 1 (HSV-1) and type 2 (HSV-2) each produce at least four different glycoproteins which are antigenically distinct from one another. Certain of these proteins from HSV-1 and HSV-2 share common epitopes (i.e., antigenic sites or antibody binding sites). An example of such a protein is a 49,000–58,000 dalton glycoprotein designated gD. Polyvalent antiserum against HSV-1 gD is capable of neutralizing both HSV-1 and HSV-2 infections (Norrild, 1979, Current Topics in Microbiol. and Immunol. 19: 67).

3. SUMMARY OF THE INVENTION

Methods and compositions are provided for the cloning and expression of an HSV glycoprotein gene in single-cell host organisms. Also described are methods for culturing these novel single-cell organisms to produce the HSV gene product and methods for the purification of the gene product. The gD-related protein produced by the recombinant DNA techniques described herein may be formulated for use as an immunogen in a vaccine to protect against HSV-1 and HSV-2 infection.

The HSV-1 gD gene (isolated from HSV-1 Patton Strain) was identified in the viral genome by intertypic recombinational analysis and mRNA mapping. Once localized on a specific segment of DNA, the nucleotide sequence of the gene was determined and the amino acid sequence of the gD protein was predicted.

The HSV-2 gD gene (isolated from HSV-2 strain G) was identified in the viral genome by analogy to the location of gD in the HSV-1 genome and by hybridization analysis.

The isolated gD genes or gene fragments (type 1 or type 2) were subsequently inserted into plasmid vectors to form recombinant plasmids which serve as biologically functional replication units. These recombinant plasmids were constructed so as to facilitate both the replication and expression of the gD genes upon transformation of compatible host cells. Additionally, the plasmids provide for a one-step identification of transformed microorganisms actively expressing the gD genes. Finally, methods are described for isolating the expressed gene products and for use in formulating a vaccine.

4. DESCRIPTION OF THE FIGURES

The present invention may be more fully understood by reference to the following detailed description of the invention, examples of specific embodiments of the invention, and the appended figures in which:

FIG. 1a represents the HSV-1 genome and indicates the location of the short unique region (Us) wherein lies the gD gene of HSV-1 (hereinafter referred to as the gD-1 gene).

FIG. 1b represents a restriction map of the HSV-1 EcoRI-H fragment insert of lambda gtWES::EcoRI-H. Only the restriction sites relevant to the discussion are depicted. Restriction enzymes recognition sequences are abbreviated as follows: BamHI (Ba4 through Ba8); BglII (Bg2); BstEII (Bs); EcoRI (RI); HindIII (H3); KpnI (Kp); PvuII (Pv); SacI (Sc); SalI (Sa); and XhoI (Xh).

Figure 2:
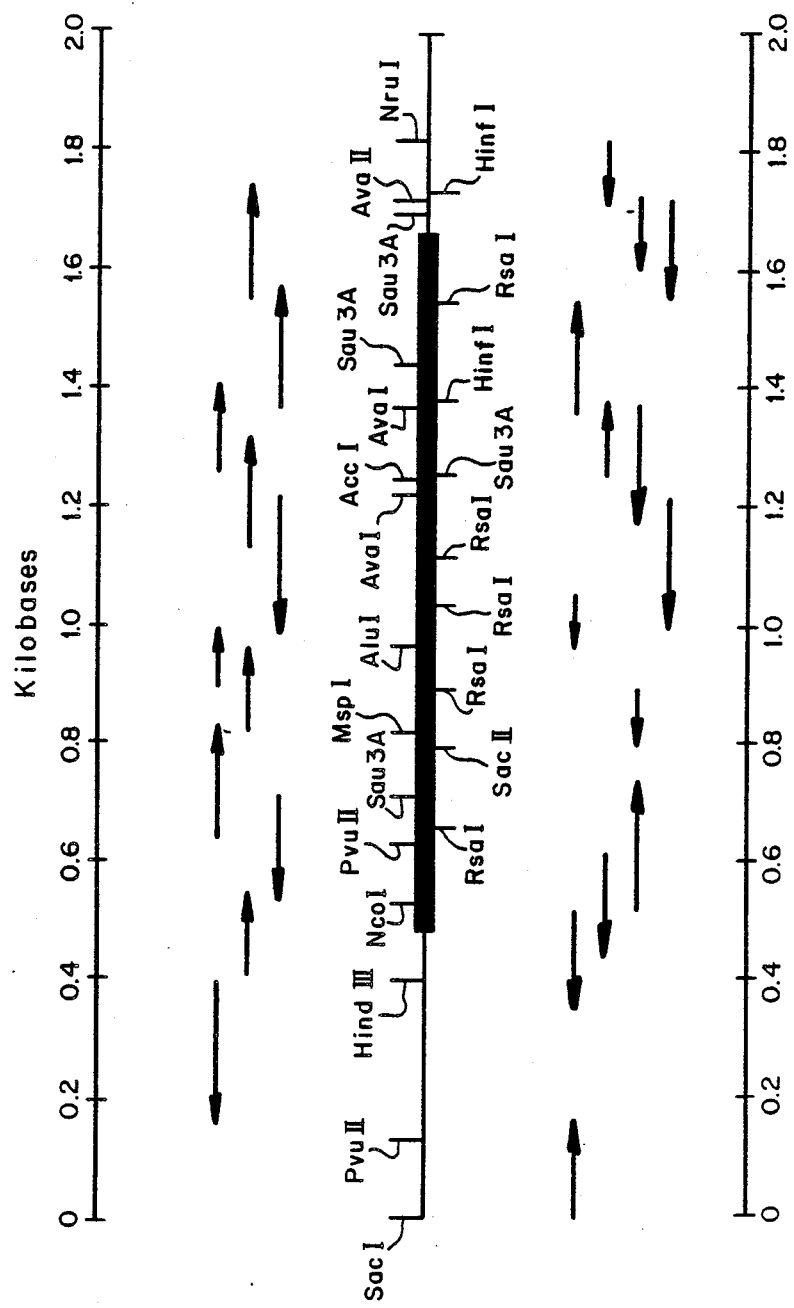

FIG. 2 represents the sequencing strategy and restriction map of the gD-1 gene sequence. The coding region is represented by a bar (broadened area) and the non-coding region by a single line. Restriction endonuclease cleavage sites used for fragment isolation, labeling and secondary digestion are indicated. Horizontal arrows represent the regions of DNA sequenced: those above the restriction map indicate that the non-coding strand sequence was determined; those below the restriction map indicate that the template strand was sequenced.

FIG. 3 represents the nucleotide sequence of the gD-1 gene and the predicted amino acid sequence of the gD-1 protein. Pertinent restriction sites are indicated and the numbered vertical arrows at the amino coding terminus of gD-1 indicate ligation sites of the gD-1 amino-coding terminus to pJS413 in the following recombinant plasmids: pEH51, pEH60, pEH62, pEH66, pEH71, pEH73 and pEH74 which contain the rest of the gD-1 sequence to its natural TAG; and pEH4-2, pEH82, pEH3-25, and the pEH90-N series which encode Cro/gD-1/β-galactosidase fusion proteins. The numbered vertical arrows at the carboxy coding terminus of gD-1 indicate ligation sites of the gD-1 carboxy coding terminus to (1) the β-galactosidase gene (z-gene) of pJS413 in the following recombinant plasmids: pEH4-2, pEH82, pEH3-25; or (2) the z-gene of pHK414 in the pEH90-N series of plasmids.

Figure 4:
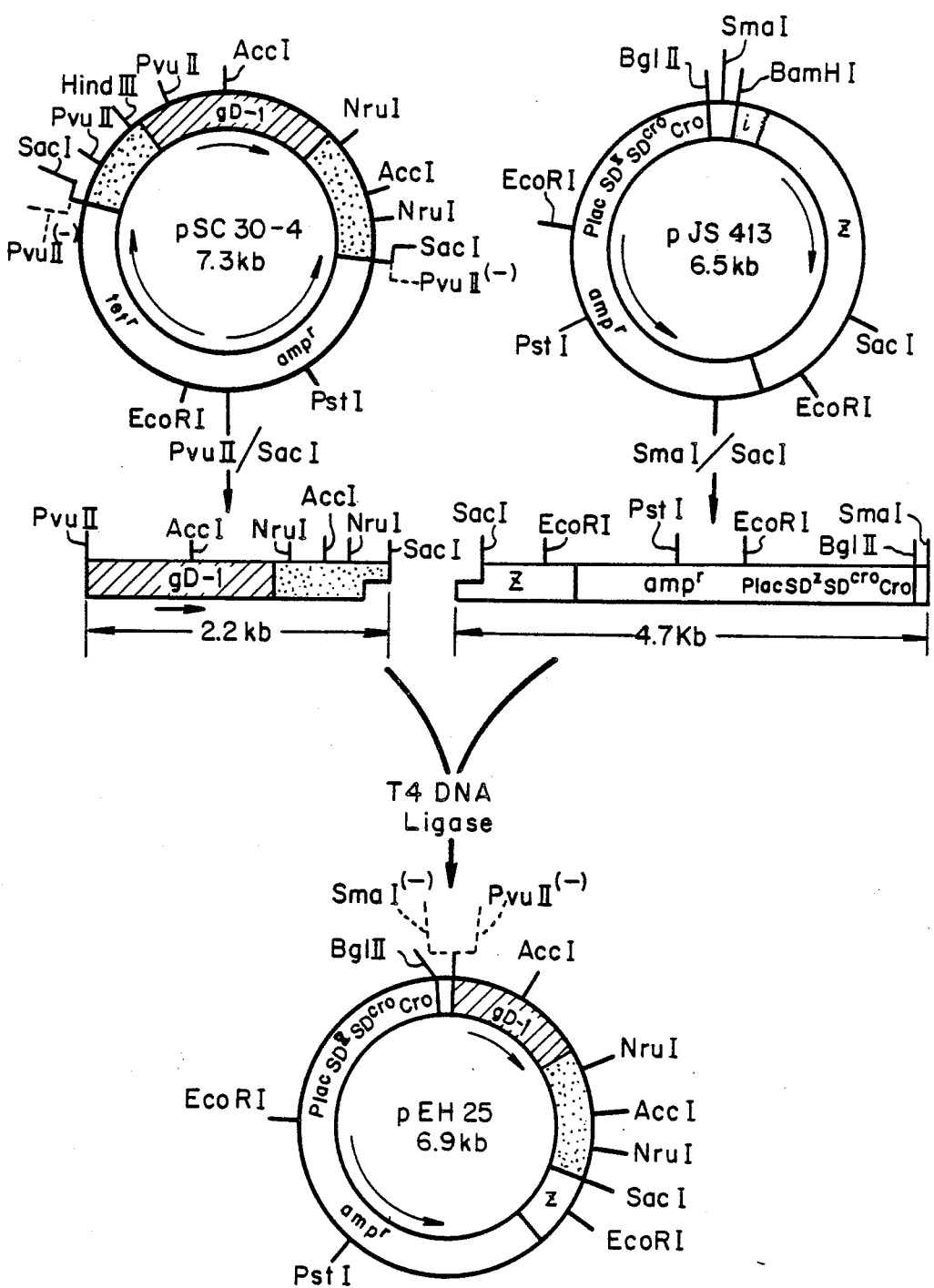

FIG. 4 (not drawn to scale) represents the construction of pEH25, a recombinant plasmid derived from a portion of the gD-1 gene, and pJS413, an expression vector for E. coli. The recombinant plasmid, pEH25, directs the production of an HSV-1 gD-related protein encoded by approximately 87% of the gD-1 coding sequence ligated to a "leader" sequence (cro) derived from the expression vector.

FIG. 5 represents the DNA sequence and predicted amino acid sequence of the Cro/gD-1 junction in pEH25.

Figure 6:
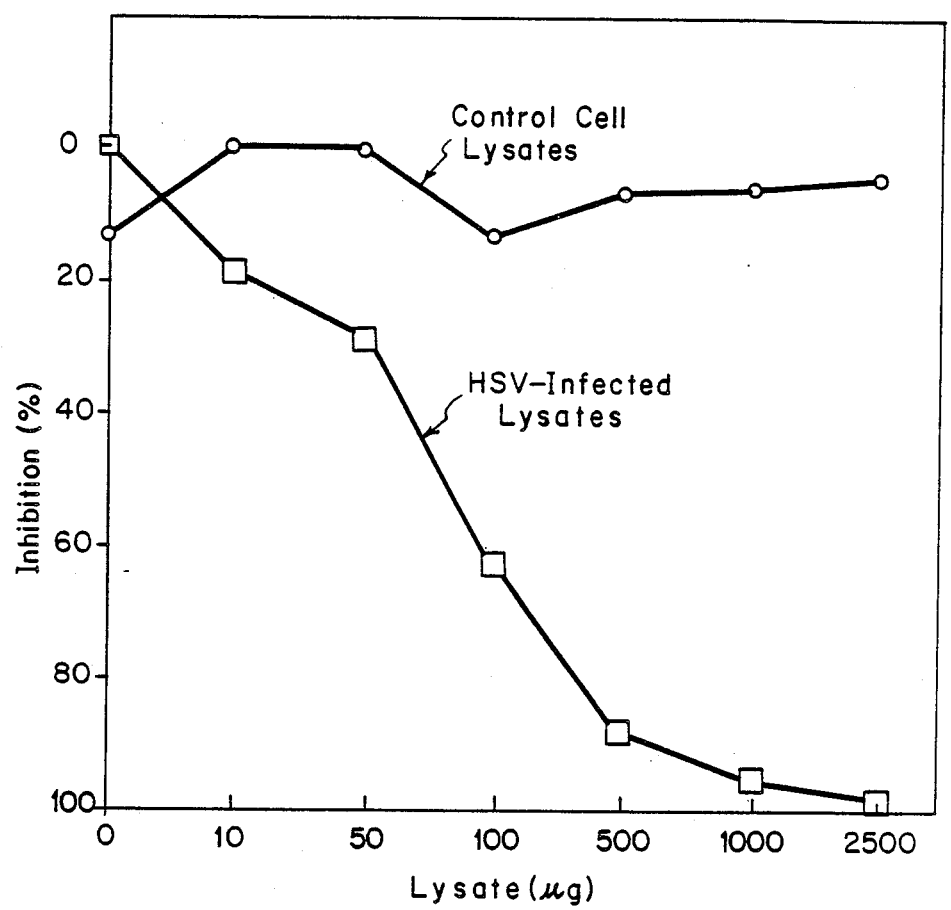

FIG. 6 represents the inhibition of immunoprecipitation of the pEH25 gD product by the addition of competing antigens present in lysates of HSV-infected Hela cells. The open circles represent lysates of uninfected Hela cells (controls); the open boxes represent lysates of the Hela cells infected with HSV-1.

Figure 7:
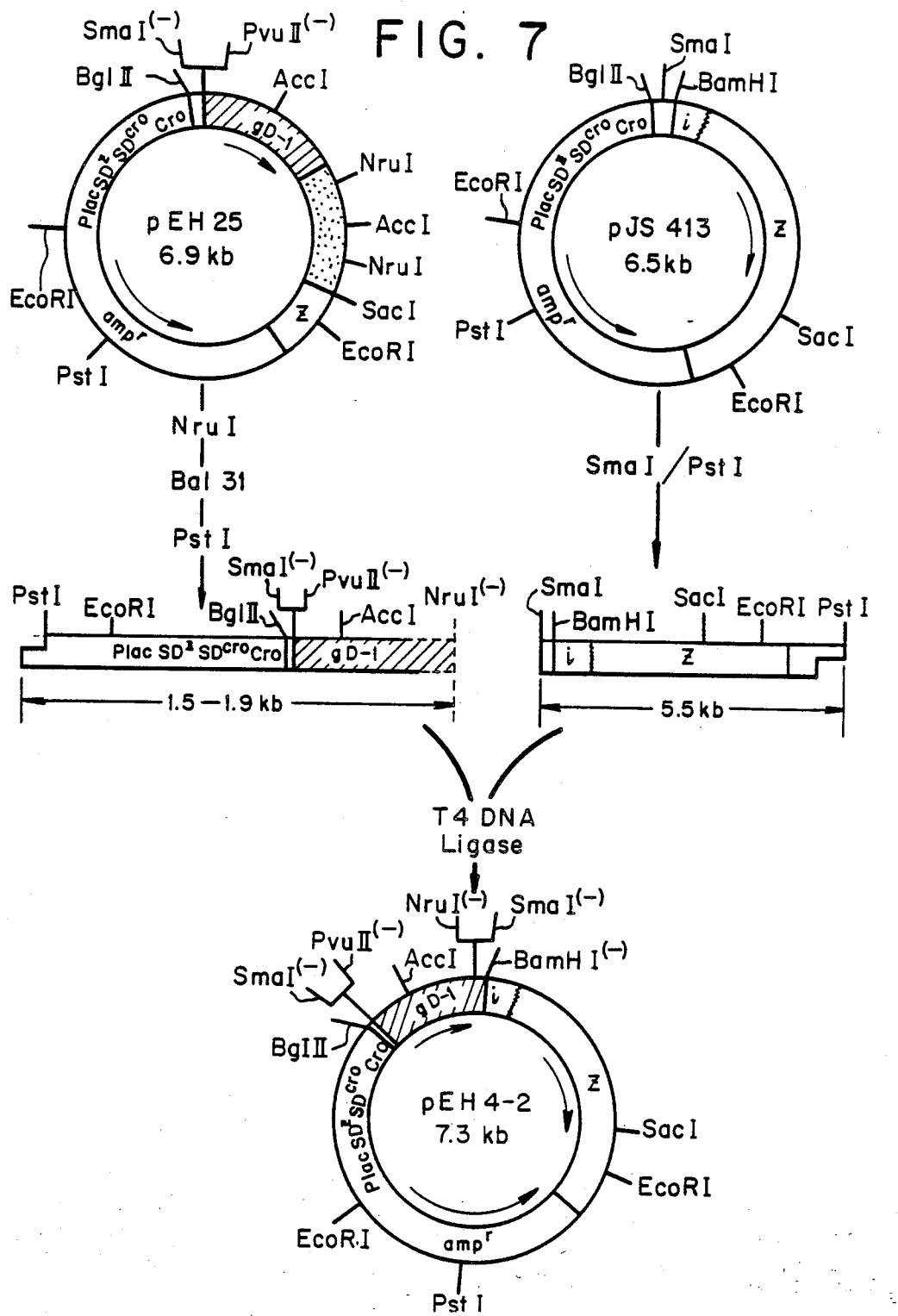

FIG. 7 (not drawn to scale) represents the construction of pEH4-2, a gD-1 expression plasmid derived from pEH25, in which 205 nucleotides (69 amino acids) of the 3'-terminus of the gD-1 coding sequence are deleted and replaced with approximately 3,000 additional nucleotides coding for the β-galactosidase protein of E. coli. This recombinant plasmid allows for the production of a "sandwich" protein (or fusion protein) with E. coli-related polypeptides (i.e., Cro and β-galactosidase) fused to each end of the gD-1 specific protein.

Figure 8:
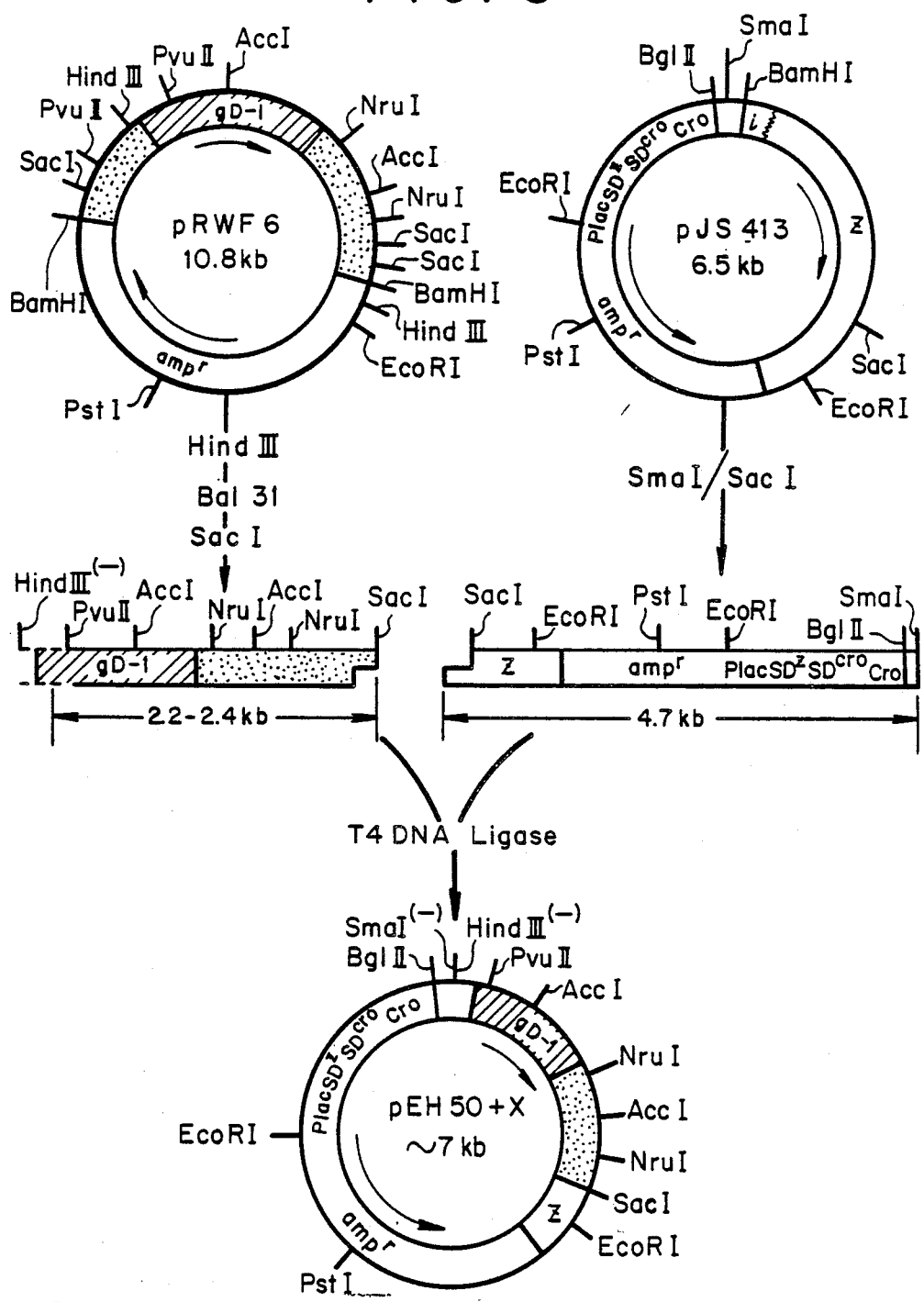

FIG. 8 (not drawn to scale) represents a method for producing a number of gD-1 expression plasmids, pEH50+x, each containing a variable portion of the amino coding terminus of the gD gene.

Figure 9:
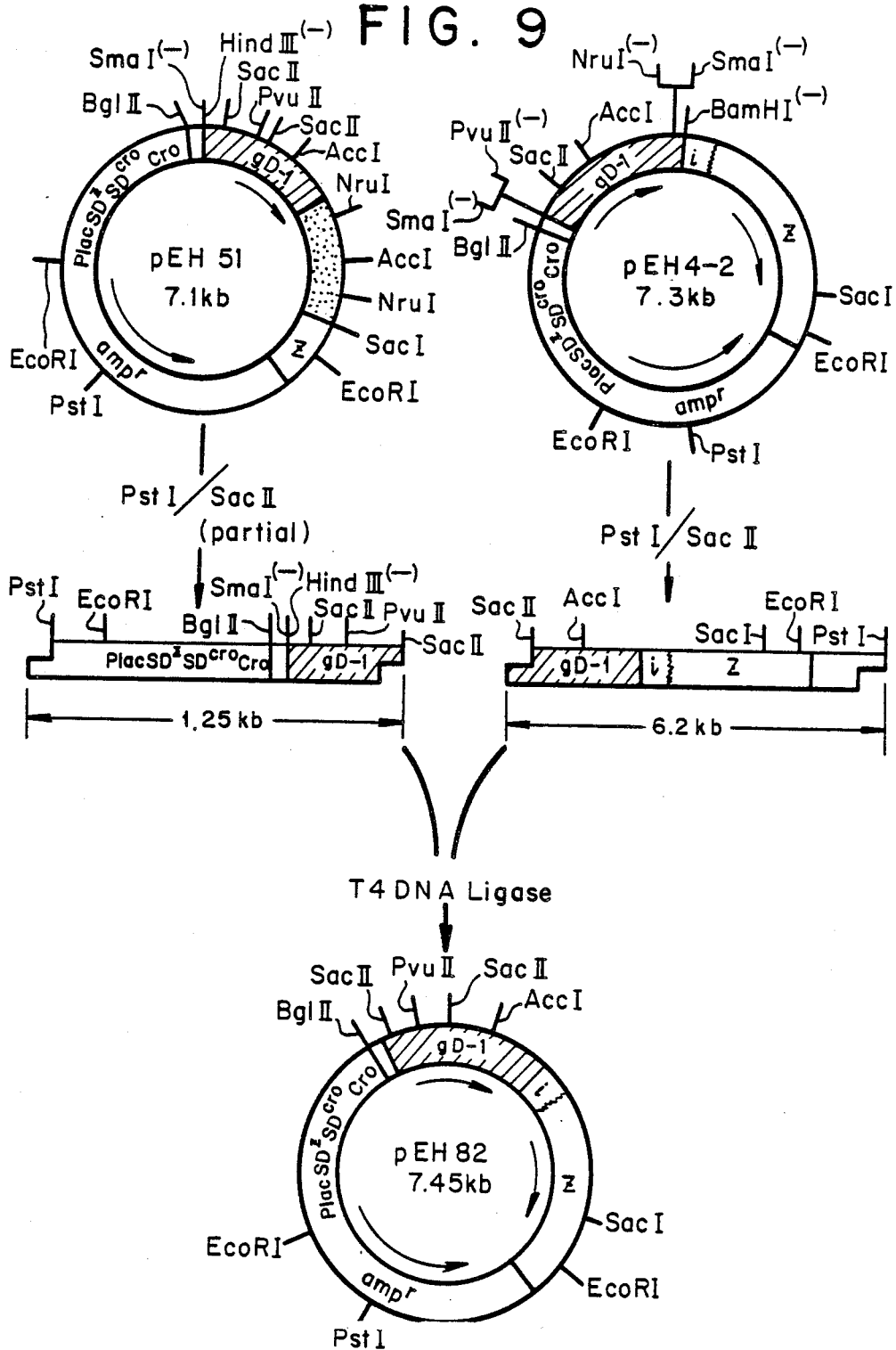

FIG. 9 (not drawn to scale) represents a method for reconstructing the amino-coding terminus of the gD-1 gene in pEH4-2 so that a gD-1 protein fused to β-galactosidase is expressed by host cells transformed with pEH82.

Figure 10A:
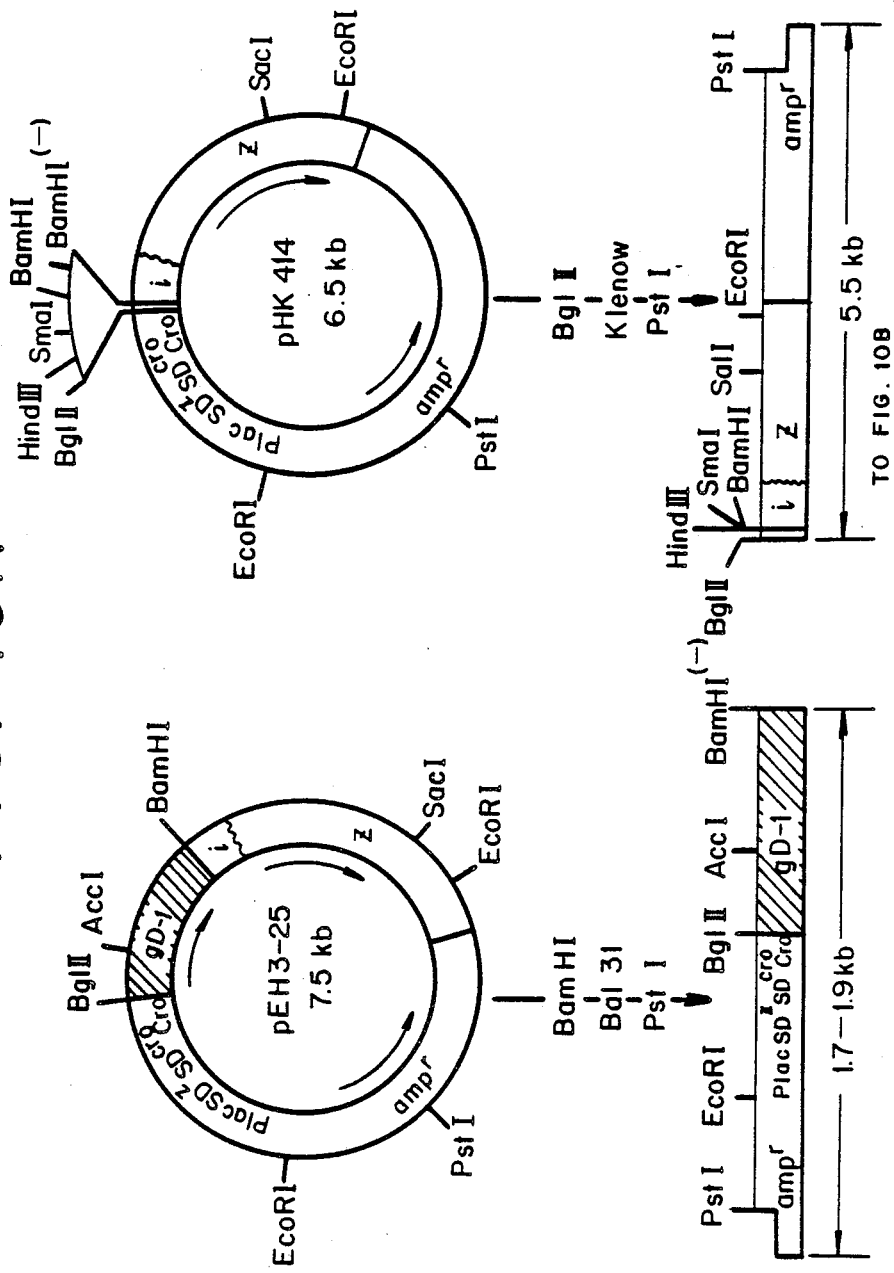
Figure 10B:
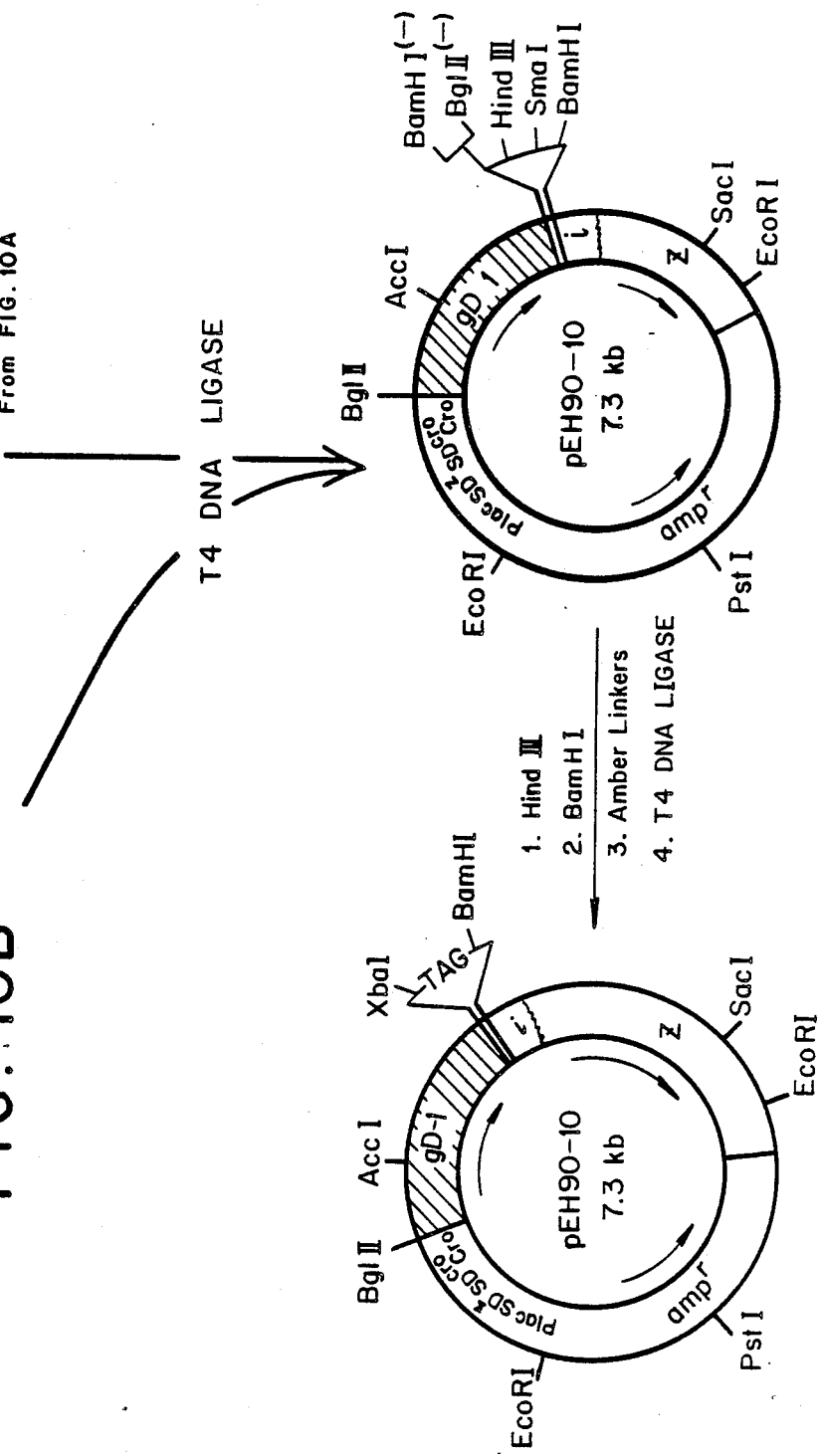

FIGS. 10a and 10b (not drawn to scale) represent the construction of pEH90-10am, a gD-1 expression plasmid derived from pEH3-25 and pHK414. The recombinant plasmid, pEH90-10am, allows for the production of gD-1 both fused and unfused to β-galactosidase in *E. coli* transformants containing amber suppressor tRNAs.

Figure 11:
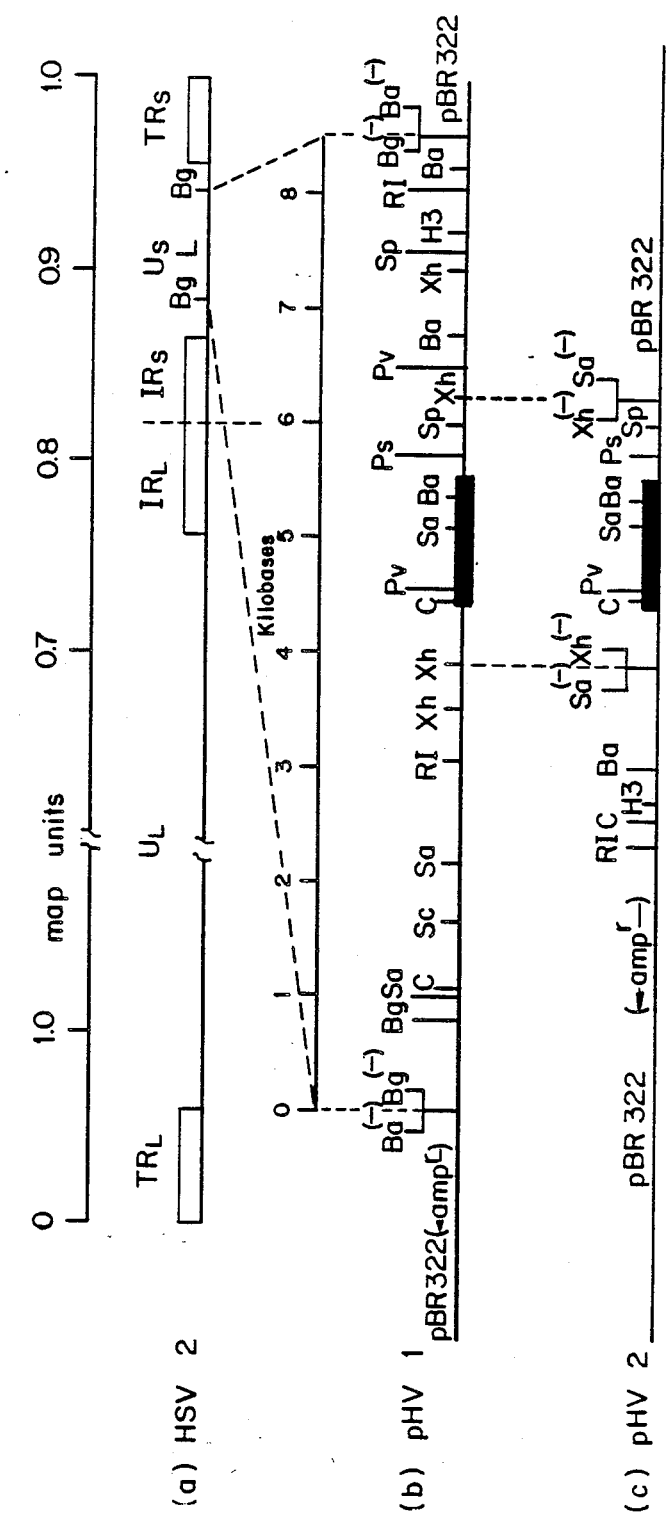

FIG. 11a represents the HSV-2 genome and indicates the location of the BglII fragment within the short unique region (Us) wherein lies the gD gene of HSV-2 (hereinafter referred to as the gD-2 gene). The BglII restriction sites which define the L fragment are indicated as Bg.

FIG. 11b represents a restriction map of the BglII L fragment insert of pHV1. Only relevant restriction endonuclease recognition sites are indicated. Restriction enzyme recognition sites are abbreviated as follows: BamHI (Ba); BglII (Bg); ClaI (C); HindIII (H3); PvuII (Pv); SalI (Sa); SacI (Sc); SphI (Sp); and XhoI (Xh). The bar (broadened area) represents the location and position of the gD-2 mRNA coding sequence.

FIG. 11c represents the restriction map of HSV-2 XhoI DNA fragment insert of pHV2.

FIG. 12 represents the nucleotide sequence of the gD-2 gene and the predicted amino acid sequence of the gD-2 protein. Pertinent restriction sites are indicated and the numbered vertical arrows at the amino coding terminus of the gD-2 gene indicate the ligation sites of the gD-2 amino coding terminus to pJS413 in recombinant plasmids pHV5 (which contains the entire carboxy coding terminus of gD-2) and pHV6. The BamHI site is the ligation site of the gD-2 carboxy coding terminus to the z-gene of pHK414 in pHV6.

FIG. 13 represents a comparison of the predicted amino acid sequences of gD-1 and gD-2. Amino acid residues are represented by the single-letter code. Amino acid residues which are homologous in gD-1 and gD-2 are indicated by dashes in the gD-2 sequence. The gD-2 sequence is one amino acid residue shorter than the gD-1 sequence. The "missing" amino acid in gD-2 is indicated by an asterisk (*).

Figure 14:
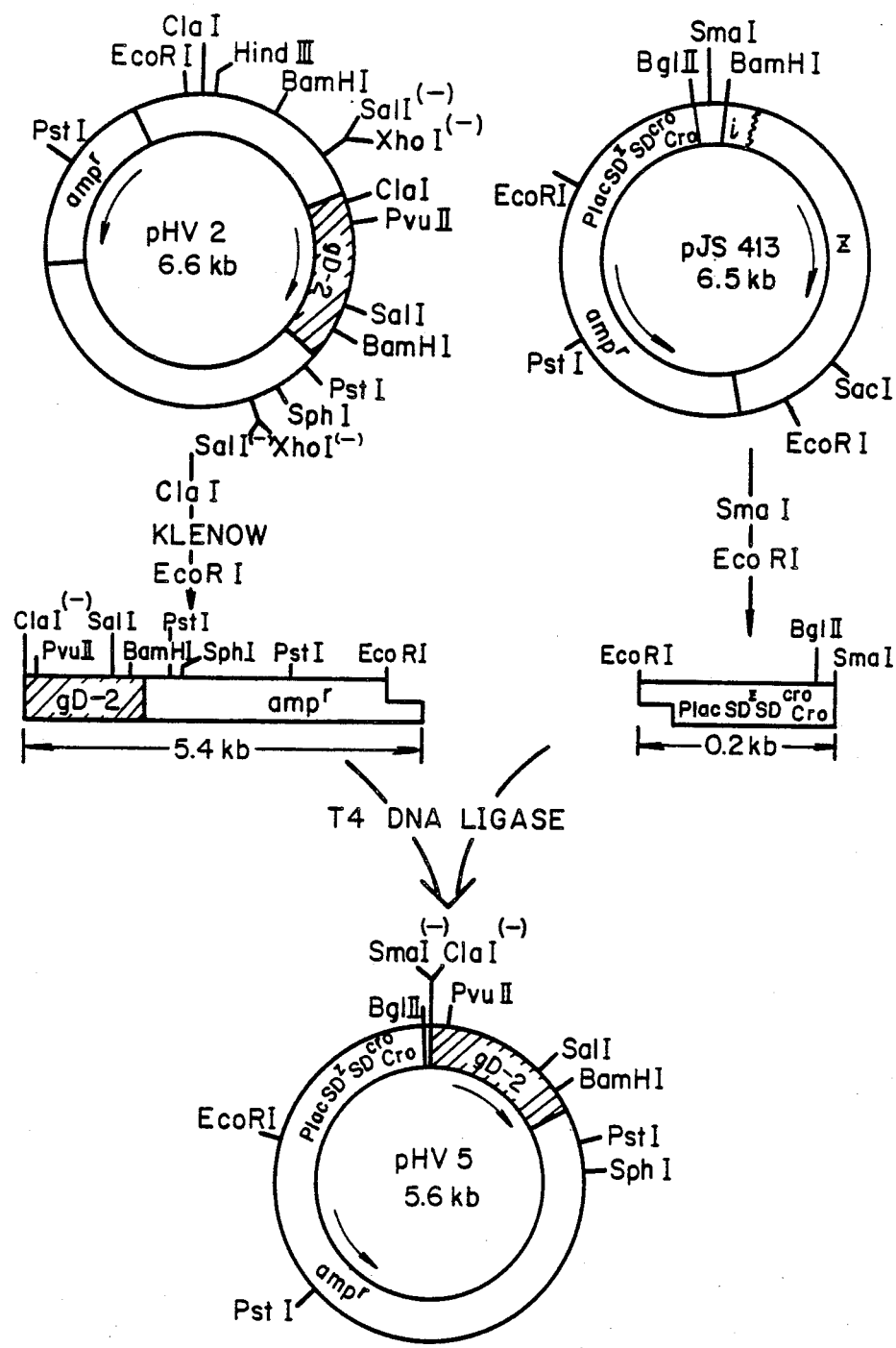

FIG. 14 (not drawn to scale) represents the construction of pHV5, a recombinant plasmid derived from a portion of the gD-2 gene and pJS413. The recombinant plasmid pHV5 directs the production of an HSV-2 gD-related protein encoded by approximately 90% of the gD-2 coding sequence ligated to a "leader" sequence (Cro) derived from the expression vector.

Figure 15A:
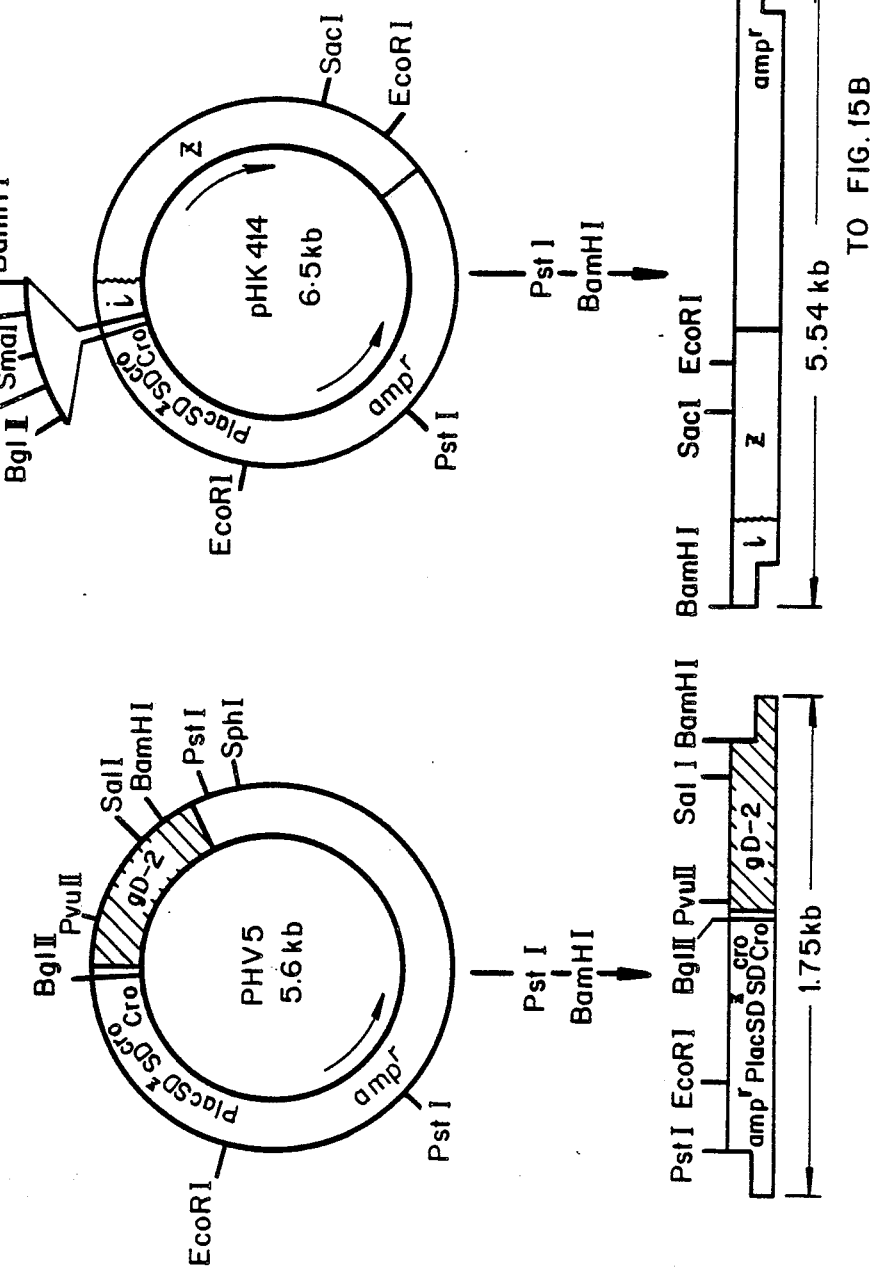
Figure 15B:
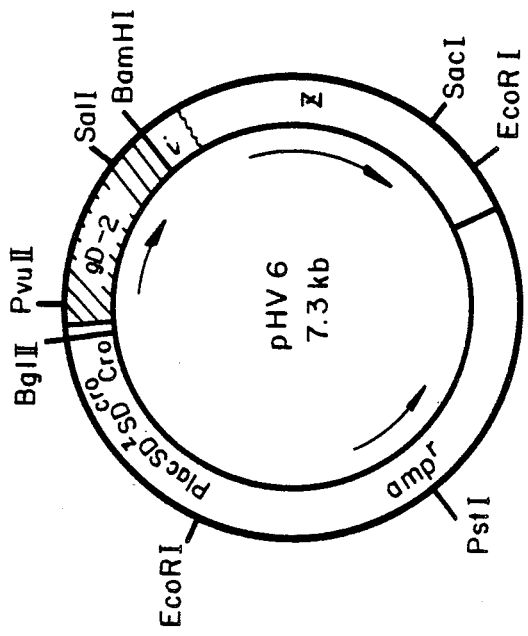

FIG. 15 represents the construction of pHV6, a gD-2 expression plasmid derived from pHV5, in which 259 nucleotides (86 amino aicds) of the 3'-terminus of the gD-2 coding sequence are deleted and replaced with approximately 3,000 additional nucleotides derived from the expression plasmid pHK414 coding for the β-galactosidase protein of *E. coli*. The recombinant plasmid, pHV6, allows for the production of a "sandwich" protein (or fusion protein) having *E. coli* related polypeptides (i.e., Cro and β-galactosidase) fused to each end of the gD-2 specific protein.

5. DESCRIPTION OF THE INVENTION

This invention relates to the use of recombinant DNA techniques to produce polypeptides related to HSV proteins which can be used as immunogens in vaccine formulations. More specifically, the production of gD-related proteins is described. Since polyvalent antiserum directed against HSV-1 gD is capable of neutralizing both HSV-1 and HSV-2, the pure gD protein, or any antigenically significant portion thereof, may be used in a subunit vaccine which would efficiently protect the recipient from both HSV-1 and HSV-2 primary infections.

The recombinant plasmids, constructed as described herein, provide for host cell production of a protein which is a gD-related polypeptide and which is stable and resistant to host cell degradation; such plasmids enable the generation of large quantities of a gD-related protein or fusion protein containing immunological and antigenic determinants of gD. However, the DNA compositions described herein are not limited to the production of a gD-related protein and may be used to produce polypeptides related to any of the HSV proteins. It can readily be seen that various immunogens and vaccine formulations can be prepared.

The method of this invention may be divided into the following stages for the purpose of description: (1) identification and isolation of the HSV glycoprotein gene or gene fragment, (2) insertion of the gene or gene fragment into a cloning expression vector to form a recombinant DNA molecule which is used to transform single-cell organisms, (3) identification and growth of the transformed single-cell organisms which are capable of replicating and expressing the gene, (4) identification and purification of the gene product and (5) determination of the immunopotency of the gene product by assessment of its ability to elicit the production of neutralizing antibodies. For purposes of clarity the entire method will be discussed in terms of the gD gene. The same techniques, however, may be applied in an analogous fashion to similarly produce a polypeptide related to any of the HSV glycoproteins.

5.1. Identification and Isolation of HSV GLY Coprotein Genes

The HSV glycoprotein (gD) gene may be obtained from any HSV type 1 or type 2 strain. Isolation of the gD gene (or a portion thereof), involves first isolating HSV DNA; generating HSV DNA fragments; and identifying the fragments which contain the glycoprotein gene sequences. Before identification, the HSV DNA fragments are usually ligated into cloning vectors that are used to transform host cells; this enables generation of multiple copies of the HSY DNA fragments so that an ample supply is available for analysis and identification procedures.

The HSV DNA can be obtained either (1) by isolating DNA directly from virus purified from eucaryotic cells infected with the virus or (2) from bacteriophage or plasmids which contain a portion of the viral genome containing the gD gene.

In order to generate the HSV DNA fragments, the DNA may be cleaved at specific sites using restriction enzymes; alternatively, one can use DNase in the presence of manganese to fragment the DNA; or the DNA can be physically sheared, as, for example, by sonication. The linear DNA fragments can then be separated according to size by standard techniques, including, but not limited to, agarose and polyacrylamide gel electrophoresis and column chromatography.

Any restriction enzyme or combination of restriction enzymes may be used to generate the HSV DNA fragment containing the gD sequence provided the enzymes do not destroy the immunopotency of the gD gene product. For example, an antigenic site of a protein can consist of from about 7 to about 14 amino acids. Thus, a protein of the size of gD may have many discrete antigenic sites, possibly thousands considering overlapping sequences, secondary structure considerations, and processing events such as acetylation, glycosylation or phosphorylation. Therefore, many partial gD gene sequences could code for an antigenic site. Consequently, many restriction enzyme combinations may be used to generate DNA fragments which, when inserted into an appropriate vector, are capable of directing in a single-cell organism the production of gD specific amino acid sequences comprising different antigenic determinants.

Transformation of host cells with these recombinant DNA molecules incorporating the HSV DNA fragments enable generation of multiple copies of the viral DNA which can then be analyzed to identify the fragment that contains the gD gene sequence. Insertion of HSV DNA restriction fragments into a cloning vector is easily accomplished when the cloning vector has complementary cohesive termini. However, if the complementary restriction sites used to fragment the HSV DNA are not present in the cloning vector, the ends of the HSV DNA or the cloning vector may be modified. Such modifications include producing blunt ends by digesting back single-stranded DNA termini or by filling in single-stranded termini so that the ends can be blunt end ligated. Alternatively, any site desired may be produced by ligating nucleotide sequences (linkers) onto the DNA termini; these ligated linkers may comprise specific chemically synthesized oligonucleotides encoding restriction enzyme recognition sequences. According to other methods, the cleaved vector and the HSV DNA fragment may be modified by homopolymeric tailing. (For a review see Morrow, 1979, Methods in Enzymology 68: 3.)

Identification of the specific DNA fragment containing the gD gene may be accomplished in a number of ways. Firstly, it is possible to sequence the viral DNA fragments (Maxam and Gilbert, 1980, Methods in Enzymology 65: 499) and then identify the fragment containing the gD gene sequence based upon a comparison of the predicted amino acid sequence to the amino acid sequence of the gD protein. Secondly, the fragment containing the gD gene may be identified by mRNA selection. The HSV DNA fragments are used to isolate complementary mRNA's by hybridization. Immunoprecipitation analysis of the in vitro translation products of the isolated mRNAs identifies the mRNA and, therefore, the complementary HSV DNA fragments that contain gD gene sequences. Finally, gD-specific mRNAs may be selected by adsorption of polysomes isolated from HSV-infected cells to immobilized monoclonal antibodies directed against gD. A radiolabeled gD mRNA or cDNA can be synthesized using the selected mRNA (from the adsorbed polysomes) as a template. The radiolabeled mRNA or cDNA may then be used as a probe to identify the HSV DNA fragments containing gD sequences (Southern, 1975, J. Mol. Biol. 98: 503; Alwine et al., 1979, Methods in Enzymology, 68: 220).

Alternatives to isolating the gD gene include, but are not limited to, chemically synthesizing the gene sequence itself (provided the sequence is known) or making cDNA (complementary DNA) to the mRNA which encodes the gD gene. To accomplish this, mRNA specific for gD is isolated from virus-infected cells. By standard techniques the isolated mRNA is then converted to a cDNA copy and inserted directly into a cloning vector.

Transformation of host cells with recombinant DNA molecules that incorporate the isolated gene, cDNA or synthesized DNA sequence enables generation of multiple copies of the gene. Thus, the gene may be obtained in microgram quantities by growing transformants, isolating the recombinant DNA molecules from the transformants and retrieving the inserted gene from the isolated recombinant DNA. Alternatively, microgram quantities of the gD gene may be obtained from the source of the gD gene, e.g., herpes simplex virus in infected animal cells, or bacteria or phage containing the viral gene in recombinant plasmids. The viral or plasmid DNA is isolated, fragmented, fractionated and sized by the same methods which may be used to locate the gene.

5.2. Insertion of the HSV GLY Coprotein Gene into a Cloning Expression Vector Once isolated, the gD gene or gene fragment is inserted into an appropriate expression vector, i.e., a vector which contains the necessary elements for transcription and translation of the inserted gene (see Roberts and Lauer, 1979, Methods in Enzymology, 68: 473). To obtain efficient expression of the gD gene (or a portion of the gene), a promoter must be present in the expression vector. RNA polymerase normally binds to the promoter and initiates transcription of a gene or a group of linked genes and regulatory elements (called an operon). Promoters vary in their "strength", i.e., their ability to promote transcription. For the purpose of molecular cloning it is desirable to use strong promoters in order to obtain a high level of transcription and, hence, expression of the gene. Depending upon the host cell system utilized, any one of a number of suitable promoters may be used. For instance, when cloning in an *E. coli* host cell system, any of the promoters isolated from *E. coli*, its bacteriophages or plasmids may be used (e.g., the lac promoter). Additionally, *E. coli* promoters produced by recombinant DNA or other synthetic DNA techniques may be used to provide for transcription of the inserted gene. More specifically, the $P_R$ and $P_L$ promoters of coliphage lambda direct high levels of transcription of adjacent DNA segments. In addition, the recA promoter from *E. coli* provides for high levels of gene transcription of adjacent fragments.

Specific initiation signals are also required for efficient gene transcription and translation in procaryotic and eucaryotic cells. These transcription and translation initiation signals may vary in "strength" as measured by the quantity of gene specific messenger RNA and protein synthesized, respectively. The DNA expression vector, which contains a promoter may also contain any combination of various "strong" transcription and/or translation initiation signals. Thus, any SD-ATG combination that can be utilized by host cell ribosomes may be employed; such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other synthetic technique may be used.

Any of the methods previously described for the insertion of DNA fragments into a vector may be used to ligate a promoter and other control elements into specific sites within the vector.

Accordingly, the gD gene (or any portion thereof) can be ligated into an expression vector at a specific site in relation to the vector promoter and control elements so that the gD gene sequence is in the correct translational reading frame (i.e., in phase) with respect to the vector ATG sequence. Alternatively, a gD ATG or synthetic ATG may be used. The resultant recombinant DNA molecule is then introduced into appropriate host cells by transformation, transduction or transfection (depending upon the vector/host cell system). Transformants are selected based upon the expression of appropriate gene markers normally present in the vector, such as ampicillin resistance or tetracycline resistance in pBR322, or thymidine kinase activity in eucaryotic host systems. Expression of such marker proteins indicates that the recombinant DNA molecule is intact and is replicating. The expression vectors, which usually contain a marker function, may include, but are not limited to the following vectors or their derivatives: SV40 and adenovirus vectors, yeast vectors, bacteriophage vectors such as lambda gt-WES-lambda B, Charon 28, Charon 4A, lambda gt-1-lambda BC, lambda gt-1-lambda B, M13mp7, M13mp8, M13mp9, or plasmid DNA vectors such as pBR322, pAC105, pVA51, pACY177, pKH47, pACYC184, pUB110, pMB9, pBR325, Col El, pSC101, pBR313, pML21, RSF2124, pCR1 or RP4. The expression vectors used in the examples of the present invention are described in more detail in U.S. patent application Ser. No. 449,187 filed Dec. 13, 1982, which is herein incorporated by reference.

In addition, host cell strains may be chosen which inhibit the action of the promoter unless specifically induced. In this way greater than 95% of the vector's promoter's effectiveness may be inhibited in uninduced cells. In certain operons the addition of specific inducers is necessary for efficient transcription and translation of the inserted DNA; for example, the lac operon is induced by the addition of lactose or IPTG (i.e., isopropylthio-$\beta$-D-galactoside). A variety of other operons, such as trp, pro, etc., are under different controls. The trp operon is induced when tryptophan is absent from the growth media; and the $P_L$ promoter of lambda is induced by an increase in temperature in host cells containing a temperature sensitive lambda repressor protein, e.g., CI857. Thus, expression of the genetically engineered gD protein may be controlled. This is important if the protein product of the cloned gene is lethal to host cells. In such cases, the foreign gene may be replicated but not expressed during growth of the transformants. After the cells reach a suitable density in the growth medium, the promoter can be induced for production of the protein.

The gD-related proteins produced in cells transformed with plasmids constructed as described above (i.e., plasmids which direct the expression of gD-related proteins terminating at the natural gD translation termination signal and which initiate at an ATG provided by the vector, the gD gene, or a synthetic sequence) are hereinafter referred to as unfused gD proteins or unfused gD-related proteins.

5.3. Preparation of Fusion Proteins

To maximize the level of gene expression in a specific transformant it may be desirable to ligate the gene in question to a gene encoding another protein, such as a host cell protein. An additional advantage is obtained if the host cell protein inherently contains an assayable function. The expression of the ligated genes results in a fusion protein product (hereinafter referred to as gD fusion proteins) that can be identified on the basis of its large molecular weight and assayable function. For example, production of a gD/$\beta$-galactosidase fusion protein offers several advantages for cloning and expression of gD in an *E. coli* host. First, this allows for an approximation of the level of protein production (hence expression) directed by the vector using a colorimetric assay specific for $\beta$-galactosidase activity according to the method of Miller (pages 47–55 and 352–355 in Experiments in Molecular Genetics, Cold Spring Harbor Press, New York, N.Y., 1972). Second, fusion protein production simplifies the identification and isolation of the protein product. The unfused gD protein produced by *E. coli* transformants is smaller than the gD/$\beta$-galactosidase fusion protein and as such may co-migrate with several other host proteins analyzed by SDS-polyacrylamide gel electrophoresis. However, the fusion protein produced can be easily detected and identified by SDS-polyacrylamide electrophoresis (SDS-PAGE) due to its unique large molecular weight.

The present invention is not limited to the production of a $\beta$-galactosidase fusion protein; any gene of either eucaryotic or procaryotic origin may be ligated in phase with the gD gene (or any HSV protein gene) to provide advantages similar to the $\beta$-galactosidase fusion protein product. Examples include, but are not limited to, galactokinase; trp D, E or leader; pilus genes; and eucaryotic genes, such as thymidine kinase, $\beta$-globin, SV-40 T-antigen, or Rous Sarcoma Virus transforming gene.

In order to construct a gene which encodes a fusion protein, the two genes must be joined within their coding sequence such that the translational reading frame is maintained and uninterrupted by termination signals. Also; as previously explained, if the host cell is a strain which inhibits the action of the promoter, the fusion protein will be produced only in response to induction.

5.4. Identification of the Gene Product

Once transformants which contain the correct DNA construction are identified, an analysis of the immunoreactivity and antigenicity of the recombinant DNA gD gene product is required. Unless the host cell is capable of glycosylating the gD gene product in the same pattern as naturally occurring HSV-gD, the gD gene product will differ from the natural gD glycoprotein. Thus, immunological analysis is especially important for the gD gene product because the ultimate goal is to use the gD-related protein so produced in a vaccine formulation. The analysis of immunoreactivity is most easily carried out using antisera directed against the gD glycoprotein of HSV-infected cells, whereas antigenicity may be evaluated by determining test animal antisera titers which develop in response to immunization with the gD gene product and the ability of the antisera to neutralize HSV infection.

A variety of antisera are available for analyzing immunoreactivity including polyvalent antibody preparations directed against the whole virus or gD in particular. Greater specificity is obtained by using monoclonal antibodies which recognize only one antigenic site on the gD protein molecule. A variety of monoclonal antibodies directed against gD exist, some of which not only specifically immunoprecipitate the gD gene product of HSV-1 and HSV-2 but also neutralize the infectivity of either virus.

Identification of the protein described in this invention is, therefore, based upon two requirements. First, the gD-related protein should be produced only in response to induction of the promoter. Second, the gD-related protein should be immunoreactive using a variety of polyclonal antibodies directed against HSV or monoclonal antibodies directed against gD; the protein should be immunoreactive whether it results from the expression of the entire gene sequence, a portion of the gene sequence or from two or more gene sequences which are ligated to direct the production of a fusion protein. This reactivity may be demonstrated by standard immunological techniques, such as immunoprecipitations, immunodiffusion, radio-immune competition, immunoelectrophoresis or the immunological detection of proteins which were separated by polyacrylamide gel electrophoresis and then transferred to nitro-cellulose.

5.5. Purification of the Gene Product

Cells containing the gD gene (or any HSV-glycoprotein gene) are grown up in a large volume and the protein produced after induction of the promoter is isolated from such cells or from the medium if the protein is excreted. The protein may be isolated and purified either by standard chromatography including ion exchange, affinity or sizing resins, by centrifugation, or by any other standard technique for the purification of proteins.

Since certain fusion proteins form aggregates when overproduced in cells and when in solution, a method for isolating aggregate-forming protein is particularly useful for isolating the fusion proteins produced in the present invention. These fusion proteins can then be used in vaccine formulations. Purification of fusion proteins (hereinafter referred to as aggregate purification) involves the extraction, separation and/or purification of aggregate-forming proteins by disruption of cells followed by washing the aggregated material. Additionally, the aggregated material may be solubilized by the addition of a solvent that is both a strong hydrogen acceptor and a strong hydrogen donor (or a combination of solvents each having one of these properties); the aggregate-forming proteins may then be precipitated by dilution with a compatible buffer. Suitable protein solvents include, but are not limited to urea (from about 4M to about 8M), formamide (at least about 80%, volume/volume basis), and guanidine hydrochloride (from about 4M to about 8M). Some solvents which are capable of solubilizing aggregate-forming proteins, for example SDS (sodium dodecyl sulfate), 70% formic acid, are inappropriate for use in this procedure because subsequent precipitation of the solubilized aggregate-forming proteins has proved to be inefficient. Although guanidine hydrochloride and other similar agents are denaturants, studies indicate that this denaturation is not irreversible and that renaturation may occur upon removal (by dialysis, for example) or dilution of the denaturant, allowing re-formation of immunologically and/or biologically active protein.

One embodiment of the fusion protein isolation technique is outlined as follows (hereinafter referred to as the non-denaturing aggregate purification procedure): the cell pellet is quick frozen using dry ice/methanol, weighed, and 3–4 g of cells are resuspended in at least 25 ml of a buffer solution [e.g., 50 mM Tris-HCl (tris hydroxymethylaminomethane-hydrochloride), pH 8.0, 2 mM EDTA (ethylenediaminetetraacetic acid) and 200 mM NaCl]. That is, the cells are suspended in a buffer solution at an approximate concentration of from about 100 to 200 grams of cells/liter. Concentrations less than about 160 grams/liter are preferred. To this suspension lysozyme is added to a final concentration of about 130 μg/ml and the resulting mixture is allowed to stand at 4° C. for 20 minutes with occasional shaking. Nonidet P40 (NP-40, Shell trademark, polyoxyethylene (9) p-tert-octylphenol), a non-ionic detergent used to solubilize membranes, is added to a final concentration of about 0.1% and the solution mixed. Then, the suspension is ground for approximately 1 minute using a Polytron grinder (Brinkman Instruments, Westbury, N.Y.) or equivalent.

The suspension is centrifuged at 8,000×g for 30 minutes, and the pellet resuspended in a wash buffer, e.g., 20 mM Tris-HCl (pH 7.2), 1 mM EDTA, 150 mM NaCl and 2% Triton-X 100 (polyoxyethylene (9–10) p-tert-octylphenol, a non-ionic detergent), and ground with the Polytron grinder. This step of centrifugation, washing, and grinding may be repeated to further wash the pellet and remove as much cellular debris as possible.

Alternatively, the pellet of aggregates may be further treated by the addition of a denaturant (hereinafter referred to as the denaturing aggregate purification procedure) as follows: The suspension is centrifuged, the supernatant removed completely and the pellet resuspended in about one-fifth volume of 6M guanidine hydrochloride (in distilled water). For instance, 3 g of cells washed with 25 ml of buffer should be resuspended at this step in 5 ml of 6M guanidine hydrochloride solution. It may be difficult to resuspend the pellet at this stage and sonication or homogenization may be required in order to obtain a homogenous solution. The solution is allowed to stand at 22° C. for 20 minutes and is then centrifuged at 8,000×g for 30 minutes to remove debris, saving the supernatant which at this point contains the fusion protein.

The fusion protein is precipitated from the guanidine hydrochloride supernatant by the addition of about four volumes of aqueous buffer. Almost any aqueous buffer may be used at this stage; however, the addition of a small amount of non-ionic detergent, such as 0.5% NP-40 or Triton X-100 may be helpful. This suspension is allowed to stand at 4° C. for 30 minutes and is then centrifuged at 8,000×g for 10 minutes. The supernatant is discarded, the pellet (containing the fusion protein precipitate) is resuspended in an appropriate buffer, e.g., Phosphate Buffered Saline (PBS) in any appropriate volume. Brief sonication or homogenization may aid in obtaining a homogenous suspension or slurry (since aggregate-forming proteins are insoluble in water).

5.6. Preparation of Unfused gD Protein

It may be desirable to use unfused gD protein in vaccine formulations. However, as previously explained, transformants which produce unfused gD proteins, do so in smaller quantities than transformants which produce gD fusion proteins; this is true even when the gene sequence for the unfused protein is under the control of an inducible promoter. In addition, the unfused gD proteins produced by bacterial transformants may be less stable than gD-fusion proteins.

In an alternate embodiment of the present invention, a host cell transformant can be engineered to produce large quantities of both fused and unfused gD related proteins which will coaggregate and can be purified easily. According to this embodiment, the recombinant plasmids which encode gD fusion proteins are altered at the junction of the gD gene sequence and the host cell protein gene sequence (e.g., the β-galactosidase z-gene sequence) so that a non-sense codon sequence, i.e., a chain termination sequence such as amber (TAG), ochre (TAA), or opal (TGA) is located in between the two gene sequences; the chain terminator must be in phase with the translational reading frames of both the gD sequence and the host cell gene sequence. Such an alteration may be accomplished by cleaving the plasmid at a restriction site (or sites) located in between the two gene sequences and then ligating a DNA linker sequence encoding a chain terminator such as amber, ochre, or opal into the cleaved site on the plasmid so that the chain terminator is in phase with the translational reading frames of both gene sequences.

Introduction of these amber, ochre, or opal modified plasmids into a host cell containing the appropriate tRNA suppressors results in the synthesis of both an unfused gD-related protein as well as gD-fusion protein. If the amber, ochre, or opal modified plasmids are used to transform non-suppressor cell lines, the unfused gD-related protein will be predominantly produced.

There are at least two ways to introduce the amber, ochre, or opal modified plasmids into a suppressor cell background: (1) the transformant (i.e., a host cell transformed with amber, ochre, or opal modified plasmid) can be infected with a lysogenic transducing phage that carries the appropriate suppressor tRNA gene (e.g. φ80 pSU3 carries the SupF suppressor of amber mutations); or (2) the amber, ochre, or opal modified plasmids can be used to transform cell lines which contain suppressor tRNAs of amber, ochre, or opal respectively. Examples of such strains include but are not limited to LE392 (containing supE and supF suppressors of amber mutations), YMC (containing supF), and C600 (supE). The various amber suppressor tRNA genes in *E. coli* include but are not limited to: supB, supC, supD, supE, supF, supG, supL, supM, supN, supO, supP, supU, supV; the various ochre suppressor tRNA genes in *E. coli* include but are not limited to: supB, supC, supG, supL, supM, supN, supO, supV; and the various opal suppressor tRNA genes in *E. coli* incude but are not limited to: supK (see Bachmann and Low, 1980, Microbiological Reviews 44(1): 1–56).

The host cells containing the appropriate suppressor tRNA gene which are transformed with the amber, ochre, or opal modified plasmids can produce a gD related protein as both a fusion protein and as an unfused protein (the proportions of fused gD to unfused gD protein produced depends upon the extent of suppression in the host cell); both proteins immunoreact with antisera directed against HSV. Both the unfused gD and the gD-fusion protein co-purify when using the non-denaturing aggregate purification procedure (in this case the procedure is a non-denaturing co-aggregate purification procedure) described in Section 5.5; after solubilization the unfused gD can be separated from the gD fusion protein on the basis of size or charge. As a result, large quantities of an unfused gD-related protein produced by host cell transformants can be easily purified and formulated for use as a vaccine.

5.7. Formulation of a Vaccine

The purpose of this invention is to produce, by recombinant DNA techniques, an HSV glycoprotein-related polypeptide, such as a gD-related protein, which may be used as an immunogen in a vaccine to protect against HSV-1 and/or HSV-2 infections. If the gD-related protein produced is immunoreactive to specific HSV-1 and/or HSV-2 neutralizing antibodies, it would be expected that the gD-related protein would elicit an immune response capable of neutralizing the relevant virus in vivo. Vaccines made from genetically engineered immunogens should be safer than conventional vaccines made from attenuated virus because there is no risk of infection of the recipient. Alternatively, the genetically engineered gD product may be used to produce antibodies for use in passive immunotherapy.

Although the gD/β-galactosidase fusion protein product itself may be useful in a vaccine formulation, it may be necessary to first remove the β-galactosidase moiety. Alternatively, reconstruction of the amino-coding terminus of the gD gene may be important for immunogenicity of the protein because the amino terminus may contain additional significant antigenic sites. The amino-coding terminus of the gD gene may be reconstructed by ligating a DNA sequence which encodes the amino terminus of gD into the appropriate site within the gD-coding region of the recombinant DNA molecule. Since the recombinant DNA molecule retains all the necessary expression control elements, a full length (or nearly full length) gD-related protein is produced by cells transformed with the DNA molecule containing the reconstructed gene.

Finally, the genetically engineered gD-related protein may be isolated and purified from the host cells using standard protein isolation techniques or by the aggregate purification method described herein. The final purified product may then be diluted to an appropriate concentration and formulated with any suitable vaccine adjuvant and packaged for use. Suitable adjuvants include but are not limited to: surface active substances, e.g., hexadecylamine, octadecylamine, lysolecithin, dimethyldioctadecylammonium bromide, N,N-dioctadecyl-N'-N-bis(2-hydroxyethyl-propane diamine), methoxyhexadecylglycerol, and pluronic polyols; polyanions, e.g., pyran, dextran sulfate, poly IC, polyacrylic acid, carbopol; peptides, e.g., muramyl dipeptide, dimethylglycine, tuftsin; oil emulsions; and alum. Finally, the protein product may be incorporated into liposomes for use in a vaccine formulation, or may be conjugated to polysaccharides or other polymers.

The genetically engineered DNA molecules described herein allow great flexibility for vaccine production. For example, a vaccine could be formulated using a gD-related protein produced by transformants containing any portion of the gD gene sequence or a recombinant DNA molecule which contains multiple copies of the gD gene (or portion thereof) in tandem. The gD gene sequence (or portion thereof) may be ligated to genes that encode other immunogens so that the fused protein product could be used in the preparation of multivalent vaccines. Additionally, the gD gene sequence (or portion thereof) could be ligated to other HSV glycoprotein gene sequences (or portions thereof) in any combination. Finally, the gD sequence may be reorganized to increase the immunogenicity of the vaccine. For example, the gene sequence may be altered so that the protein product presents specific epitopes to the immune system (e.g., an antigenic site of gD that is normally unexposed may be presented to the immune system); or the regions of the gD gene sequences that encode immunosuppressive portions of the protein can be deleted.

6. Example: HSV-1 gD

According to the method of the present invention the gD-1 gene was located and identified by inserting DNA fragments of the Us portion of the HSV-1 genome (see FIG. 1*a*) into the vector pBR322 to form recombinant plasmids, each of which contained a different fragment of the HSV-1 genome. The plasmid containing the gD-1 gene was identified using three techniques (not necessarily in the order listed): (1) DNA sequencing, (2) gD-1 specific mRNA hybridization studies and (3) in vitro translation of mRNA which hybridizes to the recombinant plasmids.

Once the plasmid containing the gD-1 gene was identified, the gene was characterized by DNA sequencing and by locating the gD-1 gene termini within the recombinant plasmid. A DNA fragment which contained the gD-1 gene lacking the first 156 nucleotides of the coding sequence was isolated from the identified plasmid. This DNA fragment was ligated into a DNA vector, pJS413, to produce pEH25 which was used for cloning and expression of the gene in *E. coli.* The gene product isolated from induced transformants was identified as a gD-1 specific protein by immunoprecipitation with monoclonal antibodies directed against gD-1 and with polyvalent antibodies directed against HSV-1.

Finally, the gD-1 gene fragment was isolated from pEH25 by restriction endonuclease cleavage at specific sites so that the termination sequence (TAG) of the gD-1 coding sequence was deleted. This DNA fragment which contained a portion of the gD-1 gene and the plasmid promoter and control elements (e.g., SD-ATG) was ligated into a vector containing a β-galactosidase coding sequence. The resultant recombinant plasmid, pEH4-2, which contained the gD-1 coding sequence sandwiched between the plasmid's lac promoter with a cro SD-ATG and the β-galactosidase gene, directed the expression of a fusion protein in induced *E. coli* transformants. This fusion protein was then isolated from host cell lysates and formulated for use as an immunogen. Alternatively, the amino-coding terminus of the gD-1 gene was reconstructed and the resultant gD-1 protein was formulated for animal injections and pre-clinical trials. A detailed description of each step in the construction is presented in the subsections below.

The gD-1 related proteins and the fusion proteins produced herein are non-glycosylated and thus differ from the naturally occurring HSV-1 gD glycoprotein. However, the gD-1 related protein is immunoreactive with antibodies directed against HSV-1 and HSV-2 gD.

6.1. General Procedures used for Preparation of the Plasmids

The following subsections describe the general procedures and materials used for DNA isolation, enzyme reactions and ligation reactions.

6.1.1. Plasmid DNA Isolation

Host cell bacteria *Escherichia coli,* (*E. coli*) were transformed (Gautier and Bonewald, 1980, Molec. Gen. Genet. 178: 375) and large (microgram) quantities of plasmid DNA were isolated from cultures of *E. coli* transformants grown in M-9 broth (Miller, p. 431 in Experiments in Molecular Genetics, Cold Spring Harbor Press, New York, N.Y., 1972). Plasmids were isolated from cells in late logarithmic stage of growth using a modification of the method of Guerry et al. (1973, J. Bacteriol. 116: 1063).

6.1.2. Conditions for Restriction Enzyme Digestions

Restriction enzymes used in the present application were obtained from New England Biolabs, Inc., Beverly, Ma., unless otherwise indicated. An enzyme unit is defined as the amount required to digest 1.0 μg of lambda DNA in 15 minutes at 37° C. in a total reaction mixture of 50 μl.

All restriction enzyme total digestions were accomplished under the following conditions: each 1 μg DNA was incubated with 0.5 units of enzyme at 37° C. for 60 minutes in 20 μl buffer. Partial digestions were accomplished by modifying the conditions used for total digestion as follows: each 1 μg DNA was incubated with 0.1 units of enzyme at 37° C. for 15 minutes. Reactions were terminated by the addition of 0.1% sodium dodecyl sulfate (SDS). Thus, the reaction conditions were adjusted to obtain an average of one cleavage per DNA molecule.

6.1.3. Restriction Enzyme Buffers

The buffer used for SacI, SacII or SmaI digestions consisted of: 6.6 mM Tris-HCl (pH 7.4), 6.6 mM $MgCl_2$ and 6.6 mM β-Me (β-mercaptoethanol).

The buffer used for BglII, BstEII, EcoRI, HindIII, NruI, PstI, or PvuII, digestions consisted of: 60 mM NaCl, 6.6 mM Tris-HCl (pH 7.4), 6.6 mM $MgCl_2$ and 6.6 mM β-mercaptoethanol (β-ME).

The buffer used for BamHI, SalI or XbaI digestions consisted of: 150 mM NaCl, 6.6 mM Tris-HCl (pH 7.4), 6.6 mM $MgCl_2$ and 6.6 mM β-ME.

It should be noted that whenever two or more restriction endonuclease reactions are performed on DNA, the reaction in low salt buffer is accomplished before the reaction in high salt buffer. If two enzymes require the same buffer, then the reactions may be performed simultaneously.

6.1.4. Modification of DNA

Bal 31 nuclease is a multifunctional enzyme that contains a highly specific single-stranded endodeoxyribonuclease activity and a processive exonuclease activity that simultaneously degrades both the 3'- and 5'-termini of double-stranded DNA (dsDNA). One unit of nuclease Bal 31 (New England Biolabs, Inc. Beverly, Ma.) is defined as the amount required to release 1.0 μg of acid soluble nucleotides from denatured calf thymus DNA (650 μg/ml) in one minute at 30° C. The reaction buffer used for Bal 31 consisted of: 20 mM Tris-HCl (pH 8.0), 600 mM NaCl, 12 mM $CaCl_2$, 12 mM $MgCl_2$, 1.0 mM EDTA and DNA. Incubations were at 30° C.; Bal 31 digests were accomplished by incubating 30 μg of DNA with 0.5 units Bal 31 for 1, 2, 4, 6, 8 and 10 minutes. Reactions were terminated by the addition of EDTA to 50 mM or heat inactivation of Bal 31 (i.e., 65° C. for 10 minutes).

S1 nuclease degrades RNA or denatured DNA (i.e., single-stranded DNA) into mononucleotides, but will not (under proper conditions) degrade double-stranded DNA or DNA/RNA hybrids. One unit of S1 nuclease (Boehringer Mannheim, Indianapolis, Ind.) is defined as the amount of enzyme required to acid solubilize 1 μg of denatured calf thymus DNA in 30 minutes at 37° C. The reaction buffer used for S1 nuclease consisted of 30 mM sodium acetate (pH 4.6), 250 mM NaCl, 1 mM ZnSO4 and 5% glycerol. S1 digestions were accomplished by incubating 2000 units of enzyme with 0.1 μg DNA and 20 μg RNA at 45° C. for 30 minutes.

Exonuclease VII (Exo VII) degrades single-stranded DNA (ssDNA). The mechanism of action of Exo VII appears to be that of a processive exonuclease. One unit of Exo VII (Bethesda Research Laboratories, Rockville, Md.) is defined as the amount of enzyme which produces 1 nmol of nucleotide monomers in 30 minutes at 37° C. using linear, denatured [$^3$H]-SV40 DNA as a substrate. The reaction butter used for Exo VII consisted of 10 mM Tris-HCl (pH 7.9), 100 mM NaCl, 10 mM β-ME and 8 mM EDTA. Exo VII digestions were accomplished using 4 units of Exo VII per 0.1 μg DNA in a 250 μl reaction volume for 1 hour at 45° C.

6.1.5 DNA Polymerase Reaction

DNA polymerases catalyze the stepwise elongation of a DNA chain. Chain growth is in the 5' to 3' direction (i.e., addition of nucleotides occurs at the 3'-terminus) and the sequence of the polymer is determined by that of the template because the incoming nucleotide must be complementary to the template, i.e., form the correct base pair with the template strand. The known DNA polymerases cannot initiate chain synthesis, thus DNA synthesis requires a primer strand with a free 3'-hydroxyl terminus annealed to a template strand. Chain elongation proceeds by the nucleophilic attack of the 3'-hydroxyl terminus of the primer on the 5'-phosphate of the incoming nucleotide. The new chain is base paired and antiparallel to the template strand. As a result of the DNA polymerase reaction the single-stranded template strand is "filled-in" or converted to a double-stranded DNA molecule.

A second important feature of the DNA polymerases is the "proof-reading" function. A 3' to 5' exonuclease activity associated with DNA polymerase I acts on nonbase-paired termini and can degrade both single- and double-stranded DNA in the 3' to 5' direction yielding mononucleotides. Thus an incorrectly added nucleotide is removed before polymerization continues, and the fidelity of the enzyme is further enhanced. DNA polymerase I also has a 5' to 3' exonuclease activity specific for double-stranded DNA (yielding 5'-mononucleotides and oligonucleotides) which can also excise mismatched regions in DNA.

Proteolytic treatment of DNA polymerase I by the method of Klenow (Klenow et al., 1971, Eur. J. Biochem. 22: 371) yields two fragments, large and small. The large fragment of Klenow fragment (76,000 daltons) retains the polymerase and 3'- 5' exonuclease activity whereas the small fragment retains the 5'- 3' exonuclease activity. One unit of DNA polymerase I or DNA polymerase I-large fragment (New England Biolabs, Beverly, Ma.) is defined as the amount converting 10 nmoles of deoxyribonucleotides to an acid insoluble form in 30 minutes at 37° C. The assay conditions for both enzymes are the same except that the reaction mixture for DNA polymerase I contains 67 mM KPO4 (pH 7.5) while the reaction mixture for the Klenow fragment contains 40 mM KPO4 (pH 7.5) in the following buffer: 6.6 mM MgCl2, 1.0 mM β-ME, 2 mM dAT copolymer, 33 μM dATP, 33 μM $^3$H-dTTP and enzyme.

In the present application, when DNA polymerase large (Klenow) fragment was used to fill in single-stranded DNA or choesive ends that results from restriction enzyme cleavage, the following procedure was employed: restriction enzyme reactions were teminated by heating at 68° C. for 10 minutes. To the same reaction mixture a final concentration of 50 μM of each deoxynucleoside triphosphate wa added and for each microgram of DNA in the reaction mixture 10–100 units of DNA polymerase Klenow fragment was added. In other words an excess of DNA polymerase Klenow fragment was used to ensure that single-stranded ends were completely filled in.

6.1.6. Gel Purification of DNA Fragments

After restriction enzyme or nuclease treatment, DNA fragments of varying sizes were separated by gel electrophoresis in either agarose or polyacrylamide slab gels at low voltage (approximately 2 volts/cm for agarose gels and 10 volts/cm for polyacrylamide gels), stained with ethidium bromide and visualized under ultraviolet light (Southern, 1979, Methods in Enzymology 68: 152).

In order to recover particular DNA fragments from gels, the appropriate bands were sliced out of the gel and the DNA was electroeluted into dialysis tubing. The DNA was then isolated on DEAE-cellulose, or ethanol precipitated, and resuspended in the appropriate buffer (Smith, 1980, Methods in Enzymology 65: 371).

6.1.7. DNA Ligation

All ligations were accomplished using T4 DNA ligase (New England Biolabs, Inc., Beverly MA.). One unit of T4 DNA ligase is defined as the amount required to yield 50% ligation of HindIII fragments of bacteriophage lambda DNA in 30 minutes at 16° C. in 20 μl of ligase buffer and a 5'-DNA termini concentration of 0.12 μM (300 μg/ml).

DNA ligations were carried out in ligase buffer consisting of: 60 mM Tris-HCl (pH 7.8), 10 mM MgCl2, 20 mM dithiothreitol(DTT), 1.0 mM ATP and a DNA concentration ranging from 15–50 μg/ml. Ligation reactions were incubated 4 to 24 hours at room temperature using approximately 300 units of T4 DNA ligase per 10 μl reaction volume.

6.2. Localization and Isolation of the gD-1 Gene

Figure 1:
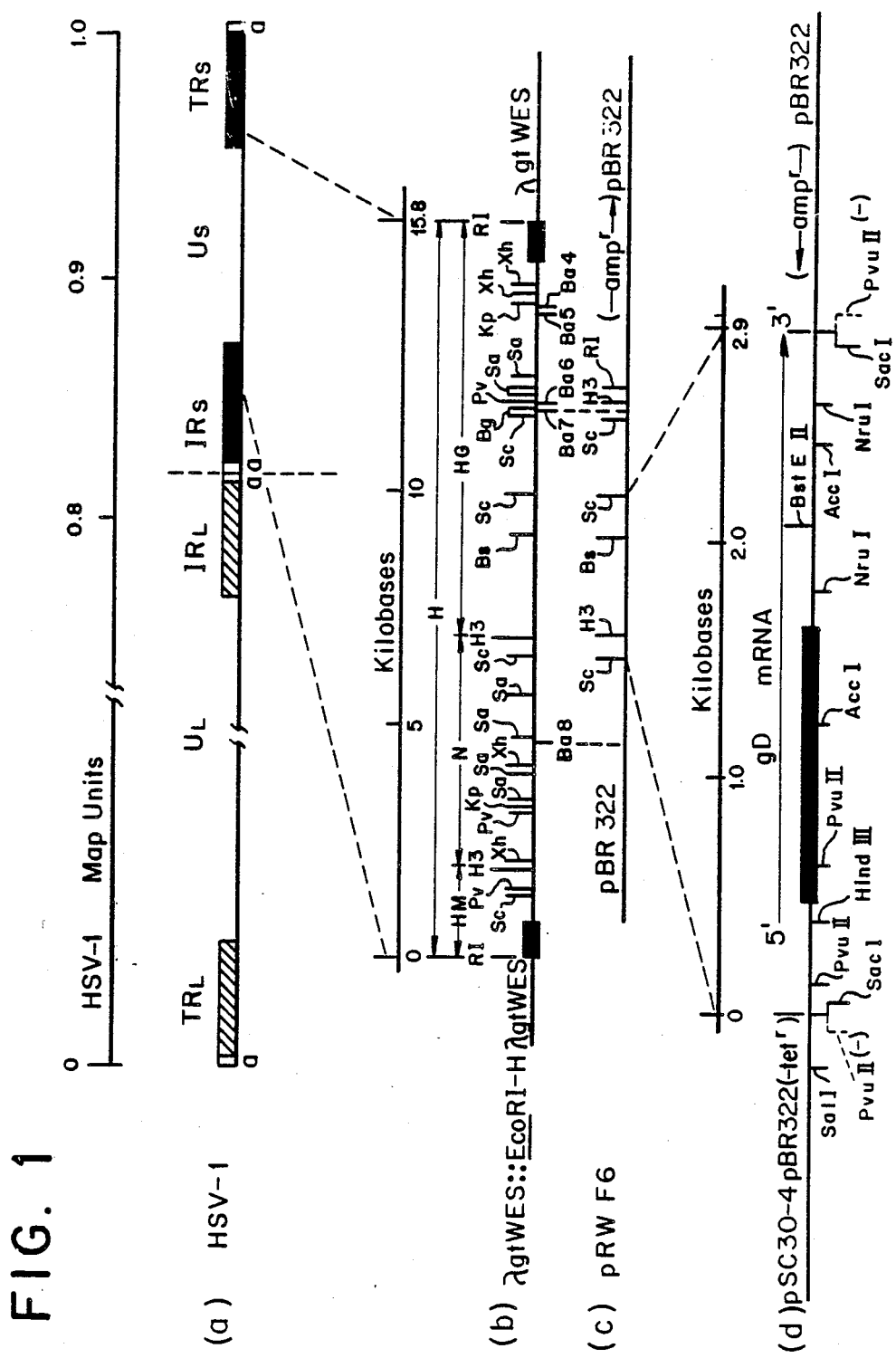
FIG. 1c represents the construction of pRWF6 which comprises an insertion of the BamHI-8 to BamHI-7 fragment of lambda gt WES: EcoRI-H into pBR322.
FIG. 1d represents the restriction map of the HSV-1 Sac I DNA fragment insert of pSC30-4. The bar (broadened area) represents the location and position of the gD-1 mRNA coding sequence.

Analysis of the proteins specified by HSV-1 × HSV-2 recombinants indicated that the gD-1 gene mapped between 0.9–0.945 genome map units within the Us region of the DNA (Ruyechan et al., 1979, J. Virol. 29: 667); see FIG. 1a and 1b. The Us region was fragmented with restriction enzymes and these fragments were inserted into cloning vectors to create various recombinant plasmids, each containing a defined portion of the Us region. These recombinant plasmids were then analyzed in order to locate the gD-1 gene within the Us region. The map position of gD-1 in HSV-1 has recently been reported by Lee et al., 1982, J. Virol. 43: 41.

6.2.1. Recombinant DNA Plasmids Containing Defined Portions of the Us Region of HSV-1

Several recombinant plasmids were constructed using the vector, pBR322, and various fragments of the Us region of HSV-1 (Patton Strain). One of these plasmids, designated pRWF6, was found to contain the entire gD-1 gene. A description of pRWF6 follows.

The HSV-1 insert of recombinant plasmid pRWF6 (FIG. 1c) was obtained from the Us region of the lambda gtWES: Eco RI-H clone (Umene and Enquist, 1981, Gene 13: 251). The lambda gtWES: EcoRI-H clone was digested to completion (total digestion) with EcoRI. The EcoRI-H fragment of the lambda gtWES: EcoRI-H clone, approximately 15–16 kb (kilobases), contains the entire Us region of HSV-1.

The plasmid, pBR322, and the EcoRI-H fragment (isolated above) of HSV-1 were each totally digested with Bam HI. The resultant 4.4 kb fragment of pBR322 and the 6.4 kb fragment of HSV-1 were annealed and ligated in a 1:1 ratio resulting in pRWF6.

6.2.2. Localization of gD-1 Specific mRNA Coding Sequence

In order to locate and select for the gD-1 specific coding sequence within pRWF6, the viral DNA insert was subcloned, again into pBR322. Denatured viral DNA restriction fragments of subclone pSC30-4 (FIG. 1d and described below) were immobilized on nitrocellulose and used to isolate mRNA (via complementary base-pair hybridization) from cytoplasmic RNA extracts of HSV-1 infected cells. Two mRNA species (3.0 kb and 1.7 kb) hybridized to pSC30-4. Translation of these mRNA species in vitro demonstrated that either the 3.0 kb or the 1.7 kb mRNA encoded the gD-1 protein. Details of the procedure are described below and depicted in FIG. 1.

The plasmid, pRWF6, was isolated from *E. coli* transformants and digested with the restriction enzyme, SacI. This generated three fragments: a 6.2 kb fragment containing the entire pBR322 vector plus a portion of the HSV-1 DNA sequence, a 2.9 kb HSV DNA fragment and a 1.7 kb HSV-1 DNA fragment.

In order to subclone the 2.9 kb HSV-1 DNA fragment (see FIG. 1d), pBR322 was cleaved with PvuII (which linearizes pBR322) and ligated in the presence of SacI linkers (New England Biolabs, Inc., Beverly, Ma.) using T4 DNA ligase. Thus, the unique PvuII site of pBR322 was converted to a unique Sac I site [designated SacI (Pvu II(−))]. After cleavage of the modified pBR322 vector with SacI enzyme, this vector was ligated with the 2.9 kb HSV-1 SacI DNA fragment, resulting in pSC30-4. This recombinant plasmid was used to transform *E. coli*. Transformants were screened and selected by restriction mapping using a mini-lysate technique (Clewell and Helinski, 1970, Biochem. 9: 4428).

The subclone pSC30-4 was used for mRNA hybridization-selection as follows: (Ricciardo et al., 1979, Proc. Natl. Acad. Sci., U.S.A. 76: 4927). The plasmid, pSC30-4, was isolated from *E. coli* transformants and 200 µg pSC30-4 DNA was digested with SacI in order to excise the HSV-1 DNA insert. The cleaved plasmid was extracted with chloroform/phenol (1:1) and ethanol precipitated. The pellet was resuspended in 2 ml of 0.3M NaOH and incubated at room temperature for 10 minutes in order to denature the DNA. The suspension was then neutralized by the addition of 4.4 ml distilled water, 0.2 ml 3M HCl, 0.2 ml 1M Tris-HCl (pH 7.5) and 3 ml 20×SSC (SSC is 0.15M NaCl, 0.015M sodium citrate). The pH, measured with indicator paper, was between 6 and 8. The denatured, neutralized DNA was vacuum filtered through a 25 mm nitrocellulose filter (Schleicher and Schuell, Keene, N.H.) which was presoaked in distilled water followed by 6×SSC. After vacuum filtration, the nirocellulose filters were washed with 6×SSC, dried and baked at 80° C. for 2 hours. One-half of the nitrocellulose filter was used for the hybridization procedure as outlined below.

The nitrocellulose containing the viral DNA was cut into small pieces and incubated with total cytoplasmic RNA that was isolated from lysates of HSV-1 infected Vero cells prepared as follows: Vero cells were infected with 10 plaque forming units (pfu)/cell and incubated for 7 hours at 37° C. in Dulbecco's medium with 50 µg/ml cytarabine (β-cytosine arabinoside) added to prevent DNA replication. The cells were lysed with 0.65% NP-40 in 0.15M NaCl, 1.5 mM MgCl$_2$ and 0.01M Tris-HCl (pH 7.9). The nuclei were sedimented by centrifugation at 3000×g for 2 minutes, and the supernatant was adjusted to a final concentration of 1 mM EDTA (pH 7.9) and 0.5% SDS. The solution was extracted twice with chloroform/phenol (1:1) and once with chloroform. The cytoplasmic RNA was ethanol precipitated (one confluent roller bottle of Vero cells yielded about 1.5 mg RNA) and partially dried. The RNA pellet (about 0.4–0.8 mg RNA) was dissolved in 400 µl hybridization buffer (50% formamide, 0.4M NaCl, 40 mM PIPES, pH 6.4, 1 mM EDTA and 1% SDS) and added to the chopped up nitrocellulose filter. The hybridization was done at 55° C. for 3 hours in a shaking water bath.

The filter pieces were then washed 10 times with SSC containing 0.5% SDS at 60° C., followed by 2 washes with 1 ml 2 mM EDTA in SSC at 60° C. Finally the filter pieces were washed with 2 mM EDTA, pH 8.0, at 60° C. for 5 minutes; the solution was removed and the filter pieces were thoroughly dried with a cotton swab.

The hybridized mRNA was eluted from the nitrocellulose pieces using formamide and heat as follows: 120 µl 95% formamide/10 mM PIPES (pH 6.5) was added to the filters and incubated 5 minutes at 65° C. The eluate was transferred to a microcentrifuge tube and retained on ice. A second 120 µl of the elution buffer was added to the nitrocellulose pieces and incubated again at 65° C. for 5 minutes. This eluate was transferred to a second microcentrifuge tube and retained on ice. A 720 µl aliquot of sterile distilled water was added to the filters which were then agitated. About 360 µl was then transferred to each microcentrifuge tube containing the eluates. To the eluted RNA in the microcentrifuge tubes 20 µl 5M NaCl, 5 µg suitable carrier (e.g., rabbit liver tRNA) and 1 ml absolute ethanol was added. The RNA was precipitated by incubating the mixture for 1 hour at −70° C. or by immersing the tubes in a slurry of dry ice/EtOH for 20 minutes. The precipitated RNA was pelleted (10 minutes at 12,000×g) in a microcentrifuge and the precipitate of one tube was resuspended in 1 ml buffer (0.5M NaCl, 10 mM Tris-HCl (pH 7.9) and 0.5% SDS) in order to dissolve the RNA. The dissolved RNA was added to the duplicate tube in order to combine aliquots and dissolve all the precipitated RNA. The polyadenylated RNA [poly(A)RNA] was isolated from the dissolved RNA by chromatography using Oligo (dT)-cellulose (Bethesda Research Laboratories, Inc., Rockville, Md.). The poly(A)RNA was eluted from the Oligo(dT) cellulose using 10 mM Tris-HCl (pH 7.9), and 0.1% SDS as the elution buffer; the poly(A)RNA was then ethanol precipitated as previously described.

Two species of mRNA which hybridized to the pSC30-4 DNA were isolated, a 3.0 kb and 1.7 kb mRNA. These two species were translated in vitro using a rabbit reticulocyte cell-free system containing $^{35}$S-methionine (Pelham and Jackson, 1976, Eur. J. Biochem. 67: 247).

The in vitro translation extracts were immunoprecipitated with monoclonal antibody 4S which is directed against gD-1 (provided by M. Zweig, National Institute of Health) and prepared for SDS-PAGE as previously described. Electrophoretic analysis of the immunoprecipitated protein products of the cell-free translation system demonstrated that these selected mRNAs specified at 50,000 dalton gD-1 specific protein (data not shown). According to the size of gD-1 protein, the minimum mRNA coding sequence would be approximately 1.6 kb; thus, taking mRNA leader sequences and poly (A) tails into account, the larger (3.0 kb) mRNA was suspected to encode the gD-1 polypeptide.

6.2.3. Characterization of the gD-1 mRNA

Mapping the position of the 3.0 kb mRNA sequence within pSC30-4 and characterizing the mRNA was accomplished by S1 mapping, i.e., using single-strand specific nuclease S1 and Exonuclease VII to map the regions of DNA probes that hybridized to complementary mRNA sequences (Berk and Sharp, 1978, Proc. Natl. Acad. Sci., U.S.A. 75: 1274), and by sequencing the DNA of the gD-1 gene coding region (Maxam and Gilbert, 1980, Methods in Enzymology, 65: 499).

The S1 mapping technique demonstrated that both the 3.0 kb and the 1.7 kb mRNA species were unspliced (i.e., did not contain intervening sequences or introns) and that they had different 5'-termini, but common 3'-termini. A 1608 nucleotide DNA sequence including the coding region at the 5'-terminus of the 3.0 kb mRNA was determined and the reading frame of translation was deduced by locating the initiation codon (ATG) closest to the 5'-terminus.

The principle of the S1 mapping technique is to allow duplex formation between RNA and a radiolabeled single-stranded DNA (ssDNA) probe (e.g., obtained from pSC30-4). If the RNA is a mature spliced mRNA, then the introns will form a ssDNA loop. The enzyme nuclease S1 digests all ssDNA regions of the radiolabeled DNA that are not protected by duplex formation with RNA, whereas Exonuclease VII digests ssDNA only at the termini and, therefore, will not digest the ssDNA loops. Comparison of the size of DNA not susceptible to these nucleases (by virtue of hybridization to RNA) enables the detection of spliced nRNA transcripts.

In the present invention the radiolabeled DNA used to locate the 5'-terminums of the 3.0 kb mRNA was a 3.8 kb BamHI-8/BstEII fragment of pRWF6 which was labeled with $^{32}$P (using the enzyme, polynucleotide kinase, according to the method of Maxam and Gilbert, supra) at its BstEII 5'-terminus before cleavage with BamHI. The radiolabeled DNA used to locate the 3'-terminus of the 3.0 kb mRNA was a 4.7 kb HindIII/SalI fragment of pSC30-4 which was labeled with $^{32}$P (using the Klenow fragment of DNA polymerase, according to the method of Maxam and Gilbert, supra) at its HindIII 3'-terminus before cleavage with SalI. Cytoplasmic mRNA was isolated from HSV-1 infected Vero cells grown for 7 hours in the presence of cytarabine as previously described. The S1 mapping technique used was a modification of the Berk and Sharp procedure (Watson et al., 1981, J. Virol. 37: 431). The 5'-terminus of gD-1 mRNA mapped near the HindIII site of pSC30-4, while the 3'-terminus mapped approximately 2.8 kb downstream (FIG. 1d).

Finally, the HSV-1 DNA of pSC30-4 was sequenced using the Maxam and Gilbert method. FIG. 2 demonstrates the sequenching strategy for the HSV-1 gD gene coding region. Both the coding and non-coding strands were sequenced. FIG. 3 represents the DNA sequence obtained for the HSV-1 gD gene. It was apparent that the DNA sequence contained an open reading frame of 394 codons extending from an ATG at position 241. This site was suspected to be the initiator of the gD-1 gene and was shown to be so by the cloning of this putative gD-1 gene sequence into expression vector pJS413 (see Section 6.3).

6.3. Cloning and Expression of the gD-1 Gene

The gD-1 coding sequence was placed under control of the lac promoter. To this end, a portion of the putative gD-1 gene (hereinafter referred to as the gD-1 gene), lacking the initiation sequence, ATG, and the first 156 nucleotides of the amino-coding terminus (5'-end of the gene) was ligated into a DNA cloning expression vector, pJS413, to form pEH25 (see FIG. 4). The partial gD-1 gene was inserted so that the protein coding sequence was in the correct reading frame with respect to the initiation ATG of the vector. As a result, subsequent translation of the transcribed mRNA begins at the initiation sequence (ATG) of the vector through the gD-1 gene (lacking its own initiation ATG and the first 156 nucleotides of the gD-1 coding sequence) to the natural termination signal of gD-1.

The pEH25 plasmids containing the gD-1 gene were used to transform an E. coli host strain in which the transcription of DNA from the lac operon is inhibited unless the promoter is specifically induced. Primary transformants were assayed for drug resistance (the ampicillin resistance gene is carried on the vector) and resistant clones were analyzed further. The structure of the resultant recombinant plasmid, pEH25, was verified by restriction analysis and DNA sequencing. Induction of pEH25 transformants resulted in the production of a 46,000 dalton polypeptide that was immunoprecipitable with either antisera directed against HSV or monoclonal antibodies directed against gD. These procedures are described in more detail in the following subsections.

6.3.1. The Expression Vector pJS413

The expression vector, pJS413 (FIG. 4), is a pBR322 derivative which contains the amp$^r$ ($\beta$-lactamase) gene, a lac promoter (P lac), lac and cro ribosome binding sites (SD$^{lacZ}$ and SD$^{cro}$ are represented in all figures as SD$^z$ and SD$^{cro}$, respectively), a chain initiation ATG with 69 nucleotides of cro (cro), and a modified $\beta$-galactosidase gene (the lac i-z gene, hereinafter referred to as the z-gene). Insertion of a gene in the correct reading frame between the cro initiation ATG of pJS413 and the z-gene (i.e., within the BglII, SmaI or BamHI cloning sites of pJS413) allows for expression of a fusion protein in transformed cells. In the present example, however, the z-gene was deleted and the partial gD-1 gene was ligated in phase with the pJS413 cro initiation ATG and cro nucleotides.

In order to prepare pJS413 for insertion of the gD-1 gene (see FIG. 4), pJS413 was digested with SmaI (resulting in a blunt end) and SacI (resulting in SacI 3'-cohesive end). The 4.7 kb fragment, containing the promoter, SD sequences, initiation ATG and partial cro sequence, was isolated by gel electrophoresis. The 1.8 kb fragment containing the 5'-terminus of the z-gene was deleted.

6.3.2. Insertion of the gD-1 Gene into pJS413

After mapping the gD-1 gene within pSC30-4 (Section 6.2.3), a 2.2 kb DNA fragment containing the last 1026 bp (base pairs) of the carboxy-coding terminus of the gD-1 gene was selectively isolated from pSC30-4 by digestion with PvuII (resulting in a blunt end) and SacI (resulting in a SacI B 3'-cohesive end) (FIG. 4).

The 2.2 kb PvuII/SacI pSC30-4 -fragment and the 4.7 kb SmaI/SacI pJS413 fragment were ligated in a 1:1 ratio using T4 DNA ligase (FIG. 4). The resultant recombinant plasmids were used to transform *E. coli* strain NF1829. The *E. coli* strain NF1829 is a K-12 MC1000 derivative carrying an F'-lac episome with the lac I$^Q$ mutation for lac repressor overproduction. The lac z-gene endocing β-galactosidase present on the F'-lac episome is inactivated by a Tn 5 (transposon) insertion. Thus, in strain NF1829, the lac promoter must be induced in order to obtain expression of a gene inserted into the pJS413 plasmid.

6.3.3. Identification of Transformants that Express the gD-1 Gene

The plasmids isolated from ampicillin resistant *E. coli* transformants were analyzed by restriction enzyme mapping and by DNA sequencing of the junction between the pJS413 vector, and the gD-1 gene insert. The plasmid pEH25 (FIG. 4) had the correct nucleotide sequence across the Cro-gD-1 junction (depicted in FIG. 5), and was examined for its ability to direct the expression of a gD-1 related polypeptide. Since the lac promoter was transcriptionally inactive in NF1829 (due to the overproduction of the lac repressor) the gD-1 protein could only be detected upon induction of the promoter with either 1 mM IPTG or 1-10 mM lactose.

The clone transformed with pEH25 was examined for IPTG-specific induction of the gD-1 related protein and was found to produce a 46,000 dalton protein consisting of 23 amino acids of cro protein (coded for in pJS413) and 342 amino acids of the gD-1 protein (i.e., the first 52 amino acids of gD-1 are missing). This protein could be immunoprecipitated with total rabbit antisera directed against HSV-1 (DAKO Chemicals, Inc., Hicsville, N.Y.) and with monoclonal antibodies (1S, 4S, 55S and 57S) specifically directed against gD of HSV-1 (Showalter et al., 1981, Infection and Immunity, 34: 684).

Monoclonal antibodies 1S, 4S, 55S and 57S recognize a number of distinct sites on the gD-1 molecule (Eisenberg et al., 1982, J. Virol. 41: 478). Notably, monoclonal 4S is capable of neutralizing HSV-1 and HSV-2 infectivity and immunoprecipitating the gD protein produced by both viruses. The protein produced by pEH25 was immunoprecipitated by the 4S antibody, demonstrating that the pEH25 gD-1 related protein expressed antigenic determinants shared by both HSV-1 and HSV-2 gD proteins. In addition, the pEH25 gD-1 related protein was immunoprecipitated by the 1S monoclonal antibody that neutralizes only HSV-1. The pEH25 gD-1 related protein was also precipitated by the 55S and 57S monoclonal antibodies which do not neutralize either HSV-1 or HSV-2 infectivity. Each of the immunoprecipitates was analyzed by SDS-PAGE; details of the entire procedure are explained below.

All pEH25 transformants were grown by removing an aliquot of an overnight culture (stationary phase) in L broth at 37° C., diluting 20-fold in M-9 broth and growing at 37° C. with shaking for 90 minutes (Miller, Experiments in Molecular Genetics, Cold Spring Harbor Press, New York, N.Y., 1972). In assays of these cultures for expression of gD-1 protein, 1 mm IPTG and 25 μCi/ml $^{35}$S-methionine were added to the culture (controls were labeled with $^{35}$S-methionine, but were not induced). After 60 minutes at 37° C. the cultures were pelleted by centrifugation. In order to lyse the cells and release the cell contents, each pellet of cells was resuspended in an equal volume of lysis buffer, IP-3 (20 mM Tris-HCl (pH 8.1), 100 mM NaCl, 1 mM EDTA, 1% NP-40, 1% deoxycholate and 0.1% SDS), quick frozen in liquid nitrogen and sonicated. The cell lysate was centrifuged at 5,000×g for 5 minutes at 4° C., and the supernatant was divided into aliquots. Control sera (non-immune or pre-immune sera) or test antisera (polyvalent antisera directed against HSV-1 or monoclonal antisera directed against gD) were added to each aliquot which were then incubated at 4° C. for 60 minutes. (The amount of antisera added is determined by calibrating the antisera titer by testing serial dilutions of antisera using a known amount of antigen).

The immune complexes were collected by adding washed Pansorbin (*Staphyolococcus aureus* protein A, Calbiochem-Behring Corp., LaJolla, Cal.) and centrifuging (all centrifugations in this procedure were run at 5,000×g for 5 minutes at 4° C. unless otherwise indicated). The pelleted immunoprecipitate was resuspended and washed with IP-2 (identical to IP-3 but with 20 mg/ml bovine serum albumin, BSA, added to eliminate non-specific adsorption), washed twice with IP-3, and resuspended in IP-1 (20 mM Tris-HCl (pH 8.1), 100 mM NaCl, 1 mM EDTA and 1% NP-40). The suspension was transferred to a new tube in which it was centrifuged and the pellet was resuspended in SDS-polyacrylamide gel sample buffer (Laemmli, 1970, Nature 227: 680). After heating at 95° C. for three minutes, the sample was centrifuged for 2 minutes at 12,000×g in a microcentrifuge to remove insoluble components. The supernatant was removed and loaded onto an SDS polyacrylamide gel (10%). After electrophoresis the proteins were stained with Coomassie blue dye, treated with sodium salicylate and dried for fluorography (Chamberlain, 1979, Anal. Biochem. 98: 132). Results of SDS polyacrylamide gel electrophoresis (SDS-PAGE) clearly demonstrated that the pEH25-directed 46,000 dalton gD-1 related protein produced upon induction was immunoprecipitated by total rabbit antisera directed against HSV-1, and by monoclonal antibodies 1S, 4S, 55S, and 57S.

Finally, competition experiments were performed to determine the effect of lysates of HSV-1 infected Hela cells upon the immunoprecipitation of the induced gD-1 related protein expressed in *E. coli* N1829 transformed with pEH25 (see FIG. 6). A serial dilution was made of lysates of control (uninfected) and HSV-1 infected Hela cells (infections were accomplished as previously described for Vero cells). A 5 μl aliquot of a 100-fold dilution of monoclonal 55S ascites fluid (a gD-1) specific monoclonal antibody) was added to each aliquot of the dilution series of Hela cell lysates. After incubation at 4° C. for 30 minutes, equal amounts of $^{35}$S-methionine labeled proteins from lysates of induced pEH25 transformants were added to the Hela cell lysates and incubated for an additional 60 minutes at 4° C. The immune complexes were collected by immunoprecipitation and analyzed by SDS-PAGE and fluorography as previously described. The protein band which was specifically immunoprecipitated was sliced out of the gel, and the radioactivity was measured by scintillation counting. FIG. 6 represents the results of these experiments: the radioactivity of each sample, which represents the immunoprecipitated labeled protein product of pEH25, was plotted as a percentage of the control. The open circles represent the serially diluted control (uninfected) Hela cell lysate. The boxes represent the serially diluted HSV-1-infected Hela cell lysate. This clearly demonstrates that HSV-1 proteins successfully compete with radiolabeled pEH25-directed protein for the formation of immune complexes with 55S monoclonal antibody.

6.4. Preparation of pEH4-2 which Directs the Production of a Cro/gD-1/β-Galactosidase Fusion Protein The gD-1 gene was isolated from pEH25 so that its termination signal was deleted. To this end, the DNA fragment containing the gD-1 gene sequence was cleaved at a restriction site beyond the gD-1 termination sequence, TAG; the TAG was then removed by processive digestion of the termini with Bal 31, a DNA nuclease. This gD-1 gene fragment was then inserted into pJS413 in order to encode a fusion protein: Cro/gD-1/β-galactosidase. The procedure is described below and depicted in FIG. 7.

The plasmid pEH25 was digested to completion with NruI and digested processively with Bal 31 nuclease. The resulting variable length DNA was then cleaved with the restriction enzyme PstI yielding a spectrum of fragments, many of which lacked the gD-1 termination codon but retained most of the gD-1 gene sequence. The appropriate DNA fragments (1.5–1.9 kb) were isolated by gel electrophoresis and eluted as described previously. The vector pJS413 was digested to completion with PstI and SmaI and the appropriate 5.5 kb DNA fragment was isolated (FIG. 7). The pEH25 fragment and the pJS413 fragment were ligated at a 1:1 ratio and used to transform E. coli NF1829. The ampicillin resistant colonies were examined for fusion protein production by assaying for β-galactosidase activity on indicator agar plates (Miller, Experiments in Molecular Genetics, Cold Spring Harbor Press, New York, N.Y., 1972). The positive colonies were tested for the presence of the Cro/gD-1/β-galactosidase fusion protein by SDS-PAGE analysis of total lysates of transformants induced with IPTG. One high level producer of a 160,000 dalton fusion protein was isolated from those clones expressing the Cro/gD-1/β-galactosidase fusion proteins; the plasmid contained in this clone was designated pEH4-2 (FIG. 7). The fusion protein produced by the E. coli clone transformed with pEH-4-2 was shown to by inducible by IPTG and to be cross immunoreactive with both HSV-1 and HSV-2. The pEH4-2 plasmid was isolated and analyzed by restriction mapping and DNA-sequencing; pEH4-2 does not contain the BamHI site of pJS413 (see FIG. 8).

Another E. coli isolate transformed with the plasmid designated pEH3-25 produced a Cro/gD-1/β-galactosidase fusion protein in lesser amounts than did the pEH4-2 transformant. The pEH3-25 transformant is discussed later in the text (see Section 6.5).

6.4.1. pEH4-2 Fusion Protein Immunoreacts with Anti-HSV-1 Sera

The fusion protein produced by E. coli transformed with pEH4-2 specifically interacted with rabbit antisera directed against HSV-1 (data not shown). IPTG-induced proteins of pEH4-2 and pEH25 were separated by SDS-PAGE and transferred to nitrocellulose (i.e., a protein "blot" was done). Lysates of uninduced pEH4-2 and pEH25 transformants were subjected to the same procedure as controls. The nitrocellulose was then treated with rabbit antisera directed against HSV-1 followed by $^{125}$I-labeled goat antiserum directed against rabbit immunoglobulin as a probe (Towbin et al., 1979, Proc. Natl. Acad. Sci., U.S.A. 76: 4350).

Autoradiograms of the protein blots clearly demonstrated that a 160,000 dalton pEH4-2 specified fusion protein immunoreacted with rabbit antisera directed against HSV-1, and that the 46,000 dalton pEH25 specified gD-1 related protein immunoreacted with rabbit antisera directed against HSV-1.

6.4.2. Antisera Directed Against pEH4-2 Fusion Protein Immunoprecipitates HSV-1 and HSV-2 Proteins Antisera directed against the pEH4-2 fusion protein were shown to be immunoreactive with HSV-1 gD and HSV-2 gD, thus demonstrating that the pEH4-2 fusion protein contains gD specific antigenic determinants. This was demonstrated by SDS-PAGE analysis of HSV-1 proteins and HSV-2 proteins immunoprecipitated with antisera directed against pEH4-2 fusion protein; see the discussion which follows.

The rabbit antisera directed against the pEH4-2 fusion protein was produced as follows: the E. coli clones transformed with pEH4-2 were grown to mid-log phase and induced with 1 mM IPTG. Four hours after induction the bacteria were pelleted by centrifugation, lysed with SDS-PAGE sample buffer and loaded on preparative SDS-polyacrylamide gels. After electrophoresis, the proteins were visualized by staining the outer lanes with coomassie blue dye; then the 160,000 dalton fusion protein band was sliced from the gel. The gel slice was immersed in liquid nitrogen, ground to a powder and resuspended in PBS. An equal volume of Freund's complete adjuvant was then added. After thorough mixing, the solution was injected subcutaneously into two New Zealand rabbits (018 and 019). Each rabbits was injected with 25 to 50 μg protein. After 28 days the rabbits were boosted with the same amount of fusion protein suspended in incomplete Freund's adjuvant. The animals were boosted two more times at 10 day intervals. The serum, collected by bleeding from the ear 55 days after the initial injection, was used for immunoprecipitation analysis.

Immunoprecipitations were performed as follows: confluent cultured cells were infected with HSV at 10 pfu/cell (10 plaque forming units/cell) and labeled with $^{35}$S-methionine for 16 hours after infection. [GBK (Georgia Bovine Kidney) cells were infected with HSV-1 whereas HeLa cells were infected with HSV-2; Vero cells were infected with either HSV-1 or HSV-2]Lysates of the $^{35}$S-methionine-labeled HSV-infected cells were incubated with 10 μl of either pre-immune rabbit sera, rabbit antisera directed against the pEH4-2 fusion protein (e.g., 018 or 019 antisera) or with 1 μl monoclonal antibody 4S. The immune complexes were collected using Pansorbin as described in Section 6.3.3. and the resulting radiolabeled immunoprecipitated proteins were resolved by SDS-PAGE and fluorographed. SDS-PAGE results demonstrated that: (1) a 52,000 dalton gD protein produced by HSV-1 infected GBK cells or Vero cells is immunoreactive with antisera directed against the fusion protein produced by pEH4-2 transformants and with 4S monoclonal antibody; (2) a 50,000 dalton gD protein produced by HSV-2 infected HeLa cells or Vero cells is immunoreactive with antisera directed against the pEH4-2 fusion protein and with 4S monoclonal antibody. The apparent lower molecular weight of gD derived from HSV-2 as compared to gD derived from HSV-1 is consistent with published observations (Ruyechan et al., 1979, J. Virol. 29:677). Results of fluorography demonstrated that the gD protein produced by either HSV-1 or HSV-2 infected cells is immunoreactive with the antisera directed against the fusion protein produced by pEH4-2 transformants.

6.4.3. Antisera Directed Against pEH4-2 Neutralizes HSV-1 and HSV-2 Infection in Vitro The rabbit antisera directed against the pEH4-2 fusion protein were also analyzed for their ability to neutralize virus infectivity. Virus neutralization was assayed by a reduction in plaque numbers in infected cells in tissue culture (Showalter et al., 1981, Infection and Immunity 34:684). To this end 50 to 100 pfu of HSV-1 or HSV-2 were pre-incubated with dilutions of pre-immune sera (control), immune antisera (018 or 019) or monoclonal antibody 4S in the presence or absence of active serum complement (C'). Vero cells were infected with these preparations of HSV-1 or HSV-2. After three to four days the HSV plaques were counted and the effect of antiserum on reduction of plaque numbers was determined. The results shown in Table 1 demonstrate that antisera from each rabbit was capable of neutralizing HSV-1 and HSV-2 in vitro. Neutralization was evident in the absence of active complement although complement markedly increased neutralization activity. Neutralization was more effective against HSV-1 than HSV-2.

TABLE 1

HSV NEUTRALIZATION BY ANTI-pEH4-2 FUSION PROTEIN

| | Neutralization[1] | | | |
|---|---|---|---|---|
| | HSV-1 | | HSV-2 | |
| ANITBODY | −C' | +C' | −C' | +C' |
| 018 | 128 | 768<br>512[2]<br>200+[2] | 8 | 32 |
| 019 | 128 | 512<br>256[2]<br>200[2] | 12 | 32 |
| Monoclonal | 20,000+ | 20,000+ | 20,000+ | 20,000+ |

[1]Serum from rabbits on 018 and 019 was tested for virus neutralization in the presence of 5% heat inactivated complement (56° C. for 30 minutes, −C',) or active guinea pig complement (+C') on Vero cell monolayers. Numbers represent the antibody titer as the reciprocal of the serum dilution which reduced plaque numbers by 50%.
[2]In these trials GBK cells were used instead of vero cells.

The results presented demonstrate the utility of the pEH4-2 fusion protein in a subunit vaccine against HSV-1 and HSV-2.

6.4.4. Reconstruction of the gD-1 Gene in pEH4-2

The plasmids pJS413 and pRWF6 were used to reconstruct the gD-1 gene (FIG. 8).

Accordingly, pRWF6 was digested with HindIII and Bal 31 to generate a spectrum of randomly sized blunt-ended fragments. After digestion of these fragments with SacI, the blunt-ended/SacI fragments ranging from 2.2 to 2.4 kb were isolated. These fragments contained varying lengths of the amino-coding terminus of the gD-1 gene (see FIG. 8).

The gD-1 fragments were subcloned into pJS413. To this end, pJS413 was digested with SmaI (resulting in a blunt end) and SacI (resulting in a SacI 3'-cohesive end). The 4.7 kb SmaI/SacI pJS413 fragment was ligated with the blunt-ended/SacI pRWF6 fragment (2.2–2.4 kb) in a 1:1 ratio and used to transform E. coli strain NF1829. This resulted in a population of clones transformed with plasmids which contained the gD-1 gene randomly "deleted" at its amino-coding terminus (FIG. 8). In all, 24 plasmids, labeled pEH50+x (wherein x stands for 1 through 24), approximately 7 kb each, were analyzed by mapping the restriction enzyme recognition sites. Those which contained a PvuII site within the gD-1 gene (19 out of the 24 transformants) were further analyzed in order to identify the clone which contained the largest portion of the amino-coding terminus of gD-1.

In a complete gD-1 gene sequence, the distance between the gD initiation ATG and the internal PvuII site is 156 base pairs. Thus, each of the 19 pEH50+x plasmids was digested with BflII and PvuII; the resulting fragments were resolved by gel electrophoresis in order to determine the size of the BGlII/PvuII fragment. Fifteen pEH50+x plasmids having a BglII/PvuII fragment smaller than 160 base pairs were identified, i.e., the end point of the Bal 31 digestion depicted in FIG. 8 was somewhere between the gD-1 initiation ATG and the PvuII site. These fifteen were sequenced to precisely determine the site of ligation to the pJS413 plasmid. Seven plasmids, pEH51, pEH60, pEH62, pEH66, pEH73 and pEH74, contained the gD-1 sequence ligated in phase with the translational reading frame of the cro ATG of pJS413 (see FIG. 3 where these ligation sites are indicated by the corresponding pEH number and a vertical arrow). In fact, pEH51 encodes all but the first 6 amino acids of the gD-1 amino-terminus.

Transformants of pEH51, pEH60, pEH62 and pEH71 were labeled with $^{35}$S-methionine with or without IPTG induction and cell lysates were treated with monoclonal antibody 55S; the immunoprecipitates were analyzed by SDS-PAGE as previously described. Transformants containing pEH51, pEH60, pEH62 or pEH71 each produced a 46,000 dalton inducible protein which precipitated with monoclonal 55S (data not shown).

Finally, recombinant plasmids which encode fusion proteins were made using the amino-coding terminus of pEH51 to reconstruct the amino-coding terminus of the gD-1 gene sequence present in pEH4-2 (see FIG. 9). The plasmid pEH4-2 was digested with PstI and SacII and the 6.2 kb fragment containing the partial gD-1/β-galactosidase gene was isolated. The plasmid pEH51 was totally digested with PstI, but partially digested with SacII. The 1.25 kb PstI/SacII fragment of pEH51 was ligated in a 1:1 ratio with the 6.2 kb PstI/SacII fragment of pEH4-2 to form pEH82. Transformants were identified by screening for β-galactosidase activity as previously described. E. coli transformants bearing the pEH51 plasmid are designated E coli strain WW51; those transformants bearing the pEH82 plasmid are designated E. coli strain WW82.

We have shown that HSV gD-1 fusion proteins can be produced in quantity in E. coli. The fusion proteins are very stable perhaps due to the fusion protein construction itself or to the sequestering of the fusion protein in dense, insoluble inclusion bodies. We have demonstrated that the fusion protein can be extracted from E. coli and can be used to immunize animals. The antisera produced is capable of neutralizing plaque formation of both HSV-1 and HSV-2 in vitro.

6.5. Preparation of pEH9010am LE392 which Produces Both CRO/gD-1 and CRO/gD-1/β-Galactosidase Fusion Protein A recombinant plasmid, pEH90-10am, was constructed which can direct the production of both a fused and unfused gD-1 related protein in appropriate host cells (see FIG. 10).

The pEH90-10am plasmid was derived from a series of recombinant plasmids, pEH-90-N, that, in turn were derived from pEH3-25 (isolated in Section 6.4) which encodes a Cro/gD-1/β-galactosidase fusion protein (see FIG. 3 and FIG. 10). The pEH-90-N series is similar to pEH4-2 (Section 6.4) in that the translational reading frames of cro, gD-1, and the z-gene are in phase, however, the pEH-90-N series contains additional unique restriction endonuclease recognition sequences located at the junction of the gD-1 gene and the z-gene.

The recombinant plasmid isolated from one transformant of the pEH-90-N series, designated pEH-90-10, was further modified as follows: (1) pEH-90-10 was cleaved at the junction of the gD-1 gene sequence and the z-gene sequence; (2) pEH-90-10 was then ligated in the presence of DNA linker sequences containing the amber chain termination sequence, TAG. The resulting recombinant plasmid, pEH-90-10am, contains an amber chain termination sequence in phase with the translational reading frames of both the gD-1 gene and the z-gene.

When pEH90-10am was used to transform E. coli NF1829, the ampicillin resistant transformants synthesized no detectable fusion protein. However, when the pEH90-10am transformant was infected with the lysogenic transducing phage, φ80 SuIII, carrying an amber suppressor tRNA gene, then the induced transformants produced a Cro/gD-1/β-galactosidase fusion protein. The lysogens are designated pEH90-10am SuIII.

Alternatively, the pEH90-10am plasmid was used to transform E. coli LE392 which carries two amber suppressor mutations (SupE and SupF). The pEH90-10am LE392 transformants produced a Cro-gD-1/βgalactosidase fusion protein under both induced and non-induced conditions. (LE392 cells do not have the lac I$^Q$ mutation of NF1829 which results in overproduction of lac repressor). SDS-PAGE analysis of the proteins produced by the pEH90-10am LE392 transformants revealed that both a fusion protein (approximately 160,000 daltons) and an unfused gD-1 related protein (approximately 38,000 daltons) were produced; both proteins immunoreact with rabbit anti-HSV-1 serum. The pEH90-10am LE392 transformants seem to produce both proteins in approximately equimolar amounts, and the two proteins co-purify when isolated via the non-denaturing co-aggregate purification procedure described in Section 5.5. Details of the procedure are described in the subsections below.

6.5.1. Preparation of the pEH90-N Series

As previously explained in Section 6.4, pEH3-25 transformants produce a Cro/gD-1/β-galactosidase fusion protein, albeit in lesser amounts than do pEH4-2 transformants. The pEH3-25 recombinant plasmid is similar to pEH4-2 except that pEH3-25 contains the transmembrane sequence of gD-1 (see FIG. 3). The transmembrane sequence may be responsible for the inefficient expression of fusion protein in host cell transformants.

The expression vector pHK414 (FIG. 10) is a pJS413 derivative. In fact, pHK414 contains all the elements of pJS413 but differs in its unique cloning sites across the cro-z junction. The cloning sites of pHK414 are: BglII, HindIII, SmaI, BamHI. The z-gene is not in phase with the cro ATG, thus, the intact plasmid does not direct the production of β-galactosidase. However, when a DNA fragment of the appropriate length (3n+2) is inserted into any of these cloning sites on the plasmid, the reading frame of the z-gene is readjusted with respect to the cro ATG and, provided that the inserted DNA sequence contains no termination signals (e.g., TGA, TAA, or TAG) that are in phase with the cro ATG or z-gene, a β-galactosidase fusion protein will be produced by host cell transformants.

The pEH90-N series was constructed as follows (see FIG. 10): pEH3-25 was first digested with BamHI; the cleaved plasmid was then treated with Bal31 in order to remove the gD-1 transmembrane sequence at the carboxy-coding terminus. After the Bal31 digestion, pEH3-25 was cleaved with PstI and a population of DNA fragments ranging from 1.7 to 1.9 kb characterized by a PstI cohesive end, the amino-coding terminus of the amp$^r$ gene, the lac promoter and translational control elements, the gD-1 gene, with deletions of all or part of the transmembrane sequence, and a blunt end (BamHI$^{(-)}$) was isolated by agarose gel electrophoresis.

The expression plasmid, pHK414 was first cleaved with BglII and the BglII cohesive ends were filled in using the Klenow fragment of DNA polymerase. The linear blunt-ended pHK414 was then digested with PstI and a 5.5 kb DNA fragment characterized by a blunt end (BglII$^{(-)}$), the z gene, the carboxy-coding terminus of the amp$^r$ gene, and a PstI cohesive end was isolated by agarose gel electrophoresis.

The 1.7 to 1.9 kb PstI/BamHI$^{(-)}$ DNA fragments of pEH3-25 and the 5.5 kb BglII$^{(-)}$/PstI DNA fragment of pHK414 were ligated in a 1:1 molar ratio using T4 DNA ligase. The resulting population of plasmids, designated pEH90-N, were used to transform E. coli NF1829 which were grown on indicator agar plates.

The following recombinant plasmids derived from 10 of the 24 transformants which produced fusion proteins were analyzed by DNA sequencing across the gD-1/z-gene junction (see FIG. 2): pEH90-2, pEH90-3, pEH90-4, pEH90-5, pEH90-6, pEH90-7, pEH90-9, pEH90-10, pEH90-11, and pEH90-12. All except pEH90-12 contain deletions of all or part of the transmembrane sequence; pEH90-4 and pEH90-5 contain approximately half of the transmembrane sequence. Each of these plasmids, with the exception of pEH90-12, directed the production of a Cro/gD-1/β-galactosidase fusion protein at the high level produced by pEH4-2. Plasmid pEH90-10 was selected for the next step in the procedure (the gD-1 fusion protein produced by pEH90-10 transformants is identical to that produced by pEH4-2 transformants except that the last 4 amino acids of gD-1 produced by pEH4-2 transformants are missing from the fusion protein produced by pEH90-10 transformants).

6.5.2. Preparation of pEH90-10am

In order to introduce an amber chain termination sequence between the gD-1 sequence and the z-gene of the pEH90-10 plasmid the following procedure was used (see FIG. 10): pEH90-10 was cleaved with HindIII followed by BamHI resulting in cleavage of the plasmid at its unique restriction endonuclease sites located at the junction between the gD-1 gene and the z gene (see below):

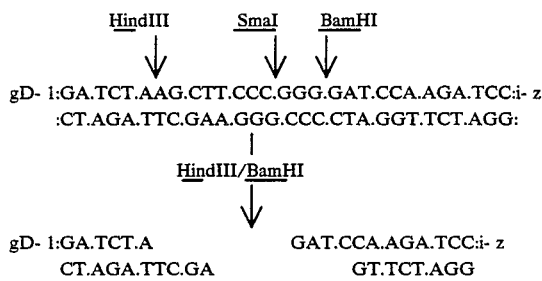

The 7.3 kb HindIII/BamHI cleaved plasmid was isolated by agarose gel electrophoresis and ligated (using T4 DNA ligase) with a DNA linker characterized by HindIII/BamHI cohesive ends and an internal XbaI site and amber sequence (TAG):

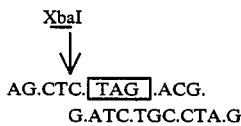

Each complementary strand of the DNA linker was synthesized by the solid phase method reported by Chow et al., 1981, Nucleic Acids Res 9(12): 2807–2817.

After ligation of the linker to the cleaved plasmid, the resulting recombinant plasmids were cleaved with XbaI, the linear 7.3 kb DNA fragments were isolated by agarose gel electrophoresis and recircularized by ligation with T4 DNA ligase (this selected for the pEH90-10 plasmids that, in fact, contained the linker sequence ligated between the HindIII and BamHI sites at the gD-1/z junction which is indicated by the presence of a single XbaI site on the plasmid). As a result of ligation, the amber sequence of the DNA linker was in phase with the translational reading frame of gD-1 and the z gene (see below):

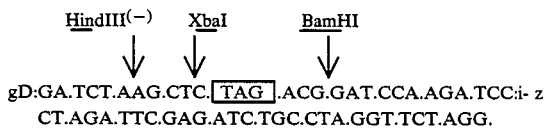

The resulting plasmid was designated pEH90-10am.

6.5.3. pEH90-10am Transformants

The pEH90-10am plasmid was used to transform *E. coli* NF1829. When induced with IPTG, the ampicillin resistant transformants synthesized no detectable levels of fusion protein (no red colonies on MacConkey indicator agar plates). The transformants were then infected with the lysogenic transducing phage, φ80 SuIII, which carries an amber suppressor tRNA gene. The lysogenized transformants induced with IPTG produced red colonies on MacConkey agar plates, indicating fusion protein production. These lysogens were designated pEH90-10am SuIII.

The pEH90-10am plasmid was also to transform *E. coli* LE392 which carries two amber suppressors (supE and supF) but does not have the lac I$^Q$ mutation of NF1829 and therefore does not oversynthesize lac repressor. These transformants, designated pEH90-10am LE392 produced a fusion protein whether or not induced by IPTG.

6.5.4. Analysis of Proteins Produced by pEH90-10am LE392 Transformants

The fusion protein (approximately 160,000 daltons) and a 38,000 dalton protein were produced by pEH90-10am LE392 transformants in approximately equimolar amounts. Each protein was shown to immunoreact with rabbit antiserum directed against HSV-1. To this end, cell proteins were isolated by a mini-aggregate procedure (described below), separated by SDS-PAGE, and transferred to nitrocellulose which was then treated with rabbit antiserum directed against HSV-1 followed by $^{125}$I-labeled goat antiserum directed against rabbit immunoglobulin as a probe (Towbin et al., 1979, Proc. Natl. Acad. Sci., U.S.A. 76:4350).

The following mini-aggregate procedure was used to isolate host cell aggregates for screening analysis:

(1) Duplicate culture tubes containing 5 ml of fresh Luria broth containing 100 μg/ml ampicillin were inoculated with 200 μl of cells obtained from an overnight culture and grown for 90 minutes at 37° C. One of each duplicate was induced by the addition of 1 mM IPTG (final concentration). The inocula were then grown with shaking, for a further 5 hours at 37° C.

(2) The cells contained in a 3 ml aliquot of the culture were pelleted by centrifugation in a microcentrifuge (12,000 × g) for 2 minutes. (N.B., the total volume of a microcentrifuge tube is 1.5 ml, therefore, a 1.5 ml aliquot was first pelleted and the supernatant was drawn off; another 1.5 ml aliquot was added to the same microcentrifuge tube and pelleted in the same tube.)

(3) The cell pellet was resuspended in 50 μl of 25% sucrose containing 50 mM Tris-HCl, pH8, and the suspension was frozen by placing the tube in a dry ice/ethanol bath.

(4) The frozen suspension was thawed, 50 μl of 10 mg/ml lysozyme in 0.25M Tris-HCl pH8 was added, and the suspension was incubated for 10 to 15 minutes on ice.

(5) After the 10 to 15 minute incubation 400 μl of TET buffer (100 mM Tris- HCl pH8, 50 MM EDTA, 2% Triton X-100; Triton-100 is a non-ionic detergent: polyoxyethylene (0–10) p-tert-octyl phenol) was added, the suspension was gently mixed and incubated for 5 minutes on ice. Then 500 μl of 2xRIPA (2xRIPA is 20 mM Tris-HCl, pH7.4, 300 mM NaCl, 2% sodium deoxycholate, 2% NP-40, 0.2% SDS) was added and the suspension was mixed gently and incubated for 5 minutes on ice.

(6) The cells in the suspension were then sonicated for 10 seconds using a microprobe, and the suspension was cleared by centrifugation in a Sorvall SS34 rotor for 30 minutes at 20,000 r.p.m. (47,800× g).

(7) The supernatant was decanted and the pellet, which contains the co-aggregate proteins, was resuspended in 50 μl distilled H₂O to which 50 μl of 2× Sample Buffer (2× Sample Buffer is composed ot 10% SDS, 40 mM Tris-HCl, pH6.8, 2% β-ME, and 0.02 volumes saturated solution of bromphenol blue) was added and mixed well. The mixture was boiled for 5 minutes and 25 μl aliquots were applied to 10% SDS-polyacrylamide gels for electrophoresis.

After the proteins were separated by SDS-PAGE, they were transferred to nitrocellulose (i.e., a protein "blot" was done). The nitrocellulose was then treated with rabbit antisera directed against HSV-1 followed by $^{125}$I-labeled goat antiserum directed against rabbit immunoglobulin as a probe (Towbin, 1979 supra). Autoradiograms of the protein blots clearly demonstrated that two bands immunoreacted with the anti-HSV-1 antibodies: a 160,000 dalton fusion protein (Cro/gD-1/β-galactosidase) and a 38,000 dalton gD-1 related protein (Cro/gD-1) or unfused gD protein (unfused to β-galactosidase). Thus, the unfused protein co-purifies with the fusion protein when the co-aggregate method of isolation is used for isolating proteins, and both the unfused gD (Cro/gD-1) and gD-fusion protein (Cro/gD-1/β-galactosidase) immunoreact with anti-HSV serum.

7. EXAMPLE: HSV-2 gD

The genomic map of HSV-1 was compared to that of HSV-2. The location of the gD coding sequence within the HSV-2 genome was determined by analogy to the position and size of gD within the HSV-1 genome. The BglII L fragment of the Us region of HSV-2 was inserted into pBR322 to form a recombinant plasmid, pHV1. The gD-2 coding sequence contained within pHV1 was localized by hybridization using a portion of gD-1 DNA obtained from pSC30-4 as a hybridization probe. The portion of pHV1 containing the gD-2 coding sequence was then subcloned into pBR322 to form recombinant plasmid pHV2. The DNA sequence of the gD-2 gene within pHV2 was determined and the sequence of gD-2 was compared to that of gD-1. The DNA sequence of gD-2 is one codon shorter than that of gD-1; however, there is considerable homology between the two sequences.

In order to place the gD-2 gene under lac promoter control, a portion of the gD-2 gene sequence lacking the first 120 nucleotides of the protein coding sequence was isolated from pHV2. This DNA fragment was ligated to a small DNA fragment encoding the lac promoter and translational control elements. The resulting recombinant plasmid, pHV5, directed the production of a gD-2 related protein in host cell transformants.

Finally, the gD-2 gene fragment was isolated from pHV5 by restriction endonuclease cleavage at specific sites so that the termination sequence (TAG) of the gD-2 coding sequence was deleted. This DNA fragment which contained a portion of the gD-2 gene and the expression plasmid promoter and control elements was ligated into pHK414, a vector containing a β-galactosidase coding sequence. The resultant recombinant plasmid, pHV6, which contained the gD-2 coding sequence sandwiched between the plasmid lac promoter with a cro SD-ATG and the β-galactosidase gene, directed the expression of a fusion protein in induced *E. coli* transformants. The pHV6 fusion protein was isolated from host cell lysates and formulated for use as an immunogen. A detailed description of each step in the construction is presented in the subsections below.

7.1. General procedures used for Preparation of the Plasmids

Unless otherwise indicated, the general methods described in Section 6 and its subsections for DNA isolation, enzyme reactions, and ligation reactions were utilized in the cloning of gD-2.

7.1.1. Restriction Enzyme Buffers

The buffer used for SmaI digestions consisted of: 6.6 mM Tris-HCl (pH 7.4), 6.6 mM MgCl₂ and 6.6 mM β-mE.

The buffer used for BglII, ClaI, EcoRI or PstI digestions consisted of: 60 mM NaCl, 6.6 mM Tris-HCl (pH7.4), 66.6 mM MgCl₂ and 6.6 mM β-mE.

The buffer used for BamHI, SalI, or XhoI digestions consisted of: 150 mM NaCl, 6.6 mM Tris-HCl (pH7.4), 6.6 mM MgCl₂ and 6.6 mM β-ME.

It should be noted that whenever two or more restriction endonuclease reactions are performed on DNA, the reaction in low salt buffer is accomplished before the reaction in high salt buffer. If two enzymes require the same buffer, then the reactions may be performed simultaneously.

7.2. Localization and Isolation of the gD-2 Gene

As explained previously, the genomic maps of HSV-1 and HSV-2 were compared in order to determine the approximate position and size of gD within the HSV-2 genome (see FIG. 11a). The gD-2 gene mapped between 0.9–0.945 genome map units within the Us region which is contained within the 8.5 kb BglII L fragment. The BglII L fragment was excised from the HSV-2 DNA and inserted into pBR322 for further analysis.

7.2.1. Construction of pHV1 Containing the gD-2 Gene

HSV-2 (strain G) genomic DNA was digested with BglII and a DNA fragment, approximately 8.5 kb, which contained the gD-2 gene was isolated by agarose gel electrophoresis. The plasmid pBR322 was totally digested with BamHI; the resultant 4.4 kb pBR322 DNA and the 8.5 kb BglII L DNA fragment of HSV-2 were annealed (BamHI cohesive ends and BglII cohesive ends are complementary) and ligated in a 1:1 ratio resulting in pHV1 (FIG. 11b).

7.2.2. Localization of gD-2 Specific mRNA Coding Sequence

The gD-2 mRNA coding sequence was localized within pHV1 by hybridization (Southern, 1975, J. Mol. Biol. 98: 503) using a portion of gD-1 DNA obtained from pSC30-4 as a hybridization probe (for the protocol used for Southern transfer see Maniatis et al., 1982, Molecular Cloning, A Laboratory Manual, Cold Spring Harbor Laboratory, pp. 382–389).

Accordingly, pHV1 was cleaved with XhoI and the resulting DNA fragments were separated by agarose gel electrophoresis. The DNA fragments in the gel were then denatured in alkali, neutralized, and transferred to a nitrocellulose filter. The DNA fragments attached to the filter were then hybridized to the $^{32}$P-labeled gD-1 probe.

The $^{32}$P-labeled gD-1 probe was prepared as follows: pSC30-4 (FIG. 1d and FIG. 4) was cleaved with PvuII and the 500 bp DNA fragment containing the first 52 condons (156 nucleotides) of gD-1 was isolated by polyacrylamide gel electrophoresis. The gD-1 DNA was radiolabeled by nick translation (BRL Kit, Bethesda Research Laboratories, Inc., Gaithersburg, MD). Nick translation is the method of choice for in vitro labeling of duplex DNA to high radiospecific activity. This method takes advantage of two of the several activities of E. coli DNA polymerase I: the 5' to 3' exonuclease activity and the 5' to 3' polymerase activity. In nick translation, the enzyme binds at a nick in one strand of duplex DNA. The 5' to 3' exonuclease activity then hydrolyzes nucleotides in the nicked strand, ahead of the advancing polymerase. The nick is thus moved (translated) along the strand. Since the rate of hydrolysis is equal to the rate of polymerization, there is no net synthesis. However, in the course of this exchange reaction, radioactive deoxynucleoside triphosphates present in the reaction mixture are incorporated into the DNA (Kelly et al., 1970, J. Biol. Chem. 245: 39). The $^{32}$P-labelled gD-1 duplex DNA was then denatured for use as a single-stranded probe. (see Maniatis et al., Molecular Cloning, A Laboratory Manual, Cold Spring Harbor Laboratories, pp. 109-112).

Autoradiography demonstrated that an XhoI/XhoI DNA fragment of pHV1, approximately 2.3 kb, was complementary to the radioactive gD-1 probe and, therefore, contained the gD-2 coding sequence.

The XhoI/XhoI DNA fragment of pHV1 was then subcloned into pBR322 in order to further characterized the gD-2 coding sequence. To this end, pHV1 was digested with XhoI and the 2.3 kb DNA fragment containing the gD-2 coding sequence was annealed and ligated in a 1:1 ratio to linear pBR322 which had been previously cleaved with SalI (SalI generated cohesive ends are complementary to XhoI generated cohesive ends) to form pHV2 (FIG. 11c).

7.2.3. Characterization of the gD-2 mRNA Coding Sequence

The HSV-DNA of pHV2 was sequenced using the method of Maxam and Gilbert (1980, Methods in Enzymology, 65: 499). FIG. 12 represents the DNA sequence obtained for the HSV-2 gD gene. The DNA sequence contained an open reading frame of 393 codons (1 codon less than the DNA coding sequence of gD-1) extending from an ATG at position 267. This site was suspected to be the initiator of the gD-2 gene and was shown to be so by the cloning of this putative gD-2 gene sequence in the expression vectors pJS413 and pHK413 (infra).

The predicted amino acid sequence of the gD-2 protein was compared to the predicted amino acid sequence of the gD-1 protein (FIG. 13). The two sequences are approximately 82% homologous; the non-homologous regions seem to occur in three regions: the leader sequence, transmembrane region, and the putative anchor region. The gD-2 protein is one amino acid residue shorter than the gD-1 protein.

7.3. Cloning and Expression of the gD-2 Gene

In order to place the gD-2 gene under lac promoter control, a portion of the putative gene sequence lacking the first 120 nucleotides at the amino-coding terminus (5'-end of the gene) was isolated from pHV2. The pHV2 DNA fragment was ligated to a small pJS413 DNA fragment (approximately 200 bp) containing the lac promoter, translation control elements, the cro ATG and 69 nucleotides of cro. The resulting recombinant plasmid, pHV5 (FIG. 14), contains all but the first 40 codons of the gD-2 sequence. In fact, pHV-5 actually encodes all but 15 amino acids of the mature gD-2 protein. Normally, the first 25 amino acid residues of gD-2 (the signal sequence) are cleaved when the natural gD-2 protein is processed. The construction of pHV5 is described below.

7.3.1. Construction of pHV5

The recombinant plasmid, pHV2, was digested with ClaI (see FIG. 14), and the resulting cohesive ends were filled in using the Klenow fragment of DNA polymerase. The blunt ended linear pHV2 was then cleaved with EcoRI. A 5.4 kb ClaI$^{(-)}$/EcoRI DNA fragment containing the amp$^r$ gene and all but 120 nucleotides of the gD-2 coding sequence was isolated by agarose gel electrophoresis.

The expression vector pJS413 (described in Section 6.3.1) was cleaved with SmaI and EcoRI. A 200 b.p. (0.2 kb) fragment encoding the lac promoter, SD$^z$, SD$^{cro}$, the cro ATG and 69 nucleotides of cro was isolated by polyacrylamide gel electrophoresis.

The 5.4 kb ClaI$^{(-)}$/EcoRI pHV2 DNA fragment and the 0.2 kb EcoRI/SmaI pJS413 DNA fragment were ligated in a 1:1 molar ratio using T4 DNA ligase. The resultant recombinant plasmid, pHV5, was used to transform E. coli strain NF1829.

7.3.2. Identification of Transformants That Express the gD-2 Gene

The plasmids isolated from the ampicillin resistant E. coli transformants were analyzed by restriction endonuclease mapping and for their ability to direct the expression of a gD-2 related polypeptide. Since the lac promoter was transcriptionally inactive in NF1829 (due to overproduction of the lac repressor) the gD-2 related protein could only be detected upon induction of the promoter with either 1 mM IPTG or 1-10 mM lactose.

The clone transformed with the recombinant plasmid designated pHV5 was found to produce an inducible gD-2 related protein. The inducible protein was found to be immunoprecipitated by rabbit antisera directed against HSV-2.

7.4. Preparation of pHV6 Which Directs the Production of a Cro/gD-2/β-Galactosidase Fusion Progein In order to produce a fusion protein the gD-2 sequence was ligated to a bacterial host gene sequence such that the translational reading frames were uninterrupted by termination signals. To this end the gD-2 coding sequence of pHV5 was cleaved so that the gD-2 termination signal (TAG) was deleted. The pHV5 DNA fragment containing the lac promoter, translational controls, and the Cro/gD-2 sequence was ligated to a pHK414 DNA fragment containing the z-gene. The resulting recombinant plasmid, pHV6 (FIG. 15), encodes a Cro/gD-2/β-galactosidase fusion protein.

7.4.1 Construction of pHV6

The plasmid pHV5 was digested with PstI and BamHI (see FIG. 15). A 1.75 kb PstI/BamHI pHV5 DNA fragment encoding a portion of the amino-coding terminus of the amp$^r$ gene, the lac promoter, SD$^z$, SD$^{cro}$, the cro ATG and cro/gD-2 was isolated by agarose gel electrophoresis.

The expression vector, pHK414, was digested with PstI and BamHI. A 5.54 kb BamHI/PstI pHK414 DNA fragment encoding the z gene and a portion of the carboxy-coding terminus of the amp$^r$ gene was isolated by agarose gel electrophoresis.

The 1.75 kg PstI/BamHI pHV5 DNA fragment and the 5.54 BamHI/PstI pHK414 DNA fragment were annealed and ligated in a 1:1 molar ratio and used to transform *E. coli* NF1829. The ampicillin resistant colonies were examined for fusion protein production by assaying for β-galactosidase activity on indicator agar plates. The positive colonies were tested for the presence of the Cro/gD-2/β-galactosidase fusion protein by SDS-PAGE analysis of total lysates of transformants induced with IPTG. A high level producer of a 160,000 dalton fusion protein was isolated and the plasmid derived from this transformant was designated pHV6.

The fusion protein produced by the *E. coli* clones transformed with pHV6 was shown to be inducible by IPTG and to be cross immunoreactive with both HSV-1 and HSV-2. The fusion protein produced contains 265 amino acid residues of the gD-2 protein.

7.4.2 Immunoprecipitation Analysis of Antisera Directed Against pHV6 Fusion Protein The pHV6 fusion protein was purified using the denaturing protocol described in Section 6.4.2 and was used to produce antisera in three rabits (R159, R160, R161) as follows: The *E. coli* clones transformed with pHV6 were grown to mid-log phase and induced with 1 mM IPTG. Four hours after induction the bacteria were pelleted by centrifugation, lysed with SDS-PAGE sample buffer and loaded on preparative SDS-polyacrylamide gels. After electrophoresis, the proteins were visualized by staining the outer lanes with coomassie blue dye; then the 160,000 dalton fusion protein band was sliced from the gel. The gel slice was immersed in liquid nitrogen, ground to a powder and then suspended in PBS. An equal volume of Freund's complete adjuvant was then added. After thorough mixing, the solution was injected subcutaneously into three New Zealand rabbits (R159, R160, and R161). Each rabbit was injected with 100 to 200 μg protein. After 28 days the rabbits were boosted with the same amount of fusion protein suspended in incomplete Freund's adjuvant. The animals were boosted five times (total) at 10 day intervals. The serum collected 55 days after the initial injection (i.e., after two boosts) was used for immunoprecipitation analysis.

Immunoprecipitations were performed as follows: confluent cells were infected with HSV at 10 pfu/cell (Vero cells were infected with HSV-1 whereas Hela cells were infected with HSV-2). Cells were labeled with $^{35}$S-methionine for 16 hours after infection. Lysates of the $^{35}$S-methionine-labeled HSV-1-infected Vero cells or HSV-2 infected Hela cells were incubated with 10 μl of either pre-immune rabbit sera, or rabbit antisera directed against the pHV6 fusion protein (i.e., R159, R160, or R161 antisera). The immune complexes were collected using Pansorbin as described in Section 6.3.3 and the resulting radiolabeled immunoprecipitated proteins were resolved by SDA-PAGE and fluorographed. SDS-PAGE results demonstrated that a 50,000 dalton gD protein produced by HSV-2 infected Hela cells is immunoreactive with antisera directed against the fusion protein produced by transformants. The R159 and R161 antisera are specific for gD-2 whereas the R160 antiserum immunoprecipitates both gD-1 (a 52,000 dalton gD protein produced by the HSV-1 infected Vero cells) and gD-2; therefore, R160 is "type-common". It should be noted that 018 (Section 6.4.2), which is directed against a gD-1 fusion protein encoded by pEH4-2, is also type common.

7.4.3. Herpes Simplex Virus Neutralization in Vitro

The above-described rabbit antisera directed against the pHV6 fusion protein was also used to determine its ability to neutralize infection by HSV in vitro. To this end, virus neutralization studies using a plaque assay were performed as previously described. Each dish (35 mm) of confluent cells was infected with 50 pfu of HSV (Vero cells were infected with HSV-1 whereas Hela cells were infected with HSV-2) which had been preincubated with control (pre-immune sera) or test antisera dilutions (the following antisera were tested: 018, R159, R160, R161). After 3 days the cells were fixed and stained and plaques were counted. Table 2 shows the results of two such experiments. Neutralization is expressed as the serum dilution required to give a 50% reduction in plaque number. Table 2 clearly shows that the antisera directed against the pHV6 fusion protein (R159, R160, and R161) are capable of neutralizing HSV-2 infection in vitro whereas antisera directed against the pEH4-2 fusion protein (018) is capable of neutralizing HSV-1 infection in vitro. Although 018 and R160 are type-common (based on immunoprecipitation data in Section 7.4.2) 018 l (anti-gD-1 fusion protein) is more effective at neutralizing HSV-1 in vitro and R160 (anti-gD-2 fusion protein) is more effective in neutralizing HSV-2 infection in vitro.

TABLE 2

| NEUTRALIZATION OF HSV-1 AND HSV-2 BY ANTISERA DIRECTED AGAINST pHV6 FUSION PROTEIN | | |
|---|---|---|
| | Neutralization[1] | |
| Antisera | HSV-1 | HSV-2 |
| 018 | 128 | 8 |
| R159 | 16 | 48 |
| R160 | 24 | 64 |
| R161 | 8 | 32 |

[1]Numbers represent the antibody titer as the reciprocal of the serum dilution which reduced plaque numbers by 50%. Assays were performed in the presence of serum complement.

7.4.4. Immunofluorescence Analysis of Antisera Directed Against pHV6 Fusion Protein Immunofluorescence assays were performed as follows: confluent cells were infected with herpes virus at 0.1 pfu/cell for 20 hours at 37° C. (Vero cells were infected with HSV-1 whereas Hela cells were infected with HSV-2). The cells were washed with PBS and then fixed for 90 seconds at room temperature with acetone:methanol (1:1). The fixative was removed and the cells were air dried. Then a 20 μl aliquot of each rabbit antisera (018, R159, R160, and R161) diluted 1:20 in PBS was applied to the cells on the plate as discrete drops on marked locations. After a 30 minute incubation at 37° C. the cells were rinsed with PBS and air dried. Then a 20 μl aliquot of fluorescein-conjugated swine anti-rabbit serum was applied to the marked locations. After a 30 minute incubation at 37° C. the cells were washed, air dried, mounted in glycerol and viewed under ultraviolet light using a u.v. microscope. The presence of fluorescence indicates that the rabbit antisera was immunoreactive with HSV infected cells. Results are shown in Table 3.

TABLE 3
CROSS IMMUNOREACTIVITY OF ANTI-FUSION PROTEIN SERA WITH CELLS INFECTED WITH HSV

| Antisera[1] | Immunofluorescence of HSV-Infected Cells[2] | |
|---|---|---|
| | HSV-1 | HSV-2 |
| 018 | +++ | + |
| R159 | + | + |
| R160 | + | ++ |
| R161 | + | ++ |

[1]Antisera were applied at a 1:20 dilution.
[2]+++ represents the most intense staining of cells.
++ represents an intermediate staining of cells.
+ represents a positive but less intense stain.

8. EXAMPLE: VACCINATION

8.1. Protection Against HSV-2 Infection in Vivo Using gD-1 Fusion Protein in a Vaccine Formulation Three groups of 10 Balb C mice each were injected intraperitoneally (I.P.) with the following preparations: Group 1 (unvaccinated control) received saline; Group 2 received 3 µg of native HSV-1 gD protein in complete Freunds adjuvant; and Group 3 received 30 µg of pEH4-2 fusion protein (isolated by the denaturing aggregate purification method described in Section 5.5) in saline. All groups received four injections, I.P.; each injection was administered at 2 week intervals and boosts contained 1 µg gD (Group 2) or 10 µg fusion protein.

The mice were bled retro-orbitally after the fourth injection and this sera was tested for neutralization of herpes virus in vitro (without complement) using the plaque assay previously described in Section 6.4.3. and Section 7.4.2.

One week after the fourth inoculation the mice were challenged with 10 LD$_{50}$ of HSV-2 strain 186. The HSV-2 was suspended in 0.5 ml and injected intraperitoneally. Survival of the challenged mice indicates protection. Results are shown in Table 4.

TABLE 4
VACCINATION AND PROTECTION OF MICE CHALLENGED WITH HSV-2

| | Protection Against HSV-2 Infection | |
|---|---|---|
| Vaccine | Survivors/Total | % Survivors |
| 1 (control) | 1/11 | 9 |
| 2 (native gD-1) | 10/10 | 100 |
| 3 (pEH4-2 fusion protein) | 8/10 | 80 |

8.2. Protection Against HSV-2 Infection in Vivo Using gD-2 Fusion Protein in a Vaccine formulation Four groups of 10 mice each were vaccinated with the following preparations: Group 1 (control) received pNB9-1 bovine growth hormone/β-galactosidase fusion protein; Group 2 received pEH4-2 Cro/gD-1/β-galactosidase fusion protein (see Section 6.4); Group 3 received pEH82 reconstructed Cro/gD-1/β-galactosidase fusion protein (see Section 6.5); and Group 4 received pHV6 Cro/gD-2/β-galactosidase fusion protein (see Section 7.4).

The fusion proteins were isolated from the various E. coli transformants by lysozyme/detergent disruption of induced transformants followed by pelleting the aggregates (the non-denaturing aggregate purification procedure as described in Section 5.5).

The immunization schedule was as follows: the Balb C mice (6–7 weeks old) were each inoculated intraperitoneally with 150–200 µg of non-denatured fusion protein in 0.2 ml saline. The mice were re-inoculated intraperitoneally (boosted) with 74–100 µg fusion protein three more times at two week intervals (a total of 4 inoculations). The mice were bled retro-orbitally after the fourth injection and this sera was tested for neutralization of herpes virus in vitro (without complement) using the plaque assay previously described in Section 6.4.3. and Section 7.4.2.

One week after the fourth inoculation the mice were challenged with 17 LD$_{50}$ of HSV-2 strain 186. The HSV-2 was suspended in 0.5 ml and injected intraperitoneally. Survival of the challenged mice indicates protection. Results are shown in Table 5.

TABLE 5
VACCINATION AND PROTECTION OF MICE CHALLENGED WITH HSV-2

| Vaccine[1] | Protection Against HSV-2 Infection | | Serum Neutralization of HSV[2] | |
|---|---|---|---|---|
| | Survivors Total | % Survivors | HSV-1 | HSV-2 |
| pNB9-1 (control) | 0/10 | 0 | <4 | <4 |
| pEH4-2 | 6/9 | 67 | 16 | 4 |
| pEH82 | 3/9 | 33 | 16 | <4 |
| pHV6 | 8/10 | 80 | <4 | 8 |

[1]Fusion proteins suspended in saline were inoculated I.P.
[2]Serum was tested for HSV-1 of HSV-2 neutralization without complement. Numbers represent the antibody titers expressed as the reciprocal of the serum dilution which reduced plaque numbers by 50%.

8.3. COMPARISON OF VACCINE FORMULATIONS

Mice were immunized with fusion protein preparations made from pEH4-2 and pEH90-10 am LE392 transformants in a mixture with different adjuvants described below. The resulting antisera were evaluated by their ability to immunoprecipitate proteins derived from HSV-1 infected cells in culture.

Fusion proteins were isolated from the pEH4-2 and pEH90-10 am LE392 transformants by the non-denaturing technique described in Section 8.2. Aggregates were resuspended by sonication (forming a slurry) and solubilized by the treatment in hot alkali as follows: 0.5M NaOH was added to the pellet of aggregates to a final concentration of 50 mM. The aggregates were solubilized by heating at 65° C. for 15 minutes; the solution was then cooled and Tris-HCl pH7.5 was added (final concentration 100 mM Tris-HCl).

The fusion protein preparations (slurry or hot alkali preparations) were mixed with the following adjuvants before inoculation: (1) L121 (Hunter et al., 1981, J. of Immunol. 127(3): 1244–1250; BASF Wyandotte Corporation, Wyandotte, Mich.) a pluronic polyol (2.5 mg was administered per animal); or (4) aluminum hydroxide gel (Reheis Chemical Company, Berkeley Heights, N.J.) at a final concentration of 0.2%.

These preparations were used to immunize mice (CD-1 strain) according to the following schedule: each mouse was given a primary injection of 100 µg fusion protein and re-injected with 50 µg fusion protein 22 days later. The fusion protein was suspended in a 0.2 ml total volume which was injected intramuscularly into each thigh. The mice were bled retro-orbitally 7 days after the last injection.

The sera collected were analyzed by immunoprecipitation as follows: lysates of $^{35}$S-methionine labeled HSV-1-infected Vero cell were incubated with 5 μl of mouse sera (anti pEH4-2 or anti pEH90-10 am LE392) preimmune sera (negative control) or monocolonal 4S (positive control) for 2 hours at 4° C., and 5 μl rabbit anti-mouse serum (Dako, 30 minutes at 4° C.). The immune complexes were collected using Pansorbin as described in Section 6.3.3. and the radiolabeled immunoprecipitated proteins were resolved by SDS-PAGE and fluorographed. Results of fluorography revealed that all mice that were immunized with the alkali-solubilized fusion protein (both pEH4-2 and pEH90-10am LE392) with the L121 adjuvant had a strong immune response. A weaker response with the alkali-solubilized pEH4-2 fusion protein administered with aluminum hydroxide was observed. The other mice appeared not to respond, as adjudged by this test.

9. DEPOSIT OF MICROORGANISMS

It is to be understood that all base pair sizes given for nucleotides are approximate and are used for purposes of description. Furthermore, it is apparent that many modifications and variations of this invention as hereinbefore set forth may be made without departing from the spirit and scope thereof. The specific embodiments described are given by way of example only and the invention is limited only by the appended claims.

The following *E. coli* strains carrying the listed plasmids have been deposited with the American Type Culture Collection, Rockville, Md., and have been assigned the listed accession numbers:

| *E. coli* Strain | Plasmid | Accession Number |
|---|---|---|
| K-12, MC1000, NF1829 (WW51) | pEH51 | ATCC 39,159 |
| K-12, MC1000, NF1829 (WW82) | pEH82 | ATCC 39,160 |

The following *E. coli* strains carrying the listed plasmids have been deposited with the Agricultural Research Culture Collection (NRRL), Peoria, Ill., and have been assigned the listed accession numbers:

| *E. coli* Strain | Plasmid | Accession Number |
|---|---|---|
| K-12, MC1000, NF1829 | pEH4-2 | NRRL B-15471 |
| K-12, MC1000, NF1829 | pHV5 | NRRL B-15449 |
| K-12, MC1000, NF1829 | pHV6 | NRRL B-15450 |
| K-12, LE392 | pEH90-10 am | NRRL B-15451 |
| K-12, MC1000 | pJS5413 | NRRL B-15237 |

The present invention is not to be limited in scope by the microorganisms deposited, since the deposited embodiments are intended as illustrations of several aspects of the invention. Indeeded, various modifications of the invention in addition to those shown and described herein will become apparent to those skilled in the art from the foregoing description and accompanying drawings. Such modifications are intended to fall within the scope of the appended claims.

We claim:

1. A process for producing a polypeptide comprising the amino acid sequence of a Herpes Simplex Virus type 2 gD glycoprotein or a fragment of said amino acid sequence, wherein said fragment comprises at least seven contiguous amino acids, said polypeptide containing at least one immunological and antigenic determinant of a Herpes Simplex Virus type 2 gD glycoprotein, comprising:
   (a) culturing a unicellular organism containing a recombinant vector comprising a DNA sequence coding for a polypeptide comprising the amino acid sequence of a Herpes Simplex Virus type 2 gD glycoprotein or a fragment of said amino acid sequence, wherein said fragment comprises at least seven contiguous amino acids, said polypeptide containing at least one immunological and antigenic determinant of a Herpes Simplex Virus type 2 gD glycoprotein, and said recombinant vector capable of being replicated in said unicellular organism and said unicellular organism capable of producing said polypeptide; and
   (b) isolating said polypeptide from the culture.

2. The process according to claim 1, wherein the DNA sequence codes for the gD glycoprotein of Herpes Simplex Virus type 2.

3. The process according to claim 1, wherein the recombinant vector was introduced into the unicellular organism by transformation.

4. The process according to claim 1, wherein the recombinant vector was introduced into the unicellular organism by transduction.

5. The process according to claim 1, wherein the recombinant vector was introduced into the unicellular organism by transfection.

6. The process according to claim 1, wherein the information contained in the DNA sequence was obtained from a Herpes Simplex Virus genome.

7. The process according to claim 1, wherein the information contained in the DNA sequence was obtained by isolating mRNA coding for a Herpes Simplex Virus type 2 gD glycoprotein and using reverse transcriptase to construct said DNA sequence having one strand complementary to the isolated mRNA.

8. The process according to claim 1, wherein the DNA sequence was obtained from a DNA vector containing a Herpes Simplex virus DNA sequence.

9. The process according to claim 1, wherein the unicellular organism is a eucaryotic organism.

10. The process according to claim 1, wherein the unicellular organism is a procaryotic organism.

11. The process according to claim 10, wherein the procaryotic organism is *Escherichia coli*.

12. The process according to claim 11, wherein the *Escherichia coli* has NRRL accession No. B-15449.

13. The process according to claim 11, wherein the *Escherichia coli* has NRRL accession No. B-15450.

14. The process according to claim 6, wherein the information contained in the DNA sequence was obtained from Herpes Simplex Virus type 2.

15. The process of claim 1, wherein the unicellular organism is a yeast.

16. A process for preparing a unicellular organism having a DNA sequence coding for a polypeptide comprising the amino acid sequence of a Herpes Simplex Virus type 2 gD glycoprotein or a fragment of said amino acid sequence, wherein said fragment comprises at least seven contiguous amino acids, said polypeptide containing at least one immunological and antigenic determinant of a Herpes Simplex Virus type 2 gD glycoprotein, comprising: introducing a recombinant vector into a unicellular organism, said recombinant vector comprising a DNA sequence coding for a polypeptide comprising the amino acid sequence of a Herpes Simplex Virus type 2 gD glycoprotein or a fragment of said amino acid sequence, wherein said fragment comprises at least seven contiguous amino acid, said polypeptide containing at least one immunological and antigenic determinant of a Herpes Simplex Virus type 2 gD glycoprotein, and said recombinant vector capable of being replicated in said unicellular organism and said unicellular organism capable of producing said polypeptide.

17. The process of claim 16, wherein at least one determinant is common to Herpes Simplex Virus type 1 and type 2.

18. A recombinant vector comprising the DNA sequence:

ATG GGG CGT TTG ACC TCC GGC GTC
GGG ACG GCG GCC CTG CTA GTT GTC
GCG GTG GGA CTC CGC GTC GTC TGC
GCC AAA TAC GCC TTA GCA GAC CCC
TCG CTT AAG ATG GCC GAT CCC AAT
CGA TTT CGC GGG AAG AAC CTT CCG
GTT TTG GAC CAG CTG ACC GAC CCC
CCC GGG GTG AAG CGT GTT TAC CAC
ATT CAG CCG AGC CTG GAG GAC CCG
TTC CAG CCC CCC AGC ATC CCG ATC
ACT GTG TAC TAC GCA GTC CTG GAA
CGT GCC TGC CGC AGC GTG CTC CTA
CAT GCC CCA TCG GAG GCC CCC CAG
ATC GTG CGC GGG GCT TCG GAC GAG
GCC CGA AAG CAC ACG TAC AAC CTG
ACC ATC GCC TGG TAT CGC ATG GGA
CAC AAT TGC GCT ATC CCC ATC ACG
GTT ATG GAA TAC ACC GAG TGC CCC
TAC AAC AAG TCG TTG GGG GTC TGC
CCC ATC CGA ACG CAG CCC CGC TGG
AGC TAC TAT GAC AGC TTT AGC GCC
GTC AGC GAG GAT AAC CTG GGA TTC
CTG ATG CAC GCC CCC GCC TTC GAG
ACC GCG GGT ACG TAC CTG CGG CTA
GTG AAG ATA AAC GAC TGG ACG GAG
ATC ACA CAA TTT ATC CTG GAG CAC
CGG GCC CGC GCC TCC TGC AAG TAC
GCT CTC CCC CTG CGC ATC CCC CCG
GCA GCG TGC CTC ACC TCG AAG GCC
TAC CAA CAG GGC GTG ACG GTC GAC
AGC ATC GGG ATG TTA CCC CGC TTT
ATC CCC GAA AAC CAG CGC ACC GTC
GCC CTA TAC AGC TTA AAA ATC GCC
GGG TGG CAC GGC CCC AAG CCC CCG
TAC ACC AGC ACC CTG CTG CCG CCG
GAG CTG TCC GAC ACC ACC AAC GCC
ACG CAA CCC GAA CTC GTT CCG GAA
GAC CCC GAG GAC TCG GCC CTC TTA
GAG GAT CCC GCC GGG ACG GTG TCT
TCG CAG ATC CCC CCA AAC TGG CAC
ATC CCG TCG ATC CAG GAC GTC GCG
CCG CAC CAC GCC CCC GCC GCC CCC
AGC AAC CCG GGC CTG ATC ATC GGC
GCG CTG GCC GGC AGT ACC CTG GCG
GCG CTG GTC ATC GGC GGT ATT GCG
TTT TGG GTA CGC CGC CGC GCT CAG
ATG GCC CCC AAG CGC CTA CGT CTC
CCC CAC ATC CGG GAT GAC GAC GCG
CCC CCC TCG CAC CAG CCA TTG TTT
TAC, or a subsequence thereof, which subsequence comprises at least 21 contiguous nucleotides of said sequence and codes on expression for a polypeptide having at least one immunological and antigenic determinant of a Herpes Simplex Virus type 2 gD glycoprotein, wherein said polypeptide comprises at least seven contiguous amino acids and said recombinant vector is capable of being replicated in a compatible host cell and capable of directing expression of the DNA sequence in said host cell to produce said polypeptide.

19. The recombinant vector of claim 18, wherein said DNA sequence is under the control of expression control elements.

20. The recombinant vector pHV5.

21. The recombinant vector of claim 18, further comprising the pBR322 replication origin.

22. The recombinant vector of claim 18, wherein said DNA sequence is connected in phase to a second DNA sequence coding for a protein.

23. The recombinant vector pHV6.

24. The recombinant vector of claim 22, wherein a translation termination signal is located between and in phase with said first and second DNA sequences.

25. The recombinant vector of claim 18, wherein at least one determinant is common to Herpes Simplex Virus type 1 and type 2.

26. A purified DNA sequence coding for a polypeptide comprising the amino acid sequence of a Herpes Simplex Virus type 2 gD glycoprotein or a fragment of said amino acid sequence, wherein said fragment comprises at least seven contiguous amino acids, said polypeptide containing at least one immunological and antigenic determinant of a Herpes Simplex Virus type 2 gD glycoprotein, in which such DNA sequence is free of Herpes Simplex Virus-coded translational stop signals in phase and 5' to the triplet signal coding for the first amino acid of said polypeptide.

27. The purified DNA sequence of claim 26, in which the sequence comprises ATG GGG CGT TTG ACC TCC GGC GTC
GGG ACG GCG GCC CTG CTA GTT GTC
GCG GTG GGA CTC CGC GTC GTC TGC
GCC AAA TAC GCC TTA GCA GAC CCC
TCG CTT AAG ATG GCC GAT CCC AAT
CGA TTT GCG GGG AAG AAC CTT CCG
GTT TTG GAC CAG CTG ACC GAC CCC
CCC GGG GTG AAG CGT GTT TAC CAC
ATT CAG CCG AGC CTG GAG GAC CCG
TTC CAG CCC CCC AGC ATC CCG ATC
ACT GTG TAC TAC GCA GTG CTG GAA
CGT GCC TGC CGC AGC GTG CTC CTA
CAT GCC CCA TCG GAG GCC CCC CAG
ATC GTG CGC GGG GCT TCG GAC GAG
GCC CGA AAG CAC ACG TAC AAC CTG
ACC ATC GCC TGG TAT CGC ATG GGA
GAC AAT TGC GCT ATC CCC ATC ACG
GTT ATG GAA TAC ACC GAG TGC CCC
TAC AAC AAG TCG TTG GGG GTC TGC
CCC ATC CGA ACG CAG CCC CGC TGG
AGC TAC TAT GAC AGC TTT AGC GCC
GTC AGC GAG GAT AAC CTG GGA TTC
CTG ATG CAC GCC CCC GCC TTC GAG
ACC GCG GGT ACG TAC CTG CGG CTA
GTA AAG ATA AAC GAC TGG ACG GAG
ATC ACA CAA TTT ATC CTG GAG CAC
CGG GCC CGC GCC TCC TGC AAG TAC
GCT CTC CCC CTG CGC ATC CCC CCG
GCA GCG TGC CTC ACC TCG AAG GCC
TAC CAA GAG GGC GTG ACG GTC GAC
AGC ATC GGG ATG TTA CCC CGC TTT
ATC CCC GAA AAC CAG CGC ACC GTC

```
GCC CTA TAC AGC TTA AAA ATC GCC
GGG TGG CAC GGC CCC AAG CCC CCG
TAC ACC AGC ACC CTG CTG CCG CCG
GAG CTG TCC GAC ACC ACC AAC GCC
ACG CAA CCC GAA CTC GTT CCG GAA
GAC CCC GAG GAC TCG GCC CTC TTA
GAG GAT CCC GCC GGG ACG GTG TCT
TCG CAG ATC CCC CCA AAC TGG CAC
ATC CCG TCG ATC CAG GAC GTC GCG
CCG CAC CAC GCC CCC GCC GCC CCC
AGC AAC CCG GGC CTG ATC ATC GGC
GCG CTG GCC GGC AGT ACC CTG GCG
GCG CTG GTC ATC GGC GGT ATT GCG
TTT TGG GTA CGC CGC CGC GCT CAG
ATG GCC CCC AAG CGC CTA CGT CTC
CCC CAC ATC CGG GAT GAC GAC GCG
CCC CCC TCG CAC CAG CCA TTG TTT
TAC,
``` or subsequence thereof, which subsequence comprises at least 21 contiguous nucleotides of said sequence and codes on expression for a polypeptide having at least one immunological and antigenic determinant of a Herpes Simplex Virus type 2 gD glycoprotein.

28. The purified DNA sequence of claim 26 in which the determinant is specific to Herpes Simplex Virus type 2.

29. The purified DNA sequence of claim 26, in which the determinant is common to Herpes Simplex Virus type 1 and type 2.

30. A unicellular organism containing the exogenous DNA sequence:

```
ATG GGG CGT TTG ACC TCC GGC GTC
GGG ACG GCG GCC CTG CTA GTT GTC
GCG GTG GGA CTC CGC GTC GTC TGC
GCC AAA TAC GCC TTA GCA GAC CCC
TCG CTT AAG ATG GCC GAT CCC AAT
CGA TTT CGC GGG AAG AAC CTT CCG
GTT TTG GAC CAG CTG ACC GAC CCC
CCC GGG GTG AAG CGT GTT TAC CAC
ATT CAG CCG AGC CTG GAG GAC CCG
TTC CAG CCC CCC AGC ATC CCG ATC
ACT GTG TAC TAC GCA GTG CTG GAA
CGT GCC TGC CGC AGC GTG CTC CTA
CAT GCC CCA TCG GAG GCC CCC CAG
ATC GTC CGC GGG GCT TCG GAC GAG
GCC CGA AAG CAC ACG TAC AAC CTG
ACC ATC GCC TGG TAT CGC ATG GGA
GAC AAT TGC GCT ATC CCC ATC ACG
GTT ATG GAA TAC ACC GAG TGC CCC
TAC AAC AAG TCG TTG GGG GTC TGC
CCC ATC CGA ACG CAG CCC CGC TGG
AGC TAC TAT GAC AGC TTT AGA GCC
GTC AGC GAG GAT AAC CTG GGA TTC
CTG ATG CAC GCC CCC GCC TTC GAG
ACC GCG GGT ACG TAC CTG CGG CTA
GTG AAG ATA AAC GAC TGG ACG GAG
ATC ACA CAA TTT ATC CTG GAG CAC
CGG GCC CGC GCC TCC TGC AAG TAC
GCT CTC CCC CTG CGC ATC CCC CCG
GCA GCG TGC CTC ACC TCG AAG GCC
TAC CAA CAG GGC GTG ACG GTC GAC
AGC ATC GGG ATG TTA CCC CGC TTT
ATC CCC GAA AAC CAG CGC ACC GTC
GCC CTA TAC AGC TTA AAA ATC GCC
GGG TGG CAC GGC CCC AAG CCC CCG
TAC ACC AGC ACC CTG CTG CCG CCG
GAG CTG TCC GAC ACC ACC AAC GCC
ACG CAA CCC GAA CTC GTT CCG GAA
GAC CCC GAG GAC TCG GCC CTC TTA
GAG GAT CCC GCC GGG ACG GTG TCT
TCG CAG ATC CCC CCA AAC TGG CAC
ATC CCG TCG ATC CAG GAC GTC GCG
CCG CAC CAC GCC CCC GCC GCC CCC
AGC AAC CCG GGC CTG ATC ATC GGC
GCG CTG GCC GGC AGT ACC CTG GCG
GCG CTG GTC ATC GGC GGT ATT GCG
TTT TGG GTA CGC CGC CGC GCT CAG
ATG GCC CCC AAG CGC CTA CGT CTC
CCC CAC ATC CGG GAT GAC GAC GCG
CCC CCC TCG CAC CAG CCA TTG TTT
TAC,
``` or a subsequence thereof, which subsequence comprises at least 21 contiguous nucleotides of said sequence and codes on expression for a polypeptide having at least one immunological and antigenic determinant of a Herpes Simplex Virus type 2 gD glycoprotein, wherein said polypeptide comprises at least seven contiguous amino acids and said unicellular organism is capable of expressing the DNA sequence to produce said polypeptide.

31. A unicellular organism containing a recombinant vector comprising the DNA sequence:

```
ATG GGG CGT TTG ACC TCC GGC GTC
GGG ACG GCG GCC CTG CTA GTT GTC
GCG GTG GGA CTC CGC GTC GTC TGC
GCC AAA TAC GCC TTA GCA GAC CCC
TCG CTT AAG ATG GCC GAT CCC AAT
CGA TTT CGC GGG AAG AAC CTT CCG
GTT TTG GAC CAG CTG ACC GAC CCC
CCC GGG GTC AAG CGT GTT TAC CAC
ATT CAG CCG AGC CTG GAG GAC CCG
TTC CAG CCC CCC AGC ATC CCG ATC
ACT GTG TAC TAC GCA GTG CTG GAA
CGT GCC TGC CGC AGC GTG CTC CTA
CAT GCC CCA TCG GAG GCC CCC CAG
ATC GTC CGC GGG GCT TCG GAC GAG
GCC CGA AAG CAC ACG TAC AAC CTG
ACC ATC GCC TGG TAT CGC ATG GGA
GAC AAT TGC GCT ATC CCC ATC ACG
GTT ATG GAA TAC ACC GAG TGC CCC
TAC AAC AAG TCG TTG GGG GTC TGC
CCC ATC CGA ACG CAG CCC CGC TGG
AGC TAC TAT GAC AGC TTT AGC GCC
GTC AGC GAG GAT AAC CTG GGA TTC
CTG ATG CAC GCC CCC GCC TTC GAG
ACC GCG GGT ACG TAC CTG CGG CTA
GTG AAG ATA AAC GAC TGG ACG GAG
ATC ACA CAA TTT ATC CTG GAG CAC
CGG GCC CGC GCC TCC TGC AAG TAC
GCT CTC CCC CTG CGC ATC CCC CCG
GCA GCG TGC CTC ACC TCG AAG GCC
TAC CAA CAG GGC GTG ACG GTC GAC
AGC ATC GGG ATG TTA CCC CGC TTT
ATC CCC GAA AAC CAG CGC ACC GTC
GCC CTA TAC AGC TTA AAA ATC GCC
GGG TGG CAC GGC CCC AAG CCC CCG
TAC ACC AGC ACC CTG CTG CCG CCG
GAG CTG TCC GAC ACC ACC AAC GCC
ACG CAA CCC GAA CTC GTT CCG GAA
GAC CCC GAG GAC TCG GCC CTC TTA
GAG GAT CCC GCC GGG ACG GTG TCT
TCG CAG ATC CCC CCA AAC TGG CAC
ATC CCG TCG ATC CAG GAC GTC GCG
CCG CAC CAC GCC CCC GCC GCC CCC
AGC AAC CCG GGC CTG ATC ATC GGC
GCG CTG GCC GGC AGT ACC CTG GCG
```

```
GCG CTG GTC ATC GGC GGT ATT GCG
TTT TGG GTA CGC CGC CGC GCT CAG
ATG GCC CCC AGG CGC CTA CGT CTC
CCC CAC ATC CGG GAT GAC CAC GCG
CCC CCC TCG CAC CAG CCA TTG TTT
TAC,
```
or a subsequence thereof, which subsequence comprises at least 21 contiguous nucleotides of said sequence and codes on expression for a polypeptide having at least one immunological and antigenic determinant of Herpes Simplex Virus type 2 gD glycoprotein, wherein said polypeptide comprises at least seven contiguous amino acids and said recombinant vector is capable of being replicated in said unicellular organism and said unicellular organism is capable of expressing the DNA sequence to produce said polypeptide.

32. The unicellular organism of claim 31, wherein said DNA sequence is under the control of expression control elements.

33. The unicellular organism of claim 31, wherein said recombinant vector further comprises the pBR322 replication origin.

34. The unicellular organism of claim 31, wherein said DNA sequence is connected in phase to a second DNA sequence coding for a protein.

35. The unicellular organism of claim 31, wherein a translation termination signal is located between and in phase with said first and second DNA sequences and said unicellular organism contains the corresponding translation termination suppressor tRNA.

36. An *Escherichia coli* bacterium as deposited with the NRRL and assigned accession No. B- 15449.

37. An *Escherichia coli* bacterium as deposited with the NRRL and assigned accession No. B- 15450.

38. A recombinant vector comprising a DNA sequence coding for a polypeptide comprising the amino acid sequence of a Herpes Simplex Virus type 2 gD glycoprotein or a fragment of said amino acid sequence, wherein said fragment comprises at least seven contiguous amino acids, said polypeptide containing at least one immunological and antigenic determinant of a Herpes Simplex Virus type 2 dG glycoprotein, wherein the recombinant vector is capable of being replicated in a compatible host cell and capable of directing expression of the DNA sequence in said host cell to produce said polypeptide.

39. The recombinant vector of claim 38, further comprising the pBR322 replication origin.

40. The recombinant vector of claim 38, in which the DNA sequence is connected in phase to a second DNA sequence coding for a protein.

41. A unicellular organism containing an exogenous DNA sequence coding for a polypeptide comprising the amino acid sequence of a Herpes Simplex Virus type 2 gD glycoprotein or a fragment of said amino acid sequence, wherein said fragment comprises at least seven contiguous amino acids, said polypeptide containing at least one immunological and antigenic determinant of a Herpes Simplex Virus type 2 gD glycoprotein, wherein the unicellular organism is capable of expressing the DNA sequence to produce said polypeptide.

42. A unicellular organism containing a recombinant vector comprising a DNA sequence coding for a polypeptide comprising the amino acid sequence of a Herpes Simplex Virus type 2 gD glycoprotein or a fragment of said amino acid sequence, wherein said fragment comprises at least seven contiguous amino acids, said polypeptide containing at least one immunological and antigenic determinant of a Herpes Simplex Virus type 2 gD glycoprotein, wherein said recombinant vector is capable of being replicated in said unicellular organism and said unicellular organism is capable of expressing the DNA sequence to produce said polypeptide.

43. The unicellular organism of claim 41 or 42, wherein at least one determinant is common to Herpes Simplex Virus type 1 and type 2.

44. The unicellular organism of claim 41 or 42, wherein the unicellular organism is a yeast.

45. The unicellular organism of claim 43, wherein the unicellular organism is a yeast.

46. The unicellular organism of claim 42, in which the DNA sequence in such recombinant vector is under the control of a transcription promoter and translation initiation signal.

47. The unicellular organism of claim 42, in which such recombinant vector further comprises the pBR322 replication origin.

48. The unicellular organism of claim 42, in which the DNA sequence in such recombinant vector is connected in phase to a second DNA sequence coding for a protein.

49. A eucaryotic cell containing an exogenous DNA sequence coding for a polypeptide comprising the amino acid sequence of a Herpes Simplex Virus type 2 dG glycoprotein or a fragment of said amino acid sequence, wherein said fragment comprises at least seven contiguous amino acids, said polypeptide containing at least one immunological and antigenic determinant of a Herpes Simplex Virus type 2 dG glycoprotein, wherein the eucaryotic cell is capable of expressing the DNA sequence to produce said polypeptide and does not contain the entirety of Herpes Simplex Virus type 2 genetic information.

50. A eucaryotic cell containing an exogenous DNA sequence coding for a polypeptide comprising the amino acid sequence of a Herpes Simplex Virus type 2 gD glycoprotein or a fragment comprises at least seven contiguous amino acids, said polypeptide containing at least one immunological and antigenic determinant of a Herpes Simplex Virus type 2 gD glycoprotein, wherein the eucaryotic cell is capable of expressing the DNA sequence to produce said polypeptide and is not a natural host cell for Herpes Simplex Virus type 2.

51. The eucaryotic cell of claim 41 or 50, wherein at least one determinant is common to Herpes Simplex Virus type 1 and type 2.

52. A procaryotic cell containing an exogenous DNA sequence coding for a polypeptide comprising the amino acid sequence of a Herpes Simplex Virus type 2 gD glycoprotein or a fragment of said amino acid sequence, wherein said fragment comprises at least seven contiguous amino acids, said polypeptide containing at least one immunological and antigenic determinant of a Herpes Simplex Virus type 2 gD glycoprotein, wherein the procaryotic cell is capable of expressing the DNA sequence to produce said polypeptide.

53. An *Escherichia coli* bacterium containing the DNA sequence:

ATG GCG CGT TTG ACC TCC GGC GTC GGG ACG GCG GCC CTG CTA GTT GTC GCG GTG GGA CTC CGC GTC GTC TGC GCC AAA TAC GCC TTA GCA GAC CCC TCG CTT AAG ATG GCC GAT CCC AAT CGA TTT CGC GGG AAG AAC CTT CCG GTT TTG GAC CAG CTG ACC GAC CCC CCC GGG GTG AAG CGT GTT TAC CAC ATT

CAG CCG AGC CTG GAG GAC CCG TTC
CAG CCC CCC AGC ATC CCG ATC ACT
GTG TAC TAC GCA GTG CTG GAA CGT
GCC TGC CGC AGC GTG CTC CTA CAT
GCC CCA TCG GAG GCC CCC CAG ATC
GTG CGC GGG GCT TCG GAC GAG GCC
CGA AAG CAC ACG TAC AAC CTG ACC
ATC GCC TGG TAT CGC ATG GGA GAC
AAT TGC GCT ATC CCC ATC ACG GTT
ATG GAA TAC ACC GAG TGC CCC TAC
AAC AAG TCG TTG GGG GTC TGC CCC
ATC CGA ACG CAG CCC CGC TGG AGC
TAC TAT GAC AGC TTT AGC GCC GTC
AGC GAG GAT AAC CTG GGA TTC CTG
ATG CAC GCC CCC GCC TTC GAG ACC
GCG GGT ACG TAC CTG CGG CTA GTG
AAG ATA AAC GAC TGG ACG GAG ATC
ACA CAA TTT ATC CTG GAG CAC CGG
GCC CGC GCC TCC TGC AAG TAC GCT
CTC CCC CTG CGC ATC CCC CCG GCA
GCG TGC CTC ACC TCG AAG GCC TAC
CAA CAG GGC GTG ACG GTC GAC AGC
ATC GGG ATG TTA CCC CGC TTT ATC
CCC GAA AAC CAG CGC ACC GTC GCC
CTA TAC AGC TTA AAA ATC GCC GGG
TGG CAC GGC CCC AAG CCC CCG TAC
ACC AGC ACC CTG CTG CCG CCG GAG
CTG TCC GAC ACC ACC AAC GCC ACG
CAA CCC GAA CTC GTT CCG GAA GAC
CCC GAG GAC TCG GCC CTC TTA GAG
GAT CCC GCC GGG ACG GTG TCT TCG
CAG ATC CCC CCA AAC TGG CAC ATC
CCG TCG ATC CAG GAC GTC GCG CCG
CAC CAC GCC CCC GCC GCC CCC AGC
AAC CCG GGC CTG ATC ATC GGC GCG
CTG GCC GGC AGT ACC CTG GCG GCG
CTG GTC ATC GGC GGT ATT GCG TTT
TGG GTA CGC CGC CGC GCT CAG ATG
GCC CCC AAG CGC CTA CGT CTC CCC
CAC ATC CGG GAT GAC GAC GCG CCC
CCC TCG CAC CAG CCA TTG TTT TAC, or a subsequence thereof, which subsequence comprises at least 21 contiguous nucleotides of said sequence and codes on expression for a polypeptide having at least one immunological and antigenic determinant of a Herpes Simplex Virus type 2 gD glycoprotein, wherein said polypeptide comprises at least seven contiguous amino acids and said bacterium is capable of expressing the DNA sequence to produce said polypeptide.

54. An *Escherichia coli* bacterium containing a recombinant vector comprising the DNA sequence:
ATG GGG CGT TTG ACC TCC GGC GTC
GGG ACG GCG GCC CTG CTA GTT GTC
GCG GTG GGA CTC CGC GTC GTC TGC
GCC AAA TAC GCC TTA GCA GAC CCC
TCG CTT AAG ATG GCC GAT CCC AAT
CGA TTT CGC GGG AAG AAC CTT CCG
GTT TTG GAC CAG CTG ACC GAC CCC
CCC GGG GTG AAG CGT GTT TAC CAC
ATT CAG CCG AGC CTG GAG GAC CCG
TTC CAG CCC CCC AGC ATC CCG ATC
ACT GTG TAC TAC GCA GTG CTG GAA
CGT GCC TGC CGC AGC GTG CTC CTA
CAT GCC CCA TCG GAG GCC CCC CAG
ATC GTG CGC GGG GCT TCG GAC GAG
GCC CGA AAG CAC ACG TAC AAC CTG
ACC ATC GCC TGG TAT CGC ATG GGA
GAC AAT TGC GCT ATC CCC ATC ACG
GTT ATG GAA TAC ACC GAG TGC CCC
TAC AAC AAG TCG TTG GGG GTC TGC
CCC ATC CGA ACG CAG CCC CGC TGG
AGC TAC TAT GAC AGC TTT AGC GCC
GTC AGC GAG GAT AAC CTG GGA TTC
CTG ATG CAC GCC CCC GCC TTC GAG
ACC GCG GGT ACG TAC CTG CGG CTA
GTG AAG ATA AAC GAC TGG ACG GAG
ATC ACA CAA TTT ATC CTG GAG CAC
CGG GCC CGC GCC TCC TGC AAG TAC
GCT CTC CCC CTG CGC ATC CCC CCG
GCA GCG TGC CTC ACC TCG AAG GCC
TAC CAA CAG GGC GTG ACG GTC GAC
AGC ATC GGG ATG TTA CCC CGC TTT
ATC CCC GAA AAC CAG CGC ACC GTC
GCC CTA TAC AGC TTA AAA ATC GCC
GGG TGG CAC GGC CCC AAG CCC CCG
TAC ACC AGC ACC CTG CTG CCG CCG
GAG CTG TCC GAC ACC ACC AAC GCC
ACG CAA CCC GAA CTC GTT CCG GAA
GAC CCC GAG GAC TCG GCC CTC TTA
GAG GAT CCC GCC GGG ACG GTG TCT
TCG CAG ATC CCC CCA AAC TGG CAC
ATC CCG TCG ATC CAG GAC GTC GCG
CCG CAC CAC GCC CCC GCC GCC CCC
AGC AAC CCG GGC CTG ATC ATC GGC
GCG CTG GCC GGC AGT ACC CTG GCG
GCG CTG GTC ATC GGC GGT ATT GCG
TTT TGG GTA CGC CGC CGC GCT CAG
ATG GCC CCC AAG CGC CTA CGT CTC
CCC CAC ATC CGG GAT GAC GAC GCG
CCC CCC TCG CAC CAG CCA TTG TTT
TAC, or a subsequence thereof, which subsequence comprises at least 21 contiguous nucleotides of said sequence and codes on expression for a polypeptide having at least one immunological and antigenic determinant of Herpes Simplex Virus type 2 gD glycoprotein, wherein said polypeptide comprises at least seven contiguous amino acids and wherein said DNA sequence is connected in phase to a second DNA sequence coding for a protein, and the recombinant vector is capable of being replicated in said bacterium and said bacterium is capable of expressing the DNA sequence to produce said polypeptide.

55. An *Escherichia coli* bacterium containing a recombinant vector comprising a DNA sequence coding for a polypeptide comprising the amino acid sequence of a Herpes Simplex Virus type 2 gD glycoprotein or a fragment of said amino acid sequence, wherein said fragment comprises at least seven contiguous amino acids, said polypeptide containing at least one immunological and antigenic determinant of a Herpes Simplex Virus type 2 gD glycoprotein, wherein the recombinant vector is capable of being replicated in said bacterium and said bacterium is capable of expressing the DNA sequence to produce said polypeptide.

56. An *Escherichia coli* bacterium containing a recombinant vector comprising a DNA sequence coding for a polypeptide comprising the amino acid sequence of a Herpes Simplex Virus type 2 gD glycoprotein or a fragment of said amino acid sequence, wherein said fragment comprises at least seven contiguous amino acids, said polypeptide containing at least one immunological and antigenic determinant of a Herpes Simplex Virus type 2 gD glycoprotein, in which the DNA sequence is connected in phase to a second DNA sequence coding for a protein, and the recombinant vector is capable of being replicated in said bacterium and said bacterium is capable of expressing the DNA sequence to produce said polypeptide.

57. The bacterium of claim 55 or 56, wherein at least one determinant is common to Herpes Simplex Virus type 1 and type 2.

58. A unicellular organism containing the recombinant vector pHV5.

59. A unicellular organism containing the recombinant vector pHV6.

* * * * *